United States Patent
Ng et al.

(10) Patent No.: US 7,605,120 B2
(45) Date of Patent: Oct. 20, 2009

(54) ANTAGONISTS OF THE BRANDYKININ B1 RECEPTOR

(75) Inventors: Gordon Ng, Newbury Park, CA (US); Benny C. Askew, Jr., Marshfield, MA (US); Derin C. D'Amico, Newbury Park, CA (US); Mark A. Jarosinski, Fishers, IN (US); Chuan-Fa Liu, Waltham, MA (US)

(73) Assignee: Amgen Inc., Thousand Oaks, CA (US)

( * ) Notice: Subject to any disclaimer, the term of this patent is extended or adjusted under 35 U.S.C. 154(b) by 756 days.

(21) Appl. No.: 10/972,236

(22) Filed: Oct. 21, 2004

(65) Prior Publication Data

US 2005/0215470 A1    Sep. 29, 2005

Related U.S. Application Data

(60) Provisional application No. 60/513,913, filed on Oct. 22, 2003, provisional application No. 60/538,929, filed on Jan. 24, 2004.

(51) Int. Cl.
*A61K 38/08* (2006.01)
*A61K 38/10* (2006.01)

(52) U.S. Cl. .............................. 514/2; 514/13; 514/15; 530/326; 530/328

(58) Field of Classification Search ........................ None
See application file for complete search history.

(56) References Cited

U.S. PATENT DOCUMENTS

| | | | |
|---|---|---|---|
| 4,693,993 A | 9/1987 | Stewart et al. | |
| 4,801,613 A | 1/1989 | Stewart et al. | |
| 4,923,963 A | 5/1990 | Stewart et al. | |
| 5,252,714 A | 10/1993 | Harris et al. | |
| 5,385,889 A | 1/1995 | Kyle et al. | |
| 5,416,191 A | 5/1995 | Cheronis et al. | |
| 5,444,048 A | 8/1995 | Kyle | |
| 5,541,286 A | 7/1996 | Kyle | |
| 5,648,333 A | 7/1997 | Henke et al. | |
| 5,648,336 A | 7/1997 | Stewart et al. | |
| 5,700,779 A | 12/1997 | Goodfellow et al. | |
| 5,834,431 A * | 11/1998 | Stewart et al. | 514/15 |
| 5,849,863 A | 12/1998 | Stewart et al. | |
| 5,863,899 A | 1/1999 | Cheronis et al. | |
| 5,935,932 A | 8/1999 | Stewart et al. | |
| 6,075,120 A | 6/2000 | Cheronis et al. | |
| 6,388,054 B1 | 5/2002 | Stewart et al. | |
| 6,407,207 B1 | 6/2002 | Borkowski et al. | |

FOREIGN PATENT DOCUMENTS

| | | | |
|---|---|---|---|
| DE | 2435642 A | | 2/1976 |
| EP | 0318162 A | | 5/1989 |
| EP | 0885899 A | | 12/1998 |
| WO | WO98/07746 | | 2/1998 |
| WO | WO01/62827 A3 | | 8/2001 |

OTHER PUBLICATIONS

Regoli Domenico, et al., Bradykinin receptors and their antagonists. European Journal of Pharmacology, 348:1-10 (1998).
Stewart, John M., et al., Bradykinin antagonists: present progress and future prospects. Immunopharmacology, 43:155-161 (1999).
Stewart, John M., et al., Metabolism-Resistant Bradykinin Antagonists: Development and Applications. Biol. Chem., 382:37-41 (2001).
Morpurgo, Margherita, et al., Selective Alkylation and Acylation of α and β Amino Groups with PEG in a Somatostatin Analogue: Tailored Chemistry for Optimized Bioconjugates. Bioconjugate Chem. 13:1238-1243 (2002).
Neugebauer, Witold, et al., Kinin $B_1$ receptor antagonists with multienzymatic resistance properties. Can. J. Physiol. Pharmacol., 80:287-292 (2002).
Raymond, Philippe, et al. Quantification of des-$Arg^9$-bradykinin using a chemiluminescence enzyme immunoassay: application to its kinetic profile during plasma activation. J. Immun. Methods, 180:247-157 (1995).
Anderson, K.P., et al., "Primary Structure of a Gene Encoding Rat T-Kininogen" Gene (Amsterdam), 81(1); 119-128 (1989).
Zalipsky, S. et al., "Use ethylene glycol chemistry of Funcationalized Poly-Ethylene Glycol)s for Modificatioin of Polypeptides" Poly(Ethylene Glycol) Chemistry: Biotechnical and Biomedical Applications 1992, 347-3703:155-161 (1999).

* cited by examiner

*Primary Examiner*—Anish Gupta
(74) *Attorney, Agent, or Firm*—Nisan A. Steinberg

(57) ABSTRACT

The present invention relates to certain biologically active peptides and conjugated peptides which can be used as therapeutics or prophylactics against diseases or conditions linked to B1 as the causative agent. In a preferred embodiment of the invention biologically active PEG-conjugated peptides are provided. In one aspect of the present invention, pharmacologically active PEG-conjugated peptides of the present invention are useful to treat inflammation or pain.

11 Claims, No Drawings

ANTAGONISTS OF THE BRANDYKININ B1 RECEPTOR

This application claims the benefit of U.S. Provisional Application No. 60/513,913 filed Oct. 22, 2003, and U.S. Provisional Application No. 60/538,929 filed Jan. 24, 2004, which are hereby incorporated by reference.

BACKGROUND OF THE INVENTION

More than two million people in the United States alone are incapacitated by chronic pain on any given day (T. M. Jessell & D. D. Kelly, Pain and Analgesia in PRINCIPLES OF NEURAL SCIENCE, third edition (E. R. Kandel, J. H. Schwartz, T. M. Jessell, ed., (1991)). Unfortunately, current treatments for pain are only partially effective, and many also cause life-style altering, debilitating, and/or dangerous side effects. For example, non-steroidal anti-inflammatory drugs ("NSAIDs") such as aspirin, ibuprofen, and indomethacin are moderately effective against inflammatory pain but they are also really toxic, and high doses tend to cause gastrointestinal irritation, ulceration, bleeding, increased cardiovascular risk, and confusion. Patients treated with opioids frequently experience confusion and constipation, and long-term opioid use is associated with tolerance and dependence. Local anesthetics such as lidocaine and mixelitine simultaneously inhibit pain and cause loss of normal sensation. In addition, when used systemically local anesthetics are associated with adverse cardiovascular effects. Thus, there is currently an unmet need in the treatment of chronic pain.

Pain is a perception based on signals received from the environment and transmitted and interpreted by the nervous system (for review, see Millan, M. J., The induction of pain: an integrative review. Prog Neurobiol 57:1-164 (1999)). Noxious stimuli such as heat and touch cause specialized sensory receptors in the skin to send signals to the central nervous system ("CNS"). This process is called nociception, and the peripheral sensory neurons that mediate it are nociceptors. Depending on the strength of the signal from the nociceptor(s) and the abstraction and elaboration of that signal by the CNS, a person may or may not experience a noxious stimulus as painful. When one's perception of pain is properly calibrated to the intensity of the stimulus, pain serves its intended protective function. However, certain types of tissue damage cause a phenomenon, known as hyperalgesia or pronociception, in which relatively innocuous stimuli are perceived as intensely painful because the person's pain thresholds have been lowered. Both inflammation and nerve damage can induce hyperalgesia. Thus, persons afflicted with inflammatory conditions, such as sunburn, osteoarthritis, colitis, carditis, dermatitis, myositis, neuritis, inflammatory bowel disease, collagen vascular diseases (which include rheumatoid arthritis and lupus) and the like, often experience enhanced sensations of pain. Similarly, trauma, surgery, amputation, abscess, causalgia, collagen vascular diseases, demyelinating diseases, trigeminal neuralgia, cancer, chronic alcoholism, stroke, thalamic pain syndrome, diabetes, herpes infections, acquired immune deficiency syndrome ("AIDS"), toxins and chemotherapy cause nerve injuries that result in excessive pain.

As the mechanisms by which nociceptors transduce external signals under normal and hyperalgesic conditions become better understood, processes implicated in hyperalgesia can be targeted to inhibit the lowering of the pain threshold and thereby lessen the amount of pain experienced.

Bradykinin (BK) and the related peptide, kallidin (Lys-BK)(see Table 3) mediate the physiological actions of kinins on the cardiovascular and renal systems. However, the active peptides, BK and kallidin, are quickly degraded by peptidases in the plasma and other biological fluids and by those released from a variety of cells, so that the half-life of BK in plasma is reported to be approximately 17 seconds (1). BK and kallidin are rapidly metabolized in the body by carboxypeptidase N, which removes the carboxyterminal arginine residue to generate des-Arg BK or des-Arg kallidin. Des-Arg-kallidin is among the predominant kinins in man and mediate the pathphysiological actions of kinins in man. In addition to being a very potent proinflammatory peptide, des-Arg-BK or des-Arg-kallidin is known to induce vasodilation, vascular permeability, and bronchoconstriction (for review, see Regoli and Barabe, Pharmacology of Bradykinin and Related Kinins, Pharmacological Reviews, 32(1):1-46 (1980)). In addition, des-Arg-BK and des-Arg-kallidin appear to be particularly important mediators of inflammation and inflammatory pain as well as being involved in the maintenance thereof. There is also a considerable body of evidence implicating the overproduction of des-Arg-kallidin in conditions in which pain is a prominent feature such as septic shock, arthritis, angina, and migraine.

The membrane receptors that mediate the pleiotropic actions of kinins are of two distinct classes, designated B1 and B2. Both classes of receptors have been cloned and sequenced from a variety of species, including man (Menke, et al, Expression cloning of a human b1 bradykinin receptor. J. Biol. Chem. 269:21583-21586 (1994); Hess et al, Cloning and pharmacological characterization of a human bradykinin (BK-2) receptor. Biochem. Biophys. Res. Commun. 184, 260-268 (1992)). They are typical G protein coupled receptors having seven putative membrane spanning regions. In various tissues, BK receptors are coupled to every known second messenger. B2 receptors, which have a higher affinity for BK, appear to be the most prevalent form of bradykinin receptor. Essentially all normal physiological responses and many pathophysiological responses to bradykinin are mediated by B2 receptors.

B1 receptors, on the other hand, have a higher affinity for des-Arg-BK (see Table 3) compared with BK, whereas des-Arg-BK is inactive at B2 receptors. In addition, B1 receptors are not normally expressed in most tissues. Their expression is induced upon injury or tissue damage as well as in certain kinds of chronic inflammation or systemic insult (Marceau, F., et al., Kinin B1 receptors: a review. Immunpharmacology, 30:1-26 (1995)). Furthermore, responses mediated by B1 receptors are up-regulated from a null level following administration of bacterial lipopolysaccharide (LPS) or inflammatory cytokines in rabbits, rats, and pigs (Marceau et al., (1998)).

The pain-inducing properties of kinins coupled with the inducible expression of B1 receptors make the B1 receptor an interesting target in the development of anti-inflammatory, antinociceptive, antihyperalgesic and analgesic agents that may be directed specifically at injured tissues with minimal actions in normal tissues. While a variety of peptide antagonists targeting the B1 receptor have been identified, their development as therapeutic analgesics has been stymied by poor efficacious half-lives resulting from very rapid degradation by tissue and serum peptidases and efficient renal clearance. More recently, peptide analogs having non-natural amino acid substituents have been shown to be resistant to peptidases in in vitro stability assays (for review, see Regoli et al, Bradykinin receptors and their antagonists. European Journal of Pharmacology, 348:1-10 (1998); Stewart, J. M., et al, Bradykinin antagonists: present progress and future prospects. Immunopharmacology, 43:155-161 (1999); and Stewart, J. M., et al., Metabolism-Resistant Bradykinin Antagonists: Development and Applications. Biol. Chem., 382:37-41 (2001)).

Covalent conjugation of proteins with poly(ethylene glycol) (PEG) has been widely recognized as an approach to significantly extend the in vivo circulating half-lives of therapeutic proteins. PEGylation achieves this effect predominately by retarding renal clearance, since the PEG moiety adds considerable hydrodynamic radius to the protein (Zalipsky, S., et al., *Use of functionalized poly(ethylene glycol)s for modification of polypeptides.,* in *Poly(ethylene glycol) chemistry: Biotechnical and biomedical applications.,* J. M. Harris, Editor. (1992), Plenum Press: New York. p. 347-370.). Additional benefits often conferred by PEGylation of proteins include increased solubility, resistance to proteolytic degradation, and reduced immunogenicity of the therapeutic polypeptide. The merits of protein PEGylation are evidenced by the commercialization of several PEGylated proteins including PEG-Adenosine deaminase (Adagen™/Enzon Corp.), PEG-L-asparaginase (Oncaspar™/Enzon Corp.), PEG-Interferon α-2b (PEG-Intron™/Schering/Enzon), PEG-Interferon α-2a (PEGASYS™/Roche) and PEG-G-CSF (Neulasta™/Amgen) as well as many others in clinical trials. PEGylation of small therapeutic peptides, on the other hand, presents unique challenges and has not been broadly applied. One of the greatest obstacles to peptide PEGylation is the essential requirement that biological activity be preserved in the final conjugate. Because therapeutic peptides often comprise the minimal sequence required for activity and are therefore very small, they are relatively intolerant to substitution. PEG moieties are disproportionately larger than the peptide itself and consequently are more likely to interfere sterically with specific peptide:receptor binding interactions required for activity. Thus, a peptide's ability to tolerate PEGylation and still retain sufficient specific activity to be a useful therapeutic is quite unpredictable and must be empirically determined (Morpurogo, et al., Selective Alkylation and Acylation of α and ε Amino Groups with PEG in a Somatostatin Analogue: Tailored Chemistry for Optimized Bioconjugates. Bioconjugate Chem. 13:1238-1243 (2002)).

Clearly, there is a need for new, safe and effective treatments for inflammation and pain. It would be an advantage to have a B1 specific peptide antagonist that is better able to tolerate systemic exposure during treatment, by enhancing the circulating life (delayed clearance), solubility, stability, and/or decreasing the immunogenicity of the molecule. Increased circulating life would result in a less frequent dosing regimen and a less frequent dosing schedule would be more convenient to both physicians and patients, and would be particularly helpful to those patients involved in self-administration. Other advantages to less frequent dosing may include less drug being introduced into patients and increased compliance.

SUMMARY OF THE INVENTION

Accordingly, it is an object of the present invention to provide novel binding agents of the B1 receptor with demonstrably superior pharmacokinetic properties in vivo as compared to known peptide B1 antagonists yet sufficiently antagonize B1 receptor activity such that they are therapeutically useful in the treatment or prevention of inflammation, pain, and other B1 mediated conditions including, but not limited to, asthma and allergic rhinitis. Such agents are provided by the present invention in the form of novel peptide antagonists and conjugated peptide antagonists of the B1 receptor. In one embodiment, the novel B1 receptor peptide antagonists of the present invention comprise an amino acid sequence as shown in any one of SEQ ID NOS: 15-54.

According to some embodiments of this invention, one or more, and preferably between one to nine amino acid residues, independently selected from any of the twenty genetically coded L-amino acids or the stereoisomeric D-amino acids, will be coupled to either or both ends of the peptide sequences as shown in SEQ ID NOS: 15-54.

In another embodiment, the present invention also provides conjugated peptides which have demonstrably superior pharmacokinetic properties in vivo as compared to known peptide B1 antagonists yet they sufficiently bind to and antagonize the activity of the B1 receptor such that they may be used therapeutically.

One aspect of the invention comprises a conjugated peptide of formula I:

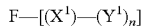

$$F—[(X^1)—(Y^1)_n] \qquad I$$

wherein:

F is a vehicle covalently bound to $X^1$ or $Y^1$ (preferably F is a PEG moiety or a derivative thereof);

$X^1$ and $Y^1$ are independently in each instance peptides of the formula $-L^1-P^1$ and $-L^2-P^2$, respectively;

$L^1$ and $L^2$ are independently in each instance linkers;

n is 0 to 3; and $P^1$ and $P^2$ are independently in each instance peptide antagonists of the bradykinin B1 receptor. Preferably, $P^1$ and $P^2$ comprise an amino acid sequence as shown in any one of SEQ ID NOS: 5-26, 43-60, and derivatives thereof.

Another object of the present invention is to provide a pharmaceutical composition comprising excipient carrier materials having a conjugated peptide of the invention dispersed therein.

Another object of the present invention is to provide therapeutic methods of treatment which comprise administration to a mammal in need thereof a pharmaceutically effective amount of a composition comprising excipients and at least one peptide and/or conjugated peptide of the invention.

The peptides and/or conjugated peptides of the invention have therapeutic value for the treatment of diseases mediated by B1 activation, including, but not limited to, inflammation and chronic pain states of inflammatory and neuropathic origin, septic shock, arthritis, osteoarthritis, angina, asthma, allergic rhinitis, and migraine.

The peptides and/or conjugated peptides of the invention may be used for therapeutic or prophylactic purposes by formulating them with appropriate pharmaceutical carrier materials and administering an effective amount to a patient, such as a human (or other mammal) in need thereof.

Additional useful peptides and/or conjugated peptides may result from conservative modifications of the amino acid sequences of the peptides and/or vehicle-conjugated peptides disclosed herein. Conservative modifications will produce peptides and/or conjugated peptides having functional, physical, and chemical characteristics similar to those of the peptides and/or conjugated peptide from which such modifications are made. Such conservatively modified forms of the peptides and/or conjugated peptides disclosed herein are also contemplated as being an embodiment of the present invention.

Another aspect of the invention relates to a method of making a conjugated peptide as described herein, comprising the steps of:

reacting a compound having the structure:

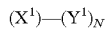

$$(X^1)—(Y^1)_N$$

wherein:

X¹ and Y¹ are independently in each instance peptides of the formula -L¹-P¹ and -L²-P², respectively;

L¹ and L² are independently in each instance linkers;

n is 0 to 3; and

P¹ and P² are independently in each instance peptide antagonists of the bradykinin B1 receptor, with a vehicle (F) to give a conjugated peptide of the formula: F—[(X¹)], F—[(X¹)]—F, F—[(X¹)—(Y¹)$_n$], F—(X¹)—(Y¹)$_n$, or F—(X¹)—(Y¹)$_n$—F. Preferably F is a PEG moiety or a derivative thereof. More preferably, P¹ and P² are independently in each instance peptide antagonists of the bradykinin B1 receptor comprising at least one of the peptide sequences shown in SEQ ID NOS: 5-60. Even more preferably, X¹ is a peptide as shown in SEQ ID NOS: 27-41. Additional aspects and advantages of the present invention will become apparent upon consideration of the detailed description of the invention which follows.

DETAILED DESCRIPTION OF THE INVENTION

The present invention is based upon the surprising finding that a class of peptides generally considered to be quite intolerant to substitution can be amino acid substituted at the N-terminus and/or conjugated to various vehicles at the N-terminus to provide therapeutically useful peptides and/or peptide conjugates with dramatically sustained efficacy profiles as compared to the known peptides of the same class, and therefore they allow for their use to manage inflammation and pain Thus, the peptides and/or peptide conjugates of the present invention provide tremendous therapeutic advantage over known B1 peptide antagonists. More particularly, the inventors have found that the previously described shortcomings in known B1 peptide antagonists with respect to their therapeautic use are surmountable by substituting amino acids at the N-terminus and/or conjugating the peptide antagonists to vehicles such as, but not limited to, polyethylene glycol (PEG) molecules using peptidyl or non-peptidyl linkers of defined size and composition which maximize preservation of antagonist activity and specificity while prolonging efficacious half-life in vivo. Additionally (or alternatively), it was discovered that despite the slightly reduced in vitro activity conferred to B1 peptide antagonists conjugated to larger PEG polymers, the extended circulating half-lives of the large PEG-conjugates provided significantly greater exposure and prolonged efficacy in vivo when compared to peptide conjugates conjugated to smaller PEG polymers. In addition, the present inventors have found that the size of the PEG molecule attached to a peptide antagonist of the B1 receptor is a critical parameter in optimizing the intrinsic antagonist activity and the efficacious half-life in vivo. For example, an acetylated peptide B1 antagonist demonstrated efficacy in relevant in vivo models of pain for a maximum of 4 hours following multiple dosing. Surprisingly, the same peptide conjugated to a 5 kD and a 20 kD PEG molecule in the manner disclosed herein demonstrated efficacy for up to 2 days and for at least 4 days, respectively, after a single bolus injection.

Before the peptide and vehicle- or PEG-conjugated peptide antagonists of the bradykinin B1 receptor of the present invention and methods for making and using such are described, it is to be understood that this invention is not limited to the particular peptides and/or conjugated peptide antagonists described, since peptides and/or conjugated peptide antagonists and methodologies contemplated by the present invention may, of course, vary slightly. It is to be understood that the terminology used herein is for the purpose of describing particular embodiments only, and is not intended to be limiting since the scope of the present invention will be limited only by the appended claims.

Bradykinin B1 receptor binding peptides contemplated for conjugation to a vehicle for purposes and in the manner as described herein include, but are not limited to, the novel B1 binding peptide antagonists disclosed herein as well as B1 binding peptide antagonists known in the art including, but not limited, to any peptide disclosed in any one of the following publications (each of which is hereby incorporated by reference in its entirety): Regoli et al., Bradykinin receptors and their antagonists. Eur. J. of Pharma., 348:1-10 (1998); Neugebauer, W., et al., Kinin B₁ receptor antagonists with multi-enzymatic resistance properties. Can. J. Physiol. Pharmacol., 80:287-292 (2002); Stewart, J. M., et al, Bradykinin antagonists: present progress and future prospects. Immunopharmacology, 43:155-161 (1999); Stewart, J. M., et al., Metabolism-Resistant Bradykinin Antagonists: Development and Applications. Biol. Chem., 382:37-41 (2001); PCT Publication WO 98/07746; and U.S. Pat. Nos. 4,693,993, 4,801,613, 4,923,963, 5,648,336, 5,834,431, 5,849,863, 5,935,932, 5,648,333, 5,385,889, 5,444,048, and 5,541,286.

The terms used throughout this specification are defined as follows, unless otherwise limited in specific instances.

Natural amino acid residues are discussed in three ways: full name of the amino acid, standard three-letter code, or standard single-letter code in accordance with the chart shown below.

| | | | |
|---|---|---|---|
| A = Ala | G = Gly | M = Met | S = Ser |
| C = Cys | H = His | N = Asn | T = Thr |
| D = Asp | I = Ile | P = Pro | V = Val |
| E = Glu | K = Lys | Q = Gln | W = Trp |
| F = Phe | L = Leu | R = Arg | Y = Tyr |

Unless clearly indicated otherwise, a designation herein of a natural or non-natural amino acid is intended to encompass both the D- and L-isomer of the amino acid. Abbreviations used herein for unnatural amino acids are the same as described in U.S. Pat. No. 5,834,431, PCT publication WO 98/07746, and Neugebauer, et al. (2002), each of which is hereby incorporated by reference in its entirety. Additionally, the abbreviation "Dab" and "D-Dab" is intended to refer to the L- and D-isomer of the unnatural amino acid, D-2-aminobutyric acid, respectively. The abbreviation "3'Pal" and "D-3'Pal" is intended to refer to the L- and D-isomer of the unnatural amino acid 3'-pyridylalanine, respectively. Also, the abbreviation "Igl" is intended to include both "Igla" and "Iglb" (α-(1-indanyl)glycine and α-(2-indanyl)glycine, respectively). Similarly, "D-Igl" is intended to include both "D-Igla" and "D-Iglb" (the D-isomers of α-(1-indanyl)glycine and α-(2-indanyl)glycine, respectively). Preferably, when used herein, Igl is Iglb and D-Igl is D-Iglb.

By "vehicle-conjugated peptide" or "conjugated peptide" is meant a compound which has biological activity and which when administered to a mammal provides a therapeutic effect. The two parts include (1) at least one B1 peptide antagonist and (2) at least one vehicle as defined hereinbelow covalently bound to a residue of the peptide itself or to a peptidyl or non-peptidyl linker (including but not limited to aromatic linkers) that is covalently bound to a residue of the peptide.

By "PEG-conjugated peptide" or "PEGylated peptide" is meant a two part compound which has biological activity and which when administered to a mammal provides a therapeutic effect. The two parts include (1) at least one B1 peptide antagonist and (2) at least one polyethylene glycol (PEG) moiety covalently bound to a residue of the peptide itself or to a peptidyl or non-peptidyl linker (including but not limited to aromatic linkers) that is covalently bound to a residue of the peptide.

By "polyethylene glycol" or "PEG" is meant a polyalkylene glycol compound or a derivative thereof, with or without coupling agents or derivatization with coupling or activating moieties (e.g., with thiol, triflate, tresylate, azirdine, oxirane, orthopyridyl disulphide, vinylsulfone, iodoacetamide or a maleimide moiety).

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). In the present application, the term "PEG" is used broadly to encompass any polyethylene glycol molecule, in mono- to poly functional form, without regard to size or to modification at an end of the PEG, and can be represented by the formula:

X—O(CH$_2$CH$_2$O)$_{n-1}$CH$_2$CH$_2$OH,  II where n is 20 to 2300 and X is H or a terminal modification, e.g., a C$_{1-4}$ alkyl.

Preferably, a PEG used in the invention terminates on one end with hydroxy or methoxy, i.e., X is H or CH$_3$ ("methoxy PEG"). It is noted that when X=CH$_3$, the other end of the PEG, which is shown in formula II terminating in OH, covalently attaches to an activating moiety via an ether oxygen bond. When X=H, both ends of the PEG are attached to activating moieties via ether bonds giving rise to linear bis-functionalized PEGs. When used in a chemical structure, the term "PEG" includes the formula II above without the hydrogen of the hydroxyl group shown, leaving the oxygen available to react with a free carbon atom of a linker to form an ether bond. More specifically, in order to conjugate PEG to a peptide, PEG must be in an "activated" form. Activated PEG can be represented by formula III:

(PEG)-(A)  III where PEG (defined supra.) covalently attaches to a carbon atom of the activation moiety (A) to form an ether bond, and (A) contains a reactive group which can react with an amino, imino, or thiol group on an amino acid residue of a peptide or a linker moiety covalently attached to the peptide.

Methods for the preparation of activated PEGs are well known in the art, e.g., see U.S. Pat. Nos. 5,643,575, 5,919,455, 5,932,462, and PCT publication WO 95/06058 (each of which is hereby incorporated by reference in their entirety). Suitable activated PEGs can be produced by a number of conventional reactions. For example, an N-hydroxysuccinimide ester of a PEG (M-NHS-PEG) can be prepared from PEG-monomethyl ether (which is commercially available from Union Carbide) by reaction with N,N'-dicyclohexylcarbodiimide (DCC) and N-hydroxysuccinimide (NHS), according to the method of Buckmann and Merr, Makromol. Chem., 182:1379-1384 (1981). Other activated PEGs, such as PEG-aldehydes, can be obtained from a commercial source, e.g., Nektar Therapeutics (Huntsville, Ala.) or Enzon, Inc. (Piscataway, N.J.). Examples of preferred activated PEG for purposes of the present invention are PEG-propionaldehyde and PEG-butyraldehyde which are commercially available from Nektar Therapeutics (Huntsville, Ala.). PEG-propionaldehyde is represented by the formula PEG-CH$_2$CH$_2$CHO and is described in U.S. Pat. No. 5,252,714, which is entirely incorporated by reference herein. In addition, bifunctional PEG aldehydes may be used to prepare dimeric conjugates.

Additional preferred amine reactive PEGs include: methoxy-PEG succinimidyl propionate (mPEG-SPA) and methoxy-PEG succinimido butanoate mPEG-SBA), mPEG-benzotriazole carbonate or mPEG-p-nitrophenyl carbonate which are available in a variety of molecular weights from Nektar Therapeutics (Huntsville, Ala.), Enzon, Inc. (Piscataway, N.J.), or NOF Corporation (Tokyo, Japan). Additional preferred activated PEG moieties include thiol reactive functionalities including, but not limited to, PEG vinyl sulfones, represented by the formula PEG-CH$_2$CH$_2$SO$_2$—CH=CH$_2$, mPEG-iodoacetate and mPEG-thioesters depicted below:

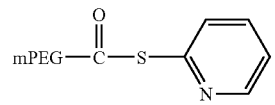

mPEG-thioester

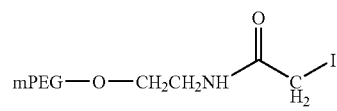

mPEG-Iodoacetamide

Another preferred activated PEG for generating the PEG-conjugated peptides of the present invention is PEG-maleimide. Compounds such as maleimido monomethoxy PEGs are particularly useful for generating the PEG-conjugated peptides of the invention.

An even more preferred activated PEG for generating the PEG-conjugated peptides of the present invention is a multivalent PEG having more than one activated residues. Preferred multivalent PEG moieties include, but are not limited to, those shown below:

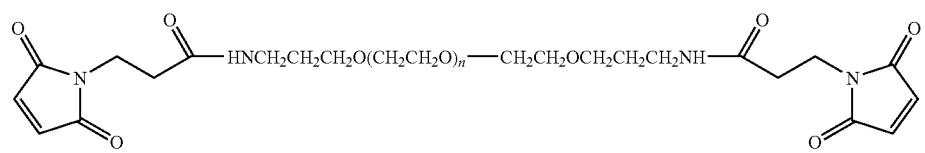

-continued
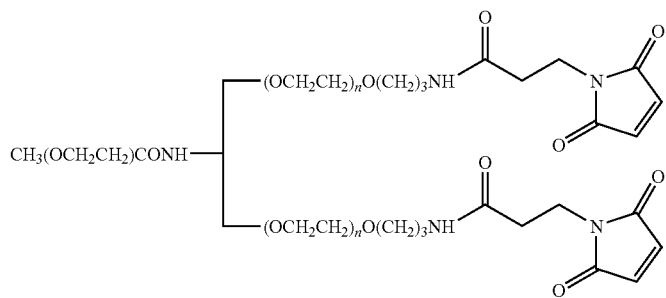
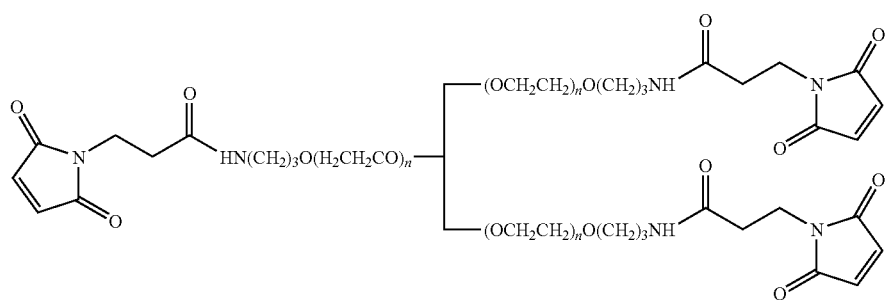
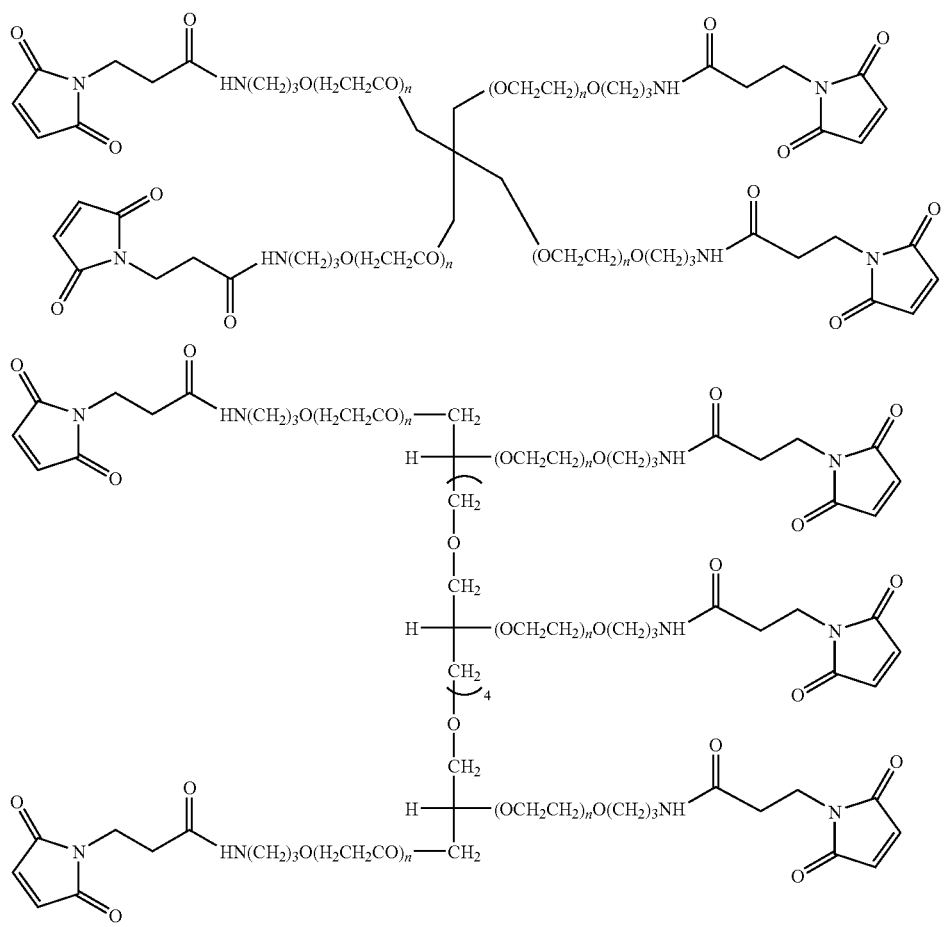

-continued

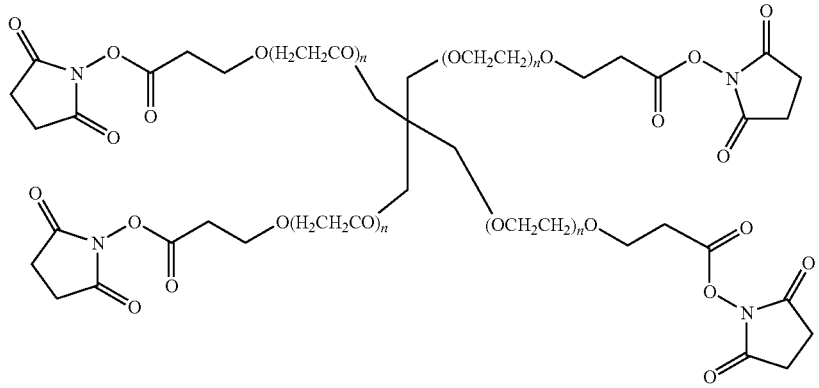

Any molecular mass for a PEG can be used as practically desired, e.g., from about 1,000 Daltons (Da) to 100,000 Da (n is 20 to 2300). The number of repeating units "n" in the PEG is approximated for the molecular mass described in Daltons. It is preferred that the combined molecular mass of PEG on an activated linker is suitable for pharmaceutical use. Thus, the combined molecular mass of the PEG molecules should not exceed 100,000 Da.

Preferably, the combined or total molecular mass of PEG used in a PEG-conjugated peptide of the present invention is from about 3,000 Da to 60,000 Da (total n is from 70 to 1,400), more preferably from about 8,800 Da to 36,000 Da (total n is about 200 to about 820). The most preferred combined mass for PEG is from about 20,000 Da to 24,000 Da (total n is about 450 to about 540).

Other polyalkylene glycol compounds, such as polypropylene glycol, may be used in the present invention. Other appropriate polyalkylene glycol compounds include, but are not limited to, charged or neutral polymers of the following types: dextran, colominic acids or other carbohydrate based polymers, polymers of amino acids, and biotin derivatives.

The term "comprising" means that a peptide or conjugated peptide may include additional molecular entities, including, but not limited to, amino acids, on either or both of the N- or C-termini of the given sequence. Of course, these additional molecular entities should not significantly interfere with the activity of the peptide or conjugated peptide.

As used herein, the term "native peptide" refers to an unconjugated B1 peptide antagonist disclosed herein or known in the art.

The terms "derivatizing" and "derivative" or "derivatized" comprise processes and resulting peptides or conjugated peptides, respectively, in which (1) the peptide or conjugated peptide has a cyclic portion; for example, cross-linking between cysteinyl residues within the conjugated peptide; (2) the peptide or conjugated peptide is cross-linked or has a cross-linking site; for example, the peptide or conjugated peptide has a cysteinyl residue and thus forms cross-linked dimers in culture or in vivo; (3) the N-terminus of a conjugated peptide having a —$NH_2$ terminal group is replaced by —$NRR^1$, $NRC(O)R^1$, —$NRC(O)OR^1$, —$NRS(O)_2R^1$, —NHC(O)NHR, a succinimide group, or substituted or unsubstituted benzyloxycarbonyl-NH—, wherein R and $R^1$ and the ring substituents are as defined hereinafter; (5) the C-terminus is replaced by —$C(O)R^2$ or —$NR^3R^4$ wherein $R^2$, $R^3$ and $R^4$ are as defined hereinafter; and (6) conjugated peptides in which individual amino acid moieties are modified through treatment with agents capable of reacting with selected side chains or terminal residues. Derivatives are further described hereinafter.

The term "B1" means the bradykinin B1 receptor (see, Judith M Hall, A review of BK receptors. Pharmac. Ther. 56:131-190 (1992)). Unless specifically noted otherwise, B1 or bradykinin B1 receptor is intended to mean the human bradykinin B1 receptor (hB1). Preferably, hB1 is the wild-type receptor. More preferably, hB1 is the bradykinin receptor described in GenBank Accession no. AJ238044.

The term "peptide" as used generally herein refers to molecules of 4 to 40 amino acids, with molecules of 10 to 20 amino acids being preferred and those of 15 to 18 amino acids being most preferred. The term "di-peptide" as used herein refers to a molecule of two amino acids. The term "tri-peptide" as used herein refers to a molecule of three amino acids.

Structural analysis of protein-protein interaction may also be used to suggest peptides that mimic the binding activity of large protein ligands. In such an analysis, the crystal structure may suggest the identity and relative orientation of critical residues of the protein ligand from which an analogous peptide may be designed. See, for example, Takasaki et al., Nature Biotech., Volume 15, pages 1266-1270 (1997). These analytical methods may also be used to investigate the interaction between a receptor protein and a peptide, vehicle-conjugated peptide, or PEG-conjugated peptide of the present invention, which may suggest further modification of the peptide or peptide conjugates to increase binding affinity.

As used herein, the terms "effective amount" and "therapeutically effective amount" when used with reference to a peptide, vehicle-conjugated peptide, or PEG-conjugated peptide B1 antagonist refers to an amount or dosage sufficient to produce a desired result (i.e., for therapy with the peptides, vehicle-conjugated peptides, and/or PEG-conjugated peptide B1 antagonists of the present invention. In the context of the present invention, the desired result is a desired reduction in inflammation and/or pain, for example, or to support an observable decrease in the level of one or more biological activities of B1. More specifically, a therapeutically effective amount is an amount of the peptide and/or conjugated peptide sufficient to inhibit, for some period of time, one or more of the clinically defined pathological processes associated with the condition at issue, e.g., inflammation or pain, in a subject treated in vivo with the agent(s). The effective amount may vary depending on the specific peptide and/or conjugated peptide B1 antagonist selected, and is also dependent on a variety of factors and conditions related to the subject to be treated and the severity of the disorder. For example, if the peptide and/or conjugated peptide B1 antagonist is to be administered in vivo, factors such as the age, weight and health of the patient as well as dose response curves and toxicity data obtained in preclinical animal work would be among those considered. If the agent(s) is to be contacted with the cells in vitro, one would also design a variety of pre-clinical in vitro studies to assess such parameters as uptake, half-life, dose, toxicity, etc. The determination of an effective amount or a therapeutically effective amount for a given agent is well within the ability of those skilled in the art.

The term "pharmacologically active" means that a substance so described is determined to have activity that affects a medical parameter or disease state (for example, pain). In the context of the invention, this term typically refers to a B1-induced or B1-mediated disease or abnormal medical condition or disorder, and more specifically, to antagonism of inflammation or pain.

The terms "antagonist", "inhibitor", and "inverse agonist" (e.g., see, Rianne A. F. de Ligt, et. al, British Journal of Pharmacology 2000, 130, 131) refer to a molecule that blocks, impedes, reduces, lessens or in some way interferes with the biological activity of the associated protein of interest. A preferred "antagonist" or "inhibitor" of the present invention is a molecule that binds to and inhibits B1 with an $IC_{50}$ of 500 nM or less in in vitro assays of B1 activity. A more preferred "antagonist" or "inhibitor" of the present invention is a molecule that binds to and inhibits B1 with an $IC_{50}$ of 100 nM or less in in vitro assays of B1 activity. A most preferred "antagonist" or "inhibitor" of the present invention is a molecule that binds to and inhibits B1 with an $IC_{50}$ of 50 nM or less in in vitro assays of B1 activity and prevents, ameliorates or abolishes pain as measured in at least one generally accepted in vivo animal model of pain and/or inhibits biochemical challenges in in vivo animal models of edema, inflammation, or pain.

Additionally, physiologically acceptable salts of the peptides or conjugated peptides of the invention are also encompassed herein. The phrases "physiologically acceptable salts" and "pharmacologically acceptable salts" as used herein are interchangeable are intended to include any salts that are known or later discovered to be pharmaceutically acceptable (i.e., useful in the treatment of a warm-blooded animal). Some specific examples are: acetate; trifluoroacetate; hydrohalides, such as hydrochloride and hydrobromide; sulfate; citrate; tartrate; glycolate; oxalate; salts of inorganic and organic acids, including, but not limited to, hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxy-carbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

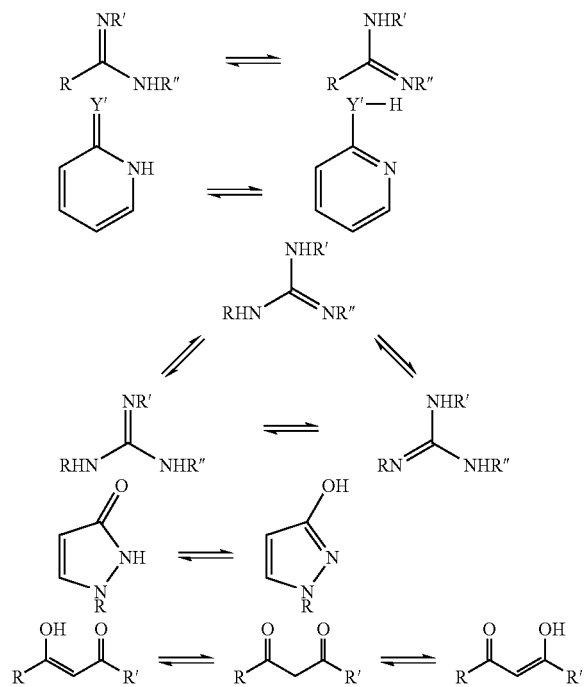

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Structure of Conjugated Peptides

In General. The vehicle-conjugated peptides of the present invention may be described by the following formula:

$$F-[(X^1)-(Y^1)_n]  \quad (IV)$$

wherein:

$X^1$ and $Y^1$ are independently in each instance peptides of the formula $-L^1-P^1$ and $-L^2-P^2$, respectively;

F is a vehicle covalently bound to $X^1$ or $Y^1$;

$L^1$ and $L^2$ are independently in each instance absent or linkers having from 0 to 9 amino acid residues;

n is 0 to 3; and $P^1$ and, if present, $P^2$ are independently in each instance peptide antagonists of the bradykinin B1 receptor.

The vehicle-conjugated peptides of formula IV will comprise preferred embodiments wherein $P^1$ and, if present, $P^2$ are independently in each instance peptide antagonists of the bradykinin B1 receptor having a peptide sequence as shown in any one of SEQ ID NOS: 5-60 and derivatives thereof.

Additional preferred embodiments of the vehicle-conjugated peptides will include vehicle-conjugated peptides of formula IV wherein $P^1$ and, if present, $P^2$ is defined by the formula:

$$NH_2-a^0a^1a^2a^3a^4a^5a^6a^7a^8a^9a^{10}a^{11}a^{12}a^{13}a^{14}\text{-COOH}$$

wherein:

$a^0$ is a basic or neutral aromatic, aliphatic, heterocyclic, or alicyclic amino acid, di-peptide or tri-peptide containing either one or two residues having basic side chains, or absent;

$a^1, a^2, a^3$, and $a^4$ are independently in each instance basic or neutral aromatic, aliphatic, heterocyclic, or alicyclic amino acids;

$a^6$ is Ser;

$a^5, a^7$, and $a^8$ are independently in each instance aromatic, aliphatic, heterocyclic, or alicyclic amino acids, provided that at least one of $a^5$, $a^7$, and $a^8$ is selected from Chg, Cpg, Igla, Iglb, Niga and Nigb of the D- or L-configuration; and $a^9$, $a^{10}$, $a^{11}$, $a^{12}$, $a^{13}$, and $a^{14}$ are independently in each instance any natural amino acid or absent.

More preferably, $P^1$ and, if present, $P^2$ are defined by the formula:

$$NH_2\text{-}a^0a^1a^2a^3a^4a^5a^6a^7a^8a^9a^{10}a^{11}a^{12}a^{13}a^{14}\text{-}COOH$$

wherein:

$a^0$ is a basic amino acid, a di-peptide containing either one or two residue with basic side chains, or absent;

$a^1$ is a basic amino acid;

$a^2$ is Pro;

$a^3$ is Hyp;

$a^4$ is Gly;

$a^5$ and $a^8$ is an Indanyl amino acid;

$a^6$ is Ser;

$a^7$ is a D-Indanyl amino acid;

$a^8$is Cpg; and $a^9$, $a^{10}$, $a^{11}$, $a^{12}$, $a^{13}$, and $a^{14}$ are independently in each instance any natural amino acid or absent.

Even more preferably, $P^1$ and, if present, $P^2$ are defined by the formula:

$$NH_2\text{-}a^0a^1a^2a^3a^4a^5\ a^6a^7a^8a^9a^{10}a^{11}a^{12}a^{13}a^{14}\text{-}COOH$$

wherein:

$a^0$ is a basic amino acid, di-peptide containing either one or two basic side chains, or absent;
$a^1$ is a basic amino acid;
$a^2$ is Pro;
$a^3$ is Hyp;
$a^4$ is Gly;
$a^5$ is Cpg;
$a^6$ is Ser;
$a^7$ is DTic;
$a^8$ is Cpg; and
$a^9$, $a^{10}$, $a^{11}$, $a^{12}$, $a^{13}$, and $a^{14}$ are independently in each instance any natural amino acid or absent.

Even more preferably, vehicle-conjugated peptides of the present invention include vehicle-conjugated peptides of formula IV wherein n=0 and $X^1$ is a peptide selected from the group consisting of peptides as shown in SEQ ID NOS: 27-41 and derivatives thereof.

The present invention also provides PEG-conjugated peptides which bind to and antagonize the activity of bradykinin B1 receptors (B1) and which have demonstrably superior pharmacokinetic properties in vivo as compared to unconjugated peptide B1 antagonists. The PEG-conjugated peptides of the present invention may be described by the following formula (V):

$$F-[(X^1)-(Y^1)_n] \qquad V$$

wherein:

$X^1$ and $Y^1$ are independently in each instance peptides of the formula $-L^1-P^1$ and $-L^2-P^2$, respectively;
F is a PEG moiety covalently bound to $X^1$ or $Y^1$;
$L^1$ and $L^2$ are independently in each instance absent or linkers having from 0 to 9 amino acid residues;
n is 0 to 3; and
$P^1$ and, if present, $P^2$ are independently in each instance peptide antagonists of the bradykinin B1 receptor.

The PEG-conjugated peptides of formula V will comprise preferred embodiments wherein $P^1$ and, if present, $P^2$ are independently in each instance peptide antagonists of the bradykinin B1 receptor having a peptide sequence as shown in any one of SEQ ID NOS: 5-60 and derivatives thereof.

Additional preferred embodiments of the PEG-conjugated peptides will include PEG-conjugates of formula V wherein $P^1$ and, if present, $P^2$ is defined by the formula:

$$NH_2-a^0a^1a^2a^3a^4a^5a^6a^7a^8a^9a^{10}a^{11}a^{12}a^{13}a^{14}-COOH$$

wherein:

$a^0$ is a basic or neutral aromatic, aliphatic, heterocyclic, or alicyclic amino acid, basic di-peptide or tri-peptide, or absent;
$a^1$, $a^2$, $a^3$, and $a^4$ are independently in each instance basic or neutral aromatic, aliphatic, heterocyclic, or alicyclic amino acids;
$a^6$ is Ser;
$a^5$, $a^7$, and $a^8$ are aromatic, aliphatic, heterocyclic, or alicyclic amino acids, provided that at least one of $a^5$, $a^7$, and $a^8$ is selected from Chg, Cpg, Igla, Iglb, Niga and Nigb of the D- or L-configuration; and
$a^9$, $a^{10}$, $a^{11}$, $a^{12}$, $a^{13}$, and $a^{14}$ are independently in each instance any natural amino acid or absent.

More preferably, $P^1$ and, if present, $P^2$ are defined by the formula:

$$NH_2-a^0a^1a^2a^3a^4a^5a^6a^7a^8a^9a^{10}a^{11}a^{12}a^{13}a^{14}-COOH$$

wherein:

$a^0$ is a basic amino acid, a basic di-peptide or absent;

$a^1$ is a basic amino acid;

$a^2$ is Pro;

$a^3$ is Hyp;

$a^4$ is Gly;

$a^5$ and $a^8$ is an Indanyl amino acid;

$a^6$ is Ser;

$a^7$ is a D-Indanyl amino acid;

$a^8$ is Cpg; and $a^9$, $a^{10}$, $a^{11}$, $a^{12}$, $a^{13}$, and $a^{14}$ are independently in each instance any natural amino acid or absent.

Even more preferably, $P^1$ and, if present, $P^2$ are defined by the formula:

$$NH_2-a^0a^1a^2a^3a^4a^5a^6a^7a^8a^9a^{10}a^{11}a^{12}a^{13}a^{14}-COOH$$

wherein:

$a^0$ is a basic amino acid, a basic di-peptide, or absent;

$a^1$ is a basic amino acid;

$a^2$ is Pro;

$a^3$ is Hyp;

$a^4$ is Gly;

$a^5$ is Cpg;

$a^6$ is Ser;

$a^7$ is DTic;

$a^8$ is Cpg; and $a^9$, $a^{10}$, $a^{11}$, $a^{12}$, $a^{13}$, and $a^{14}$ are independently in each instance any natural amino acid or independently absent.

Even more preferred PEG-conjugated peptides of the present invention include PEG-conjugated peptides of formula V wherein n=0 and $X^1$ is a peptide selected from the group consisting of peptides having an amino acid sequence as shown in SEQ ID NOS: 27-41 and derivatives thereof. Even more preferred PEG-conjugated peptides of the present invention include wherein n=0 and $X^1$ is a peptide selected from the group consisting of peptides having an amino acid sequence as shown in SEQ ID NOS: 27-41 and derivatives thereof. Even more preferably, the PEG-conjugated peptides of the present invention may be described by the following formula:

$$F'—R_z, \quad VI$$

or a physiologically acceptable salt thereof, wherein:

F' is a multivalent vehicle;

R is independently in each instance $—(X^1)—(Y^1)_n$ wherein R is covalently bound to F';

$X^1$ and $Y^1$ are independently in each instance peptides of the formula $-L^1-P^1$ and $-L^2-P^2$, respectively;

$L^1$ and $L^2$ are independently in each instance absent or linkers having from 0 to 9 amino acid residues;

n is 0 to 3;

Z is 2 to 8; and $P^1$ and $P^2$ are independently in each instance peptide antagonists of the bradykinin B1 receptor.

Even more preferred PEG-conjugated peptides of the present invention include PEG-conjugated peptides of formula VI wherein n is 0, Z is 4 to 8, and $X^1$ is a peptide selected from the group consisting of peptides having an amino acid sequence as shown in SEQ ID NOS: 27-41 and derivatives thereof.

Also intended as part of the present invention are peptide conjugates having peptide sequences that are fragments (i.e., "subsequences"), analogs, and derivatives of $P^1$ and, if present, $P^2$ as defined herein and wherein such conjugated peptides are substantially equivalent with respect to in vitro and/or in vivo anti-B1 activity as the peptide conjugates specifically disclosed herein.

The term "analog" is intended to mean molecules representing one or more amino acid substitutions, deletions and/or additions derived from the linear array of amino acids of the peptides, conjugated-peptides (unconjugated $P^1$ and, if present, $P^2$), and/or any peptidyl linker (L) of the vehicle- or PEG-conjugated peptides provided for by the formulas (IV) and (V), respectively, and which result in molecules which are substantially equivalent with respect to in vitro and/or in vivo anti-B1 activity as compared to an analogous unconjugated peptide or conjugated peptide specifically disclosed herein.

The conjugated peptide analogs in accordance with this invention will typically have one or more amino acid substitutions, deletions and/or insertions in the sequence of (P) ($P^1$ and/or, if present, $P^2$) or (L) ($L^1$ and/or, if present, $L^2$). It is generally recognized that conservative amino acid changes are least likely to perturb the structure and/or function of a polypeptide and generally involve substitution of one amino acid with another that is similar in structure and/or function (e.g., amino acids with side chains similar in size, charge and/or shape). The nature of these substitutions are well known to one skilled in the art and exemplary amino acid substitutions are summarized in Tables 1 and 2.

TABLE 1

Amino Acid Substitutions

Basic:

Arg; Lys; His;
Acidic:

Glu; Asp
Polar:

Glu; Asp; Gln; Asn; Ser; Thr
Hydrophilic:

Asp; Glu; Asn; Ser; Thr; Tyr
Hydrophobic:

Ala; Met; Ile; Leu; nor-Leu; Val
Aromatic:

Phe; Trp; Tyr
Small:

Gly; Ala; Ser; Thr; Met

TABLE 2

Amino Acid Substitutions

| Amino Acid | Preferred Substitutions | Most Preferred Substitution |
|---|---|---|
| Ala | Gly; Leu; Ile; Asn; Pro | Val |
| Arg | Ala; Asn; Gln; Ser | Lys |
| Asn | Arg; Gln; His; Lys; Ser; Tyr | Gln |
| Asp | Asn; Ser; Thr; Gln | Glu |
| Cys | Ala | Ser |
| Gln | Ala; Arg; Glu; Leu; Lys; Met; Ser; Tyr | Asn |
| Glu | Gln; Ser; Thr; Asn | Asp |
| Gly | | Pro |
| His | Asn; Gln; Lys; Tyr; Phe | Arg |
| Ile | Tyr; Val; Met; Ala; Phe; nor-Leu | Leu |
| Leu | nor-Leu; Ile; Val; Met; Ala; Phe | Ile |
| Lys | Asn; Asp; Ala; Glu; Gln; Ser; Tyr | Arg |

TABLE 2-continued

Amino Acid Substitutions

| Amino Acid | Preferred Substitutions | Most Preferred Substitution |
|---|---|---|
| Met | Ala; Gln; Tyr; Trp; Phe | Leu |
| Phe | Leu; Val; Ile; Ala; Met | Leu |
| Pro | Ile; Val | Gly |
| Ser | Ala; Asn; Asp; Gly; Lys | Thr |
| Thr | Ala; Gly; Ile; Val; Lys | Ser |
| Trp | Phe; Tyr; His | Tyr |
| Tyr | Trp; Thr; Ser | Phe |
| Val | Ala; Ile; Met; Phe; Tyr; nor-Leu | Leu |

Changing from A, F, H, I, L, M, P, V, W, or Y to C is more preferred if the new cysteine remains as a free thiol.

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the unconjugated and/or conjugated peptide molecules described herein.

In certain embodiments, conservative amino acid substitutions also encompass non-naturally occurring amino acid residues which are typically incorporated by chemical peptide synthesis.

As noted in the foregoing section, naturally occurring residues may be divided into classes based on common side chain properties that may be useful for modifications of sequence. For example, non-conservative substitutions may involve the exchange of a member of one of these classes for a member from another class. Such substituted residues may be introduced into regions of the peptide that are homologous with non-human orthologs, or into the non-homologous regions of the molecule. In addition, one may also make modifications using P or G for the purpose of influencing chain orientation.

In making such modifications, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.,* 157: 105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable analogs of the unconjugated and/or conjugated peptides set forth herein using well known techniques. One skilled in the art would also know that one may substitute chemically similar amino acids for residues occurring in the native peptide while retaining activity (conservative amino acid residue substitutions). Therefore, even areas that may be important for biological activity or for structure may be subject to conservative amino acid substitutions without destroying the biological activity or without adversely affecting the unconjugated peptide or conjugated peptide structure.

Additionally, one skilled in the art can review structure-function studies identifying residues within the unconjugated and/or conjugated peptide sequence that are important for activity or structure. In view of such a comparison, one can predict the importance of amino acid residues in a peptide sequence. One skilled in the art may opt to substitute chemically similar amino acid substitutions for such predicted important amino acid residues of unconjugated and/or conjugated peptides of the present invention.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure.

Additional methods of predicting secondary structure include "threading" (Jones, D., Curr. Opin. Struct. Biol., 7(3): 377-87 (1997); Sippl et al., Structure, 4(1): 15-9 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-8 (1987)), and "evolutionary linkage" (See Home, supra, and Brenner, supra).

Peptide and/or conjugated peptide analogs and derivatives in accordance with the invention will be useful for the same purposes for which the analogous peptides and/or conjugated peptides specifically disclosed herein are useful (i.e., antagonists of B1 activity in vitro and/or in vivo).

Peptides. Peptides of the present invention include peptides comprising the sequences shown in SEQ ID NOS: 15-35 and 39-54. The peptide sequences $P^1$ and, if present, $P^2$ (P) within the vehicle- or PEG-conjugated peptides of the present invention include, as mentioned, peptides that bind to and antagonize (e.g., decrease) the activity of B1. Preferred vehicle- or PEG-conjugated peptides of the present invention comprise at least one peptide sequence selected from the group consisting of SEQ ID NOS: 5-60 and derivatives thereof. More preferably, vehicle- or PEG-conjugated peptides of the present invention comprise at least one peptide sequence selected from the group consisting of SEQ ID NOS: 27-41 and derivatives thereof.

TABLE 3

Bradykinin Peptides

| Receptor/Effect | Peptide | Peptide Sequence | | | | | | | | | | | |
|---|---|---|---|---|---|---|---|---|---|---|---|---|---|
| B2/B1 Agonist | Bradykinin, BK (SEQ ID NO:1) | | | | Arg | Pro | Pro | Gly | Phe | Ser | Pro | Phe | Arg |
| B2 Agonist | Kallidin, Lys-BK (SEQ ID NO:2) | | | Lys | Arg | Pro | Pro | Gly | Phe | Ser | Pro | Phe | Arg |
| B2 Agonist | Met-Lys-BK (SEQ ID NO:3) | | Met | Lys | Arg | Pro | Pro | Gly | Phe | Ser | Pro | Phe | Arg |
| B1 Agonist | des-Arg-BK (SEQ ID NO:4) | | | | Arg | Pro | Pro | Gly | Phe | Ser | Pro | Phe | |
| B1 Antagonist | [Leu8]-Des-Arg9-BK (SEQ ID NO:5) | | | | Arg | Pro | Pro | Gly | Phe | Ser | Pro | Leu | |
| B1 Antagonist | DALK (SEQ ID NO:6) | | | Lys | Arg | Pro | Pro | Gly | Phe | Ser | Pro | Leu | |
| B2 Antagonist | (SEQ ID NO:7) | | | DArg | Arg | Pro | Hyp | Gly | Thi | Ser | DTic | Oic | Arg |
| B1/B2 Antagonist | (SEQ ID NO:8) | | | DArg | Arg | Pro | Hyp | Gly | Thi | Ser | DTic | Oic | |
| B2 Antagonist | (SEQ ID NO:9) | | | DArg | Arg | Pro | Hyp | Gly | Thi | Ser | DHpe | Oic | Arg |
| B1 Antagonist | (SEQ ID NO:10) | Ac | Lys | Lys | Arg | Pro | Pro | Gly | Me-Phe | Ser | D-β-NaI | Ile | |
| B1/B2 Antagonist | (SEQ ID NO:11) | | | DArg | Arg | Pro | Hyp | Gly | Igl | Ser | DIgl | Oic | Arg |

TABLE 3-continued

Bradykinin Peptides

| Receptor/Effect | Peptide | Peptide Sequence |
|---|---|---|
| B1 Antagonist | (SEQ ID NO:12) | Lys Lys Arg Pro Hyp Gly Igl Ser DIgl Oic |
| B1 Antagonist | (SEQ ID NO:13) | Lys Lys Arg Pro Hyp Gly Cpg Ser Dtic Cpg |
| B1/B2 Antagonist | (SEQ ID NO:14) | DArg Arg Pro Hyp Gly Igl Ser Df5f Igl Arg |
| B1 Antagonist | (SEQ ID NO:15) | DOrnLys Arg Pro Hyp Gly Cpg Ser Dtic Cpg |
| B1 Antagonist | (SEQ ID NO:16) | DOrnLys Arg Pro Thz Gly Cpg Ser Dtic Cpg |
| B1 Antagonist | (SEQ ID NO:17) | 3PalLys Arg Pro Hyp Gly Cpg Ser Dtic Cpg |
| B1 Antagonist | (SEQ ID NO:18) | 4PalLys Arg Pro Hyp Gly Cpg Ser Dtic Cpg |
| B1 Antagonist | (SEQ ID NO:19) | Cha Arg Pro Hyp Gly Cpg Ser Dtic Cpg |
| B1 Antagonist | (SEQ ID NO:20) | 2-NalArg Pro Hyp Gly Cpg Ser Dtic Cpg |
| B1 Antagonist | (SEQ ID NO:21) | Lys Arg Pro Hyp Gly Cpg Ser Dtic Cpg |
| B1 Antagonist | (SEQ ID NO:22) | DLysLys Arg Pro Hyp Gly Cpg Ser Dtic Cpg |
| B1 Antagonist | (SEQ ID NO:23) | Lys DOrn Arg Pro Hyp Gly Cpg Ser Dtic Cpg |
| B1 Antagonist | (SEQ ID NO:24) | Lys Cha Arg Pro Hyp Gly Cpg Ser Dtic Cpg |
| B1 Antagonist | (SEQ ID NO:25) | Lys Abu Arg Pro Hyp Gly Cpg Ser Dtic Cpg |
| B1 Antagonist | (SEQ ID NO:26) | Lys 2-NalArg Pro Hyp Gly Cpg Ser Dtic Cpg |
| B1 Antagonist | (SEQ ID NO:43) | D-Dab Lys Arg Pro Hyp Gly Cpg Ser Dtic Cpg |
| B1 Antagonist | (SEQ ID NO:44) | Ac D-Dab Lys Arg Pro Hyp Gly Cpg Ser Dtic Cpg |
| B1 Antagonist | (SEQ ID NO:45) | DOrnLys Arg Pro Hyp Gly Cpg Ser Dtic Cpg |
| B1 Antagonist | (SEQ ID NO:46) | Ac DOrnLys Arg Pro Hyp Gly Cpg Ser Dtic Cpg |
| B1 Antagonist | (SEQ ID NO:47) | D-3'Pa 1 Lys Arg Pro Hyp Gly Cpg Ser Dtic Cpg |
| B1 Antagonist | (SEQ ID NO:48) | Ac D-3'Pa 1 Lys Arg Pro Hyp Gly Cpg Ser Dtic Cpg |
| B1 Antagonist | (SEQ ID NO:49) | Lys D-2-Nal Arg Pro Hyp Gly Cpg Ser Dtic Cpg |
| B1 Antagonist | (SEQ ID NO:50) | Lys D-2-Nal Arg Pro Hyp Gly Cpg Ser Dtic Cpg |
| B1 Antagonist | (SEQ ID NO:51) | DOrn Arg Oic Pro Gly Phe Ser D-β-NaI Me-Ile |
| B1 Antagonist | (SEQ ID NO:52) | Ac DOrn Arg Oic Pro Gly Phe Ser D-β-NaI Me-Ile |
| B1 Antagonist | (SEQ ID NO:53) | DOrn LysArg Oic Pro Gly Phe Ser D-β-NaI Me-Ile |
| B1 Antagonist | (SEQ ID NO:54) | Ac DOrnLys Arg Oic Pro Gly Phe Ser D-β-NaI Me-Ile |
| B1 Antagonist | (SEQ ID NO:55) | Lys Arg Pro Pro Gly Phe Ser D-β-NaI Ile |
| B1 Antagonist | (SEQ ID NO:56) | Ac Lys Arg Pro Pro Gly Phe Ser D-β-NaI Me-Ile |

TABLE 3-continued

Bradykinin Peptides

| Receptor/Effect | Peptide | | | | | | | | | |
|---|---|---|---|---|---|---|---|---|---|---|
| | | | Peptide Sequence | | | | | | | |
| B1 Antagonist | (SEQ ID NO:57) | | Orn | Arg | Oic | Pro | Gly | Phe Me- | Ser | D-β-NaI Ile |
| B1 Antagonist | (SEQ ID NO:58) | Ac | Orn | Arg | Oic | Pro | Gly | Phe Me- | Ser | D-β-NaI Ile |
| B1 Antagonist | (SEQ ID NO:59) | | Lys | Arg | Oic | Pro | Gly | Phe Me- | Ser | D-β-NaI Ile |
| B1 Antagonist | (SEQ ID NO:60) | Ac | Lys | Arg | Oic | Pro | Gly | Phe | Ser | D-β-NaI Ile |

Vehicles. The term "vehicle" as used herein refers to a molecule that prevents degradation and/or increases half-life, reduces toxicity, reduces immunogenicity, or increases biological activity of a therapeutic peptide or protein. Vehicles useful in the context of the present invention are known in the art (for example, see PCT Publication WO 98/07746, which is hereby incorporated by reference in their entirety) and are all readily available to those skilled in the art. In the context of the present invention, preferred vehicles include, but are not limited to, polymethylethyleneglycol, polyhydroxypropyleneglycol, polypropyleneglycols and oxides, polymethylpropyleneglycol, polyhydroxypropyleneoxide, straight-chain and branched-chain polypropyleneglycols and derivatives thereof, polyethyleneglycol and polypropyleneglycol and the monomethyl ethers, monocetyl ethers, mono-n-butyl ethers, mono-t-butylethers and monooleyl ethers thereof, esters of polyalkyleneglycols with carboxylic acids and dehydration condensation products of the polyalkyleneglycols with amines and other polyalkylene oxides and glycols and derivatives thereof, poly(vinylpyrrolidone), polyvinyl alcohol, poly(vinyl acetate), the copolymer poly(vinyl acetate-co-vinyl alcohol), polyvinyloxazolidone, poly(vinylmethyloxazolidone and poly(vinyl methyl ether), poly(acrylic acid)s, poly(methacrylic acid)s, polyhydroxyethylmethacrylates, Poly (acrylamide and poly(methacrylamide) and other amides— thereof, poly(N,N-dimethylacrylamide), poly(N-isopropylacrylamide), poly(N-acetamidoacrylamide) and poly(N-acetamidomethacrylamide, and other N-substituted derivatives of the amides.

One aspect of the invention requires the presence of at least one vehicle (F) attached to a non-peptidyl linker moiety or an amino acid residue of a peptidyl linker that is covalently fused to a peptide B1 antagonist. In the context of the present invention, a preferred vehicle constitutes a PEG molecule, as defined herein. An even more preferred vehicle constitutes a multivalent PEG molecule, as defined herein.

The vehicle- or PEG-conjugated molecules specifically disclosed or referenced herein may be slightly modified within the regions denoted by $(X^1)$—$(Y^1)_n$ (as defined supra.) to form an analog in accordance with the invention, provided that antagonism of B1 is substantially maintained.

As between the vehicle- or PEG-conjugated peptides of the present invention and analogs thereof, it is preferable that no more than three non-terminal residues in the (P) region are different. More preferably, analogs contemplated by the present invention include molecules with up to two amino acid substitutions, insertions, or deletions at any particular non-terminal locus of the (P) region of the vehicle- or PEG-conjugated peptide of the present invention. Most preferably, the divergence in sequence between a vehicle- or PEG-conjugated peptide of the present invention and a contemplated analog thereof, particularly in the specified (P) region, is in the form of one or more "conservative modifications".

Linkers. The term "linker" as used herein refers to $L^1$ and, if present, $L^2$ as shown in either formula IV and V (supra.) and is abbreviated herein by (L). Preferably, (L) is peptidyl in nature (i.e., made up of amino acids linked together by peptide bonds) and made up of from 1 to 9 amino acids. More preferably, (L) is made up of from 1 to 9 amino acids, wherein the amino acids are selected from the twenty naturally occurring amino acids. In an even more preferred embodiment the 1 to 9 amino acids of the peptidyl linker are selected from cysteine, glycine, alanine, proline, arginine, asparagine, glutamine, and lysine. Even more preferably, a peptidyl linker is made up of a majority of amino acids that are sterically unhindered, such as glycine and alanine linked by a peptide bond. Thus, preferred peptidyl linkers are poly(Gly)$_{1-8}$, particularly (Gly)$_3$ (SEQ ID NO:61), (Gly)$_5$ (SEQ ID NO:62) and (Gly)$_7$ (SEQ ID NO:63), as well as poly(Gly-Ala)$_{2-4}$ and poly(Ala)$_{1-8}$. Other specific examples of peptidyl linkers include (Gly)$_5$Lys (SEQ ID NO:64), and (Gly)$_5$LysArg (SEQ ID NO:65). Other combinations of Gly and Ala are also preferred. To explain the above nomenclature, for example, (Gly)$_5$Lys means Gly-Gly-Gly-Gly-Gly-Lys (SEQ ID NO:64). A peptidyl linker may contain a N-terminal cysteine, another thiol, or nucleophile for conjugation with a vehicle. A more preferred linker contains an N-terminal cysteine or homocysteine residue, or other 2-amino-ethanethiol or 3-amino-propanethiol moiety for conjugation to maleimide, iodoacetaamide or thioester, functionalized vehicles. Treatment of the initial 3-sulfanyl succinimide adduct (1c) formed by the reaction of a peptide with maleimide activated PEG, with excess base converts the less stable succinimide adduct to the hydrolytically stable 6-methylcarbamoyl-5-oxo-thiomorpholine-3-carboxamide form (1d, Scheme 1). Alternatively, commercially available thioester or iodoacetamido PEGs(Nektar Therapeutics, Huntsville, Ala.) may be used for chemoselective conjugation as depicted in Schemes 2 and 3.

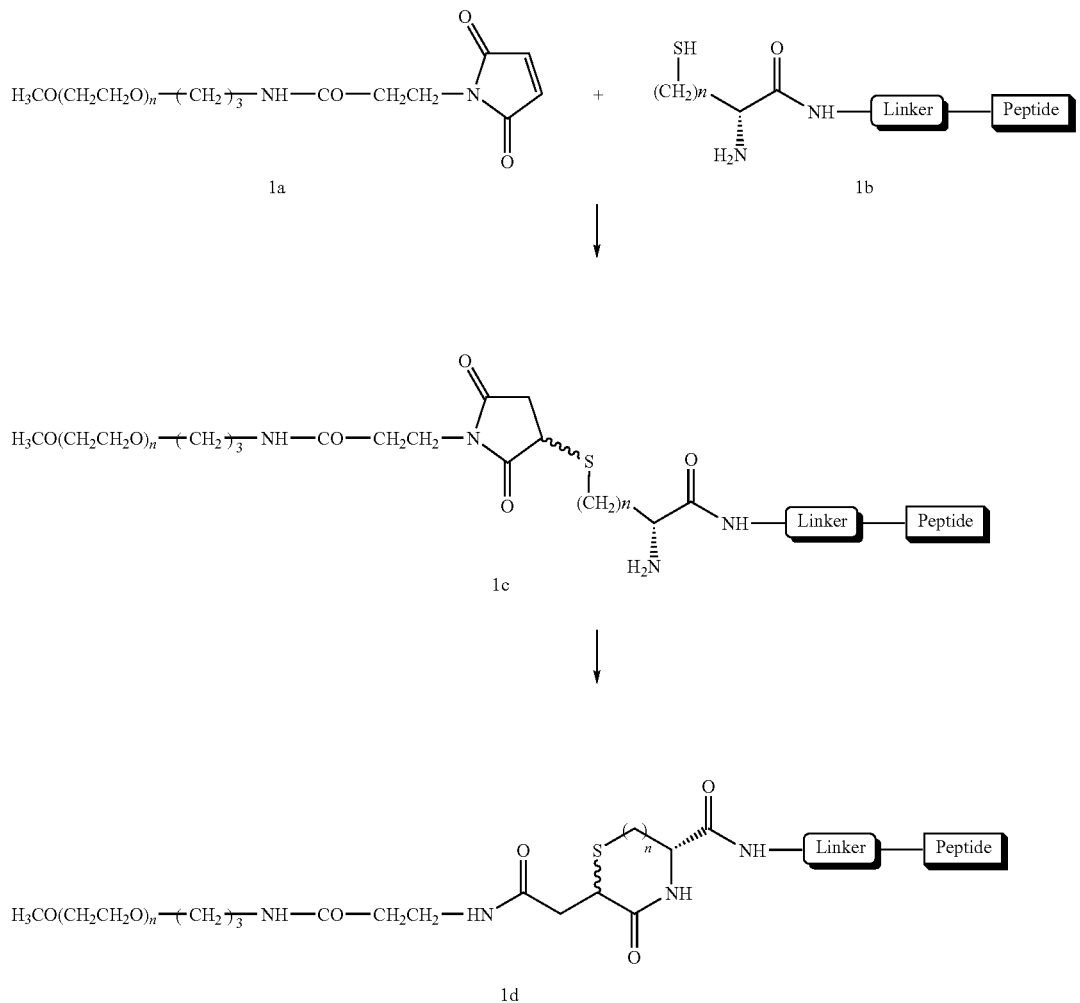
Scheme 1
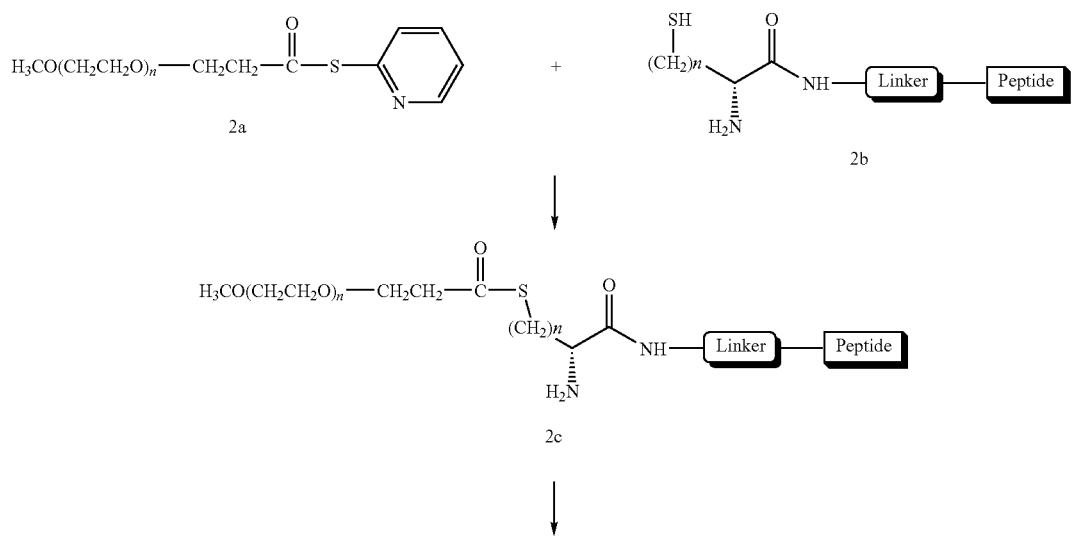
Scheme 2

-continued

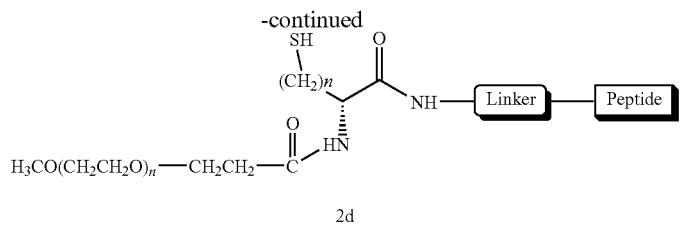

2d

Scheme 3

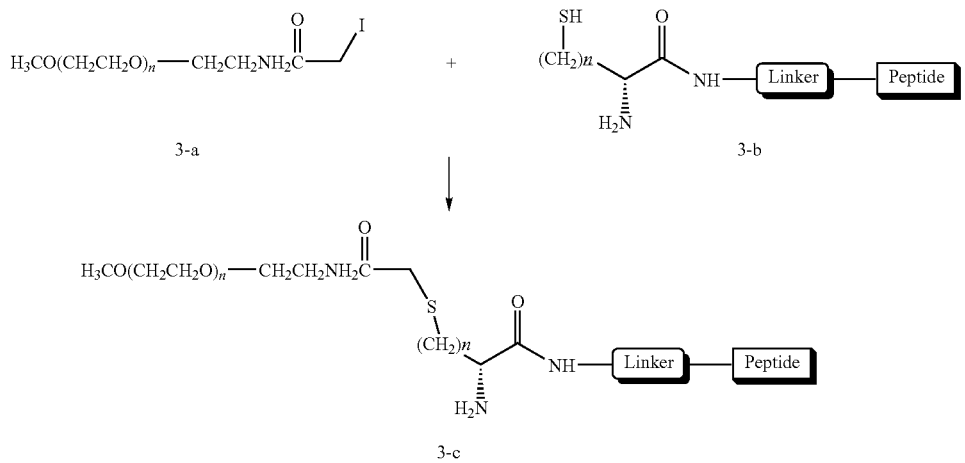

Another preferred linker is a large, flexible linker comprising a random Gly/Ser/Thr sequence (GSGSATGGSG-STASSGSGSATH; SEQ ID NO:66) that is estimated to be about the size of a 1 k PEG molecule. Additionally, a peptidyl linker may comprise a non-peptidyl segment such as a 6 carbon aliphatic molecule of the formula $CH_2$—$CH_2$—$CH_2$—$CH_2$—$CH_2$—$CH_2$— (Rigid linker: -AE-AAAKEAAAKEAAAKAGG-//SEQ ID NO:67).

Alternatively, a non-peptidyl linker containing a reactive nucleophile may be present in $X^1$ and, if present, $Y^1$. For example, alkyl linkers such as —NH—$(CH_2)_s$—C(O)—, wherein s=2-20 could be used. These alkyl linkers may further be substituted by any non-sterically hindering 15 group such as lower alkyl (e.g., $C_1$-$C_6$) lower acyl, halogen (e.g., Cl, Br), CN, $NH_2$, phenyl, etc. Exemplary non-peptidyl linkers are the PEG linkers (shown below):

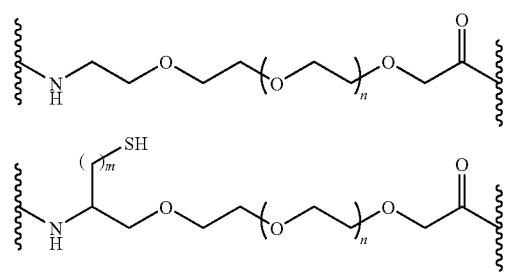

wherein n is such that the linker has a molecular weight of 100 to 5000 kilodaltons (kD), preferably 100 to 500 kD m is =1-3.

Preferably, a non-peptidyl linker is aromatic. The linkers may be altered to form derivatives in the same manner as described herein.

In addition, PEG moieties may be attached to the N-terminal amine or selected side chain amines by either reductive alkylation using PEG aldehydes or acylation using hydroxysuccinimido or carbonate esters of PEG. Any of the linkers described above may be used in this approach. Alternatively, a suitably functionalized PEG may be attached directly to any of the peptide antagonists of the bradykinin B1 receptor as shown as SEQ ID NOS:5-26 or SEQ ID NOS: 43-60 or directly to an amino acid residue of a peptidyl linker that is covalently fused to any of the peptide antagonists of the bradykinin B1 receptor as shown as SEQ ID NOS:5-26 or 43-60.

It will be appreciated that, since the vehicle and/or the target peptides may be multivalent, it is possible by the process of the invention to produce a variety of vehicle:peptide structures. By way of example, a univalent vehicle and a univalent peptide will produce a 1:1 conjugate; a bivalent peptide and a univalent vehicle may form conjugates wherein the peptide conjugates bear two vehicle moieties whereas a bivalent vehicle and a univalent peptide may produce species where two peptide entities are linked to a single vehicle moiety; use of higher-valent vehicles can lead to the formation of clusters of peptide entities bound to a single vehicle moiety whereas higher-valent peptides may become encrusted with a plurality of vehicle moieties. The peptide moieties may have more than one reactive group which will react with the activated vehicle and the possibility of forming complex structures must always be considered; when it is desired to form simple structures such as 1:1 adducts of vehicle and peptide, or to use bivalent vehicles to form peptide:vehicle:peptide adducts, it will be beneficial to use predetermined ratios of activated vehicle and peptide material, predetermined concentrations thereof and to conduct the reaction under predetermined conditions (such as duration, temperature, pH etc.) so as to form a proportion of the described product and then to separate the described product from the other reaction products. The reaction conditions, proportions and concentrations of the reagents can be obtained by relatively simple trial-and-error experiments which are within the ability of an ordinarily skilled artisan with appropriate scaling-up as necessary. Purification and separation of the products is similarly achieved by conventional techniques well known to those skilled in the art. How- Conventional PEGylations through the conjugation of mPEG-maleimide with thiol group of peptides and polypeptides having cysteine amino acid residues are run in phosphate buffer with or without organic solvent. The high solubility of PEGylated peptides and polypeptides and potential instability of the pyrrolidin-2,5-dione ring in water have hampered the application of this method to large scale production and purification of PEGylated peptides and proteins. Therefore, we disclose here a novel non-aqueous conditions for the conjugation of mPEG-maleimide with thiol group of peptides and polypeptides having cysteine residues. The novel process results in moderate to high yields of PEGylated peptides and polypeptides and combines the Michael addition and aminolysis into one-pot (Scheme 4). Both conditions result in direct isolation of PEGylated peptides and polypeptides through a precipitation.

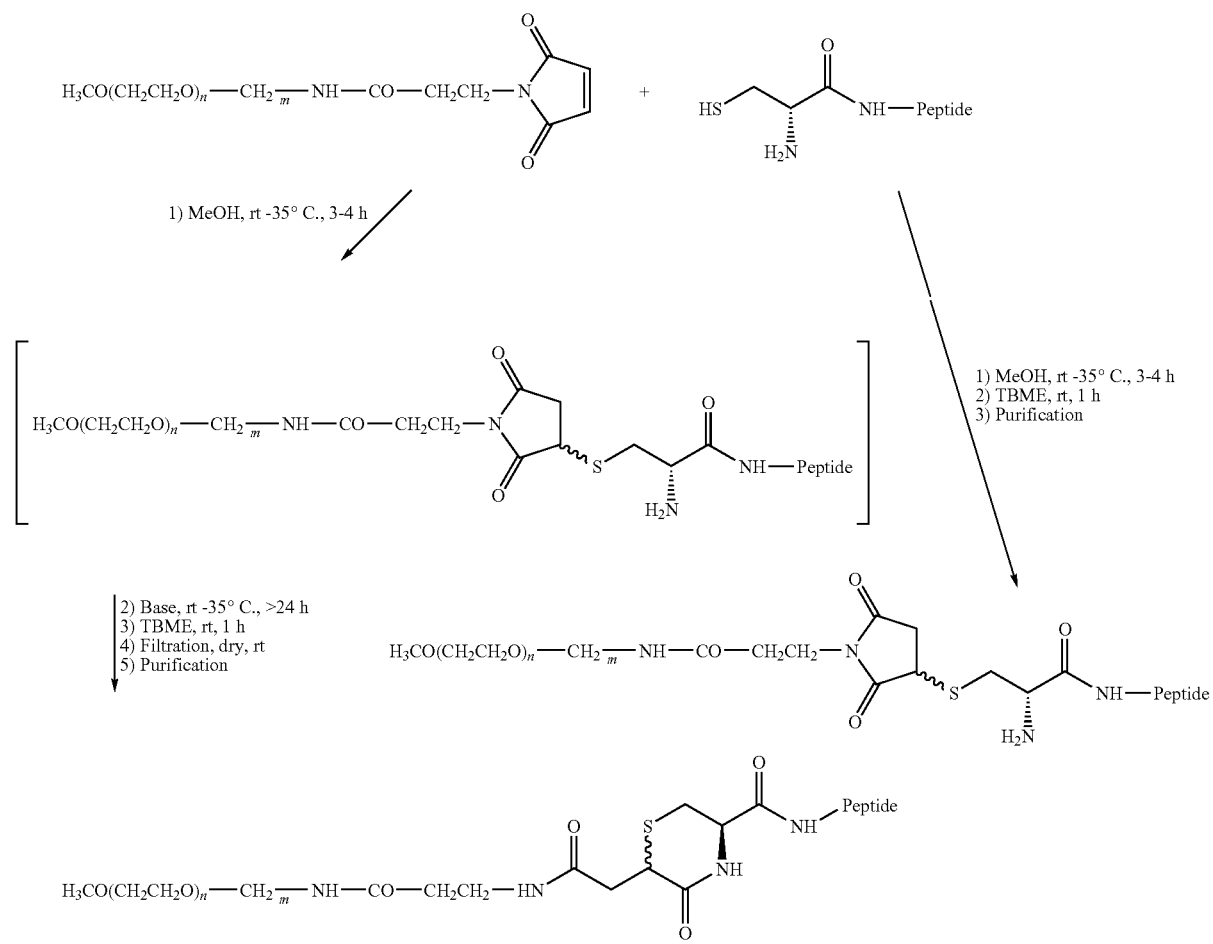

Scheme 4 ever, as used in the specification and the appended claims, the singular forms "a", "an", and "the" include plural referents unless the context clearly dictates otherwise. Thus, for example, reference to "a vehicle-conjugated peptide antagonist" or "a PEG-conjugated peptide antagonist" includes mixtures of such conjugates and reference to "the method of treatment" includes reference to one or more methods of treatment of the type which will be known to those skilled in the art or will become known to them upon reading this specification, and so forth.

In another embodiment of the process depicted in Scheme 4, in conjunction with any of the above or below embodiments, methanol (MeOH) may be substituted with a solvent comprising one or more of the following solvents: methanol, ethanol, isopropyl alcohol, n-propanol, n-butanol, dichloromethane (DCM), acetonitrile (AcN), tetrahydrofuran (THF), dimethylformamide (DMF), dimethylacetamide (DMAc), and N-methylpyrrolidone (NMP).

In another embodiment of the process depicted in Scheme 4, in conjunction with any of the above or below embodiments, TBME may be substituted with a solvent comprising one or more of the following solvents: diethyl ether, methyl isopropylether, and diisopropyl ether.

In another embodiment of the process depicted in Scheme 4, in conjunction with any of the above or below embodiments, reaction 1) as depicted in Scheme 4 may be conducted at a temperature of about 20° C. to about 60° C. Preferably, reaction 1) as depicted in Scheme 4 can be conducted at a temperature of about 30° C. to about 50° C. More preferably, reaction 1) as depicted in Scheme 4 can be conducted at a temperature of about 35° C to about 45° C. Most preferably, reaction 1) as depicted in Scheme 4 can be conducted at room temperature.

In another embodiment of the process depicted in Scheme 4, in conjunction with any of the above or below embodiments, reaction 2) as depicted in Scheme 4 may be conducted at a temperature of about 20° C. to about 60° C. Preferably, reaction 2) as depicted in Scheme 4 can be conducted at a temperature of about 30° C. to about 50° C. More preferably, reaction 1) as depicted in Scheme 4 can be conducted at a temperature of about 35° C. to about 45° C. Most preferably, reaction 2) as depicted in Scheme 4 can be conducted at room temperature.

In another embodiment of the process depicted in Scheme 4, in conjunction with any of the above or below embodiments, the precipitation reaction as depicted in Scheme 4 may be conducted for at least 10 minutes. More preferably, the precipitation reaction as depicted in Scheme 4 may be conducted for at least 60 minutes. Most preferably, the precipitation reaction as depicted in Scheme 4 is conducted for about 60 minutes.

In another embodiment of the process depicted in Scheme 4, in conjunction with any of the above or below embodiments, the precipitation, filtration, and/or purification reaction may be conducted more than once.

In another embodiment of the process depicted in Scheme 4, in conjunction with any of the above or below embodiments, the precipitation and/or purification reactions may be conducted more than once.

Partially protected peptides are especially useful reagents for this strategy as they enable selective modification of specific sites of polyfunctional peptides. The protecting groups are removed from the PEG conjugates using established deprotection methods well known by those skilled in the art of peptide synthesis. Partially protected peptides suitable for this application may be prepared using orthogonal protecting strategies well known to persons skilled in the art of peptide synthesis. An illustration of the synthesis of and conjugation of a partially protected peptide antagonist of the bradykinin B1 receptor is depicted in Scheme 5. Analogs in which side chain amines serve as sites of conjugation may be prepared from readily available orthogonally protected basic amino acids.

Scheme 5

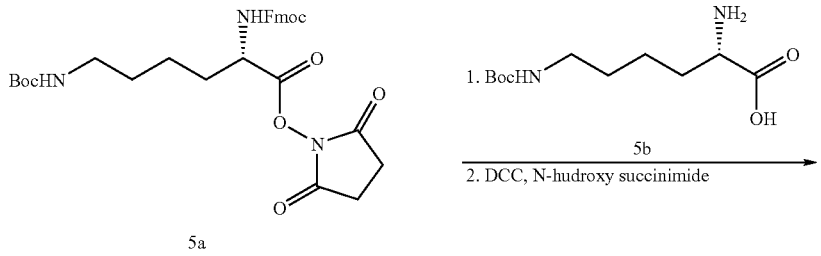

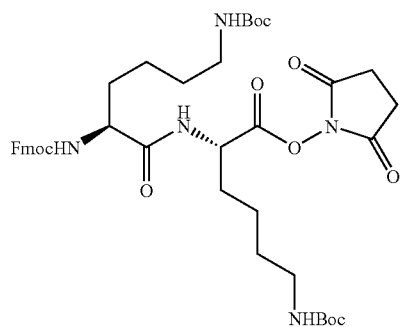

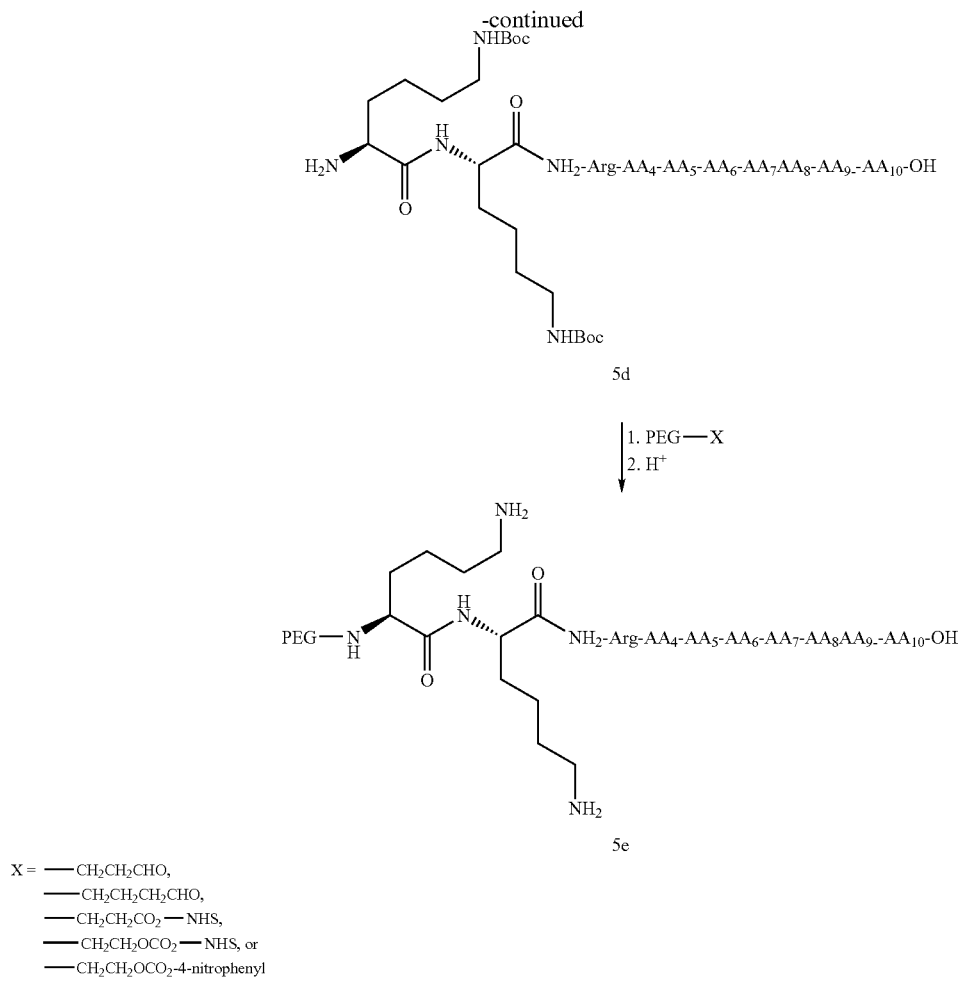

X = —CH$_2$CH$_2$CHO,
—CH$_2$CH$_2$CH$_2$CHO,
—CH$_2$CH$_2$CO$_2$—NHS,
—CH$_2$CH$_2$OCO$_2$—NHS, or
—CH$_2$CH$_2$OCO$_2$-4-nitrophenyl Partially protected forms of B1 antagonist peptides such as those listed in Table 3 (SEQ ID NOS:5-60) may be conjugated to PEG moieties using similar methods.

In one embodiment of the process depicted in Scheme 5, amine side chains of the partially protected peptides 5c are masked by tert-butylcarbamoyl (Boc) moieties and the resulting peptides are reacted with any of the previously described PEG aldehydes in an organics solvents such as 1,2-dichloroethane(DCE), N,N-dimethyl formamide(DMF) or mixtures thereof. The formation of the intermediate imine may be accelerated by the addition of a dehydrating agent such as powdered 4° A molecular sieves. After stirring at room temperature for 1-24 hours, the resulting imine is reduced by the addition of 1-4 equivalents of sodium triacetoxy borohydride or sodium cyanoborohydride.

In another embodiment of the process depicted in Scheme 5, in conjunction with any of the above or below embodiments, reactions with partially protected peptides such as 5c may be conducted at a temperature of about 20° C. to about 60° C. Preferably, reactions with partially protected peptides such as 5c as depicted in Scheme 5 can be conducted at a temperature of about 20° C. to about 50° C. More preferably, reactions with partially protected peptides such as 5c as depicted in Scheme 5 can be conducted at a temperature of about 35° C. to about 45° C. Most reactions with partially protected peptides such as 5c as depicted in Scheme 5 can be conducted at room temperature.

In another embodiment of the process depicted in Scheme 5, amine side chains of the partially protected peptides 5c are masked by tert-butylcarbamoyl (Boc) moieties and the resulting peptides are reacted with any of the previously described PEG N-hydroxysuccinimide or p-nitrophenyl ester PEG reagents in an organics solvents such as 1,2-dichloroethane (DCE), N,N-dimethyl formamide(DMF), dichloromethane, N-methylpyrolidine(NMP) or mixtures thereof. Activated PEG esters may be either monofunctional or linear bifunctional varieties both of which are commercially available from suppliers such as Nektar or NOF. In addition, branched polyfunctional PEG activated ester, containing 3-6 hydroxysuccinimide or p-nitrophenylester moieties are especially useful in preparing conjugates of the present invention.

In another embodiment of the process depicted in Scheme 5, in conjunction with any of the above or below embodiments, reactions with partially protected peptides such as 5c may be conducted at a temperature of about 20° C. to about 60° C. with reaction times ranging from about 4 hours to about 10 days. Preferably, reactions with partially protected peptides such as 5c as depicted in Scheme 5 can be conducted at a temperature of about 20° C. to about 50° C. with reaction times ranging from about 12 hours to about 5 days. More preferably, reactions with partially protected peptides such as 5c as depicted in Scheme 5 can be conducted at a temperature of about 35° C. to about 45° C. with reaction times ranging from about 1 to about 5 days. Most reactions with partially protected peptides such as 5c as depicted in Scheme 5 can be conducted at room temperature with reaction times ranging from about 1 to about 4 days.

In another embodiment of the process depicted in Scheme 5, in conjunction with any of the above or below embodiments, the removal of the side chain protecting groups as depicted in Scheme 5 may be conducted at a temperature of about −20° C. to about 60° C. This reaction may be performed in a compatible solvent such as dichloromethane using between about 5% trifluoroacetic acid (TFA) and 50% TFA by volume. Preferably, the acid mediated protecting group removal as depicted in Scheme 5 can be conducted at a temperature of about 0° C. to about 40° C., using about 10 to about 25% TFA by volume. More preferably, the acid mediated protecting group removal as depicted in Scheme 5 can be conducted at a temperature of about 0° C. to about 25° C. using about 10% to about 20% TFA by volume in dichloromethane. Most preferably, the acid mediated protecting group removal as depicted in Scheme 5 can be conducted at room temperature using about 20% by volume in dichloromethane.

In another embodiment of the process depicted in Scheme 5, in conjunction with any of the above or below embodiments, the products 5d depicted in Scheme 4 may be purified reverse phase HPLC, size exclusion chromatography, ion exchange chromatography or membrane dialysis. More preferably, a combination of two or more of the above mentioned purification techniques may be used either in combination or sequentially to afford purified conjugates of the present invention.

In another embodiment of the process depicted in Scheme 5, in conjunction with any of the above or below embodiments, the purification method may be conducted more than once.

Derivatives. Also contemplated herein are derivatives of the peptides and/or conjugated peptides of the present invention. Such derivatives may further improve the solubility, absorption, biological half-life, and the like, of the vehicle- or PEG-conjugated peptides disclosed herein. The added moieties may alternatively eliminate or attenuate any undesirable characteristic of the peptides and/or conjugated peptides disclosed herein. Exemplary derivatives include vehicle- or PEG-conjugated peptides in which:

1. The peptides and/or conjugated peptide or some portion thereof is cyclic. For example, the peptide portion of a peptide and/or conjugated peptide may be modified to contain two or more cysteine residues (e.g., in the peptidyl linker), which could cyclize by disulfide bond formation. For citations to references on the preparation of cyclized derivatives, see WO 00/24782.

2. The peptide and/or vehicle- or PEG-conjugated peptide is cross-linked or is rendered capable of cross-linking between molecules. For example, the peptide portion of a conjugated peptide may be modified to contain one Cys residue and thereby is able to form an intermolecular disulfide bond with a like molecule.

3. One or more peptidyl [—C(O)NR—] linkages (peptide bonds) is replaced by a non-peptidyl linkage. Exemplary non-peptidyl linkages are —CH$_2$-carbamate [—CH$_2$—OC(O)NR—], phosphonate, —CH$_2$-sulfonamide [—CH$_2$—S(O)$_2$NR—], urea [—NHC(O)NH—], —CH$_2$-secondary amine, and alkylated peptide [—C(O)NR$^6$— wherein R$^6$ is lower alkyl].

4. The N-terminal cysteine residue of a a conjugated peptide in X$^1$ may be substituted with a N-terminal derivative group. Exemplary N-terminal derivative groups include —NHR$^1$ where R$^1$ is monoalkyl.

Derivatization with bifunctional agents is useful for cross-linking the vehicle-conjugated peptides or their functional derivatives to a water-insoluble support matrix or to other macromolecular vehicles. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]-propioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate (oligosaccharide) groups may conveniently be attached to sites that are known to be glycosylation sites in proteins. Generally, O-linked oligosaccharides are attached to serine (Ser) or threonine (Thr) residues, while N-linked oligo-saccharides are attached to asparagine (Asn) residues when they are part of the sequence Asn-Aaa-Ser/Thr, where Aaa can be any amino acid except proline. Aaa is preferably one of the nineteen naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated conjugated peptide. Such site(s) may be incorporated in the linker of the vehicle-conjugated peptides of the invention. Such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in cysteine, methylation of the alpha-amino groups of lysine, arginine, and/or histidine side chains (Creighton, Proteins: Structure and Molecule Properties, W.H. Freeman & Co., San Francisco, pages 79-86. (1983)).

Unless otherwise disclosed herein, the synthesis of peptides and/or conjugated peptides described herein, including preparation of appropriate amino acid derivatives, their activation and coupling to form peptides and methods for purification of peptides and determination of their purity are included in the general body of knowledge of peptide chemistry, as generally described in Houben-Weyl "Methoden der Organischen Chemie" Vol. 16, parts I & II, (1974) for solution phase synthesis. For synthesis by the solid phase method, suitable techniques are also well known in the art, and include those described in Merrifield, Chem. Polypeptides, pages 335-361 (Katsoyannis and Panayotis editors) (1973); Merrifield, J. Am. Chem. Soc., Volume 85, page 2149 (1963); Davis et al., Biochem. Intl., Volume 10, pages 394-414 (1985); Stewart and Young, Solid Phase Peptide Synthesis (1969); U.S. Pat. No. 3,941,763; Finn et al., The Proteins (3d edition), Volume 2, pages 105-253 (1976); and Erickson et al., The Proteins (Third Edition), Volume 2, pages 257-527 (1976). A chemist skilled in the art of peptide synthesis would be able to synthesize the described peptides by standard solution methods or by manual or automatic solid phase methods. Solid phase synthesis is the preferred technique for making individual peptides because of its cost-effectiveness.

Pharmaceutical Compositions

In General. The present invention also provides methods of using pharmaceutical compositions of the inventive peptides and/or vehicle-conjugated peptides, e.g., in the prevention or treatment of inflammation and pain (including, but not limited to, inflammatory pain and associated hyperalgesia and allodynia). The peptides and/or vehicle-conjugated peptides of the invention also have therapeutic value for the prevention or treatment of other painful conditions associated with or mediated by B1 activation, including, but not limited to, thalamic pain syndrome, diabetes, toxins and chemotherapy, septic shock, arthritis, mixed-vascular and non-vascular syndromes, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, inflammatory bowel disease, dermatitis, myositis, neuritis, collagen vascular diseases, chronic inflammatory conditions, epithelial tissue damage or dysfunction, herpes simplex, diabetic neuropathy pain, post-herpetic neuralgia, causalgia, sympathetically maintained pain, deafferentation syndromes, tension headache, angina, migraine, surgical pain, disturbances of visceral motility at respiratory, genitourinary, gastrointestinal or vascular regions, wounds, burns, allergic rhinitis, asthma, allergic skin reactions, pruritis, vitiligo, general gastrointestinal disorders, colitis, gastric ulceration, duodenal ulcers, or vasomotor or allergic rhinitis.

The invention also provides for the use of the peptides and/or vehicle-conjugated peptides of the present invention for the prevention or treatment of acute pain, dental pain, back pain, lower back pain, pain from trauma, surgical pain, pain resulting from amputation or abscess, causalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, and bronchial disorders.

Accordingly, the present invention also relates to the use of one or more of the peptides and/or vehicle-conjugated peptides of the present invention in the manufacture of a medicament for the treatment of a disorder such as acute pain, dental pain, back pain, lower back pain, pain from trauma, surgical pain, pain resulting from amputation or abscess, causalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, and bronchial disorders.

As used herein, "treatment" or "treating" is an approach for obtaining beneficial or desired clinical results. For purposes of this invention, beneficial or desired clinical results include, but are not limited to, one or more of the following: improvement or alleviation of any aspect of pain and/or inflammation, including acute, chronic, inflammatory, neuropathic, or post-surgical pain. For purposes of this invention, beneficial or desired clinical results include, but are not limited to, one or more of the following: including lessening severity, alleviation of one or more symptoms associated with pain and/or inflammation including any aspect of pain and/or inflammation (such as shortening duration of pain and/or inflammation, and/or reduction of pain sensitivity or sensation).

Such pharmaceutical compositions or medicaments may be for administration by injection, or for oral, pulmonary, nasal, transdermal or other forms of administration. In general, the invention encompasses pharmaceutical compositions comprising effective amounts of at least one peptide and/or at least one vehicle-conjugated peptide of the invention (in amounts effective to prevent, ameliorate, or abolish pain or any of the other medical conditions provided herein) together with pharmaceutically acceptable diluents, excipients, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosol, benzyl alcohol) and bulking substances (e.g., lactose, mannitol); incorporation of the material into particulate preparations of polymeric vehicle-conjugated peptides such as polylactic acid, polyglycolic acid, etc. or into liposomes. Hyaluronic acid may also be used, and this may have the effect of promoting sustained duration in the circulation. Such compositions may further influence the physical state, stability, rate of in vivo release, and rate of in vivo clearance of the vehicle-conjugated peptides of the present invention. See, for example, Remington's Pharmaceutical Sciences, 18th Edition., Mack Publishing Co., Easton, Pa., pages 1435-1712 (1990), which is herein incorporated by reference. The compositions may be prepared in liquid form, or as a dried powder (such as lyophilized form). Implantable sustained release formulations are also contemplated, as are transdermal formulations.

Oral dosage forms. Contemplated for use herein are oral solid dosage forms, which are described generally in Chapter 89 of Remington's Pharmaceutical Sciences, above, which is herein incorporated by reference. Solid dosage forms include tablets, capsules, pills, troches or lozenges, cachets or pellets.

Also, liposomal or proteinoid encapsulation may be used to formulate the present compositions (such as, for example, the proteinoid microspheres reported in U.S. Pat. No. 4,925,673). Liposomal encapsulation may be used, and the liposomes may be derivatized with various polymers (see, for example, U.S. Pat. No. 5,013,556). A description of possible solid dosage forms is given in Chapter 10 of Marshall, K., Modern Pharmaceutics, edited by G. S. Banker and C. T. Rhodes (1979), herein incorporated by reference. In general, the formulation will include a vehicle-conjugated peptide of the invention, as well as inert ingredients which allow for protection against the stomach environment and release of the vehicle-conjugated peptide in the intestine.

Also specifically contemplated are oral dosage forms of the inventive peptides and/or vehicle-conjugated peptides themselves. In this regard, if necessary, the peptides and/or vehicle-conjugated peptides may be chemically modified so that oral delivery is efficacious. It is also possible to use a salt of a modified aliphatic amino acid, such as sodium N-(8-[2-hydroxybenzoyl]amino) caprylate (SNAC), as a carrier to enhance absorption of the vehicle-conjugated peptides of the invention. See U.S. Pat. No. 5,792,451, entitled "Oral Drug Delivery Composition and Methods".

The peptides and/or vehicle-conjugated peptides of the invention can be included in the formulation as fine multiparticulates in the form of granules or pellets of a particle size about one millimeter. The formulation of the material for capsule administration could also be as a powder, as lightly compressed plugs, or even as tablets. The therapeutic could be prepared by compression.

Colorants and flavoring agents may all be included. For example, the peptide and/or vehicle-conjugated peptide or any derivative thereof may be formulated (such as by liposome or microsphere encapsulation) and then further contained within an edible product, such as a refrigerated beverage containing colorants and flavoring agents.

One may dilute or increase the volume of the peptide and/or vehicle-conjugated peptide of the invention with an inert material. These diluents could include carbohydrates, especially, mannitol, α-lactose, anhydrous lactose, cellulose, sucrose, modified dextrans and starch. Certain inorganic salts may also be used as fillers, including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include, but are not limited to, starch, including the commercially available disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may also be used. Another form of the disintegrants are the insoluble cationic exchange resins. Powdered gums may be used as disintegrants and as binders, and these can include powdered gums such as agar, Karaya or tragacanth. Alginic acid and its sodium salt are also useful as disintegrants.

Binders may be used to hold the components of the pharmaceutical composition together to form a hard tablet, and they include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation to prevent sticking during the formulating process. Lubricants may be used as a layer between the therapeutic and the die wall, and these can include, but are not limited to: stearic acid, including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the vehicle-conjugated peptide during formulation and to aid rearrangement during compression might be added. Such glidants may include starch, talc, pyrogenic silica and hydrated silicoaluminate.

To aid dissolution of the peptide and/or vehicle-conjugated peptide of the invention into the aqueous environment, a surfactant might be added as a wetting agent. Such surfactants may include anionic detergents such as sodium lauryl sulfate, dioctyl sodium sulfosuccinate and dioctyl sodium sulfonate. Cationic detergents may be used and can include benzalkonium chloride or benzethonium chloride. The list of potential nonionic detergents that may be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants may be present in the formulation either alone or as a mixture in different ratios.

Additives may also be included in the formulation to enhance uptake of the peptides and/or vehicle-conjugated peptide. Additives potentially having this property include various fatty acids, such as, for instance, oleic acid, linoleic acid and linolenic acid.

Controlled release formulation may be desirable. The peptide and/or vehicle-conjugated peptide of the invention may be incorporated into an inert matrix which permits release by either diffusion or leaching mechanisms, for example, gums. Slowly degenerating matrices may also be incorporated into the formulation, for example, alginates or polysaccharides. Another form of a controlled release of the peptide and/or vehicle-conjugated peptide of the invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Pulmonary delivery forms. Also contemplated herein is pulmonary delivery of a pharmaceutical composition in accordance with the invention. The peptide and/or vehicle-conjugated peptide (or derivatives thereof) is delivered to the lungs of a mammal while inhaling and traverses across the lung epithelial lining to the blood stream. Reports relating to the pulmonary delivery of macromolecules that may be helpful in this regard include Adjei et al., Pharma. Res., Volume 7, pages 565-569 (1990); Adjei et al., Internatl. J. Pharmaceutics, Volume 63, pages 135-144 (1990) (leuprolide acetate); Braquet et al., J. Cardiovasc. Pharmacol., Volume 13 (suppl. 5), s. 143-146 (1989) (endothelin-1); Hubbard et al., Annals Int. Med., Volume 3, pages 206-12 (1989) (α1-antitrypsin); Smith et al., J. Clin. Invest., Volume 84, pages 1145-1146 (1989) (α1-proteinase); Oswein et al., "Aerosolization of Proteins", Proc. Symp. Resp. Drug Delivery II, Keystone, Colo. (1990) (recombinant human growth hormone); Debs et al., J. Immunol., Volume 140, pages 3482-3488 (1988) (interferon-γ and tumor necrosis factor α); and U.S. Pat. No. 5,284,656 (granulocyte colony stimulating factor).

Contemplated for use in the practice of the invention are a wide range of mechanical devices designed for the pulmonary delivery of therapeutic products, including but not limited to nebulizers, metered dose inhalers, and powder inhalers, all of which are familiar to those skilled in the art. Some specific examples of commercially available devices suitable for the practice of the invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the herein described peptides and/or vehicle-conjugated peptides and/or derivatives thereof. Typically, each formulation is specific to the type of device employed and may involve the use of an appropriate propellant material, in addition to diluents, excipients adjuvants and/or carriers useful in therapy.

Pharmaceutically acceptable carriers for these pulmonary compositions include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the peptide). Dextrans, such as cyclodextran, bile salts, cellulose and cellulose derivatives may also be used. Amino acids may be used, such as in a buffer formulation.

In addition, the use of liposomes, microcapsules or microspheres, inclusion complexes, or other types of carriers is contemplated.

Formulations suitable for use with a nebulizer, either jet or ultrasonic type, will typically comprise the described peptide and/or vehicle-conjugated peptide dissolved in water at a concentration of about 0.1 to 25 milligrams (mg) of biologically active agent per milliliter (ml) of solution. The formulation may also include a buffer and a simple sugar (e.g., for peptide stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the described peptide and/or vehicle-conjugated peptide suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the described peptides and/or vehicle-conjugated peptides and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery forms. Nasal delivery of the peptide and/or vehicle-conjugated peptides is also contemplated. Nasal delivery allows the passage of the peptide and/or vehicle-conjugated peptides of the invention to the blood stream directly after administering the therapeutic product to the nose, without the necessity for deposition of the product in the lung. Formulations for nasal delivery include those with dextran or cyclodextran. Delivery via transport across other mucous membranes is also contemplated.

Pump delivery. In certain embodiments of the present invention, localized delivery of the peptides and/or conjugated peptides of the present invention is contemplated for treating or preventing B1 mediated disorders. One method of localized delivery contemplated by the invention is injection of the agent at a local site at which the agent acts.

Another method for localized delivery includes inserting a catheter to direct the drug(s) to the desired body site, and using a pump to impel a drug(s) through the catheter. Externally worn drug pumps used with an internally implanted catheter are well known to those skilled in the art.

Yet another method for localized delivery includes implantable drug delivery devices. Implantable pumps have been developed to address the disadvantages of techniques that use external pump and catheter systems are are well-known to those skilled in the art. Implantable drug delivery pumps often include a reservoir for storing the drug, an injection port to enable injection of fresh drug preparations as well removal of old drug at regular intervals from the reservoir, and optionally a catheter for delivering the drug to the desired site. Preferred implantable devices include, but are not limited to, the Duros implant (Alza Corporation, Mountain View, Calif.), the SynchroMed I or II Infusion System (Medtronic, Inc., Minneapolis) and the like.

Additionally (or alternatively), the present invention provides peptides and/or conjugated peptides for use in any of the various slow or sustained release formulations or microparticle formulations previously mentioned hereinabove and/or known to the skilled artisan.

Dosages. Effective dosages of the peptides and/or conjugated peptides of the invention to be administered may be determined through procedures well known to those in the art which address such parameters as biological half-life, bioavailability, and toxicity. In preferred embodiments, an effective dosage range is determined by one skilled in the art using data from routine in vitro and in vivo studies well known to those skilled in the art. For example, in vitro cell culture assays, such as the exemplary assays described in Example 6 below will provide data from which one skilled in the art may readily determine the mean inhibitory concentration (IC) or mean effective concentration (EC) of the peptide or the conjugated peptide necessary to block some amount of B1 induced activity (e.g., 50%, $IC_{50}$; or 90%, $IC_{90}$). Appropriate doses can then be selected by one skilled in the art using pharmacokinetic data from one or more routine animal models, such as the exemplary pharmacokinetic data described in Example 9, below, so that a minimum plasma concentration ($C_{min}$) of the peptide is obtained which is equal to or exceeds the determined IC value. The dosage regimen involved in a method for treating the involved disease or disorder will be determined by the attending physician, considering various factors which modify the action of therapeutic agents, such as the age, condition, body weight, sex and diet of the patient, the severity of the condition being treated, time of administration, and other clinical factors. Generally, the daily regimen should be in the range of 1.0-10000 micrograms (μg) of the peptide and/or vehicle-conjugated peptide per kilogram (kg) of body weight, preferably 1.0-1000 μg per kilogram of body weight, and most preferably 1.0-150 μg per kilogram of body weight.

Combination Therapy. In another aspect, the present invention includes a method for treating (or, in other embodiments, preventing) pain and/or inflammation, or any condition or disorder associated with B1 activation, comprising administering an amount of peptide and/or conjugated peptide of the present invention and an amount of an NSAID. The term "NSAID" refers to a non-steroidal anti-inflammatory compound. The relative amounts and ratios of peptide antagonist and/or conjugated peptide antagonist and NSAID may vary. In some embodiments, enough of the peptide(s) and/or conjugated peptide(s) will be administered so as to allow reduction of the normal dose of NSAID required to effect the same degree of pain or inflammation amelioration. In some embodiments, enough of a peptide(s) and/or conjugated peptide(s) of the present invention will be administered so as to allow reduction of the normal dose of NSAID required to effect the same degree of pain or inflammation amelioration by at least about 5%, at least about 10%, at least about 20%, at least about 30%, at least about 40%, at least about 50%, at least about 60%, at least about 70%, at least about 80%, or at least about 90%, or more. This reduction may be reflected in terms of amount administered at a given administration and/or amount administered over a given period of time (reduced frequency).

In another aspect, the invention provides methods for enhancing NSAID pain or inflammation treatment comprising administering an effective amount of an NSAID in conjunction with an effective amount of at least one peptide and/or at least one conjugated peptide of the present invention. As used herein, "administration in conjunction" is also meant to encompass any circumstance wherein an NSAID and a peptide and/or conjugated peptide of the present invention are administered in an effective amount to an individual. "Administration in conjunction", as used herein, comprises simultaneous administration and/or administration at different times. Administration in conjunction also encompasses administration as a co-formulation (i.e., the peptide and/or conjugated peptide of the present invention and NSAID are present (combined) in the same composition) and/or administration as separate compositions. It is understood that the peptide(s) and/or conjugated peptide(s) of the present invention and at least one NSAID can be administered at different dosing frequencies and/or intervals. For example, a conjugated peptide of the present invention may be administered weekly, while an NSAID can be administered more frequently. It is understood that the peptide(s) and/or conjugated peptide(s) of the present invention and the NSAID can be administered using the same route of administration or different routes of administration, and that different dosing regimens may change over the course of administration(s). Administration may even be before the onset of pain or inflammation. Therefore, in another aspect, the invention provides methods for treating, reducing incidence of, palliating and/or delaying the development or progression of pain and/or inflammation in an individual, said methods comprising administering an effective amount of at least one peptide and/or at least one conjugated peptide of the present invention in conjunction with an effective amount of at least one NSAID. Such methods include treating or preventing any pain and/or inflammation of any etiology, including pain and/or inflammation where the use of an NSAID is generally prescribed. Such methods are also suitable for treating or preventing any condition or disorder previously mentioned hereinabove or hereinbelow as being mediated by or associated with B1 activation. In some embodiments, the pain and/or inflammation is post-surgical pain. In some embodiments, the pain and/or inflammation is associated with burns or wounds. In other embodiments, the pain and/or inflammation is associated with rheumatoid arthritis. In other embodiments, the pain and/or inflammation is associated with osteoarthritis. In other embodiments, the pain and/or inflammation is associated with post-herpetic neuralgia. In some embodiments, the NSAID is selected from the group consisting of aspirin, acetaminophen, ibuprofen, indomethacin, naproxen, naprosyn, diclofenac, ketoprofen, tolmetin, slindac, mefenamic acid, meclofenamic acid, diflunisal, Rufenisal, piroxim, sudoxicam, isoxicam, celecoxib, rofecoxib, DUP-697, flosulide, meloxicam, 6methoxy-2 naphthylacetic acid, MK-966, nabumetone, nimesulide, NS-398, SC-5766, SC58215, T-614, or combinations thereof.

EXAMPLES

The following Examples are presented for illustrative purposes only and are not intended, nor should they be construed, as limiting the invention in any manner. Those skilled in the art will appreciate that modifications and variations of the compounds disclosed herein can be made without violating the spirit or scope of the present invention. Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Example 1

Synthesis and Purification of B1 Receptor Peptide Antagonists and PEG-Conjugated B1 Receptor Peptide Antagonists Various peptides of the invention were synthesized using synthesis techniques well-known in the art. A preferred method of synthesizing various peptides of the invention uses a FMOC strategy with carbodiimide activation as described below.

Part 1: Dissolve Fmoc-amino acid to resin using carbodiimide chemistry.

Fmoc-amino acid (3-4 equivalent) was dissolved in dry DCM/NMP mixture (NMP or DMF was used to aid complete dissolution). A solution of N-hydroxybenzotriazole (HOBt, same equivalent to amino acid) in NMP was added to the amino acid solution. A solution of N,N'-dicyclohexylcarbodiimide (DCC, same equivalent to amino acid) in DCM was added to the amino acid solution. The solution was mixed for approximately 20 minutes. The activated acid solution was then added to resin (if needed, precipitates were removed prior to addition). The reaction was agitated until the resin was negative by the ninhydrin test. Upon completion of the coupling, the resin was collected and washed with DMF several times.

Part 2: Remove N-terminal Fmoc from peptide-resin.

Fmoc-protected peptidyl resin was treated with piperidine/DMF (2/8) for 3 minutes. The resin was drained and treatment was repeated for 15 min. The resin was washed with DMF and then DCM several times. The resin was air-dried if the next step involved cleavage of the peptide from the resin as described in step 3.

Part 3: TFA cleavage and deprotection.

The dried resin from Part 2 was placed in a flask and 10-25 ml/g resin of cleavage cocktail (95% TFA, 2.5% water, 1.5% triisopropylsilane and 1% ethanedithiol) was added. After stirring the reaction for 3-4 hours, the resin was removed by filtration under reduced pressure and washed twice with TFA.

The combined filtrates were concentrated to ~20% by rotary evaporation under reduced pressure. The liquid was cooled to −50° C., and precipitate with 10-fold volume of cold dry ether. The precipitate was collected. The peptide was then dissolved in a water/acetonitrile mixture containing 0.5% TFA and lyophilize. The crude product was then purified using C18 HPLC, on a gradient from 10% acetonitrile/0.1% TFA in water to 50% acetonitrile/0.1% TFA in water. For 1 g of crude product, a 250×50 mm C18 column was used at a flow rate of 90 mL/min on an Agilent prep HPLC with dual wavelength detection at 215 and 254 nm. The injection was fractionated and each fraction analyzed by mass spectrometry. Tubes were pooled based on mass spec, concentrated under reduced pressure to remove acetonitrile, and lyophilized to obtain the peptide B1 antagonists as white powders. Characterization was accomplished by HPLC-MS and Maldi-TOF mass determination.

Various PEG-conjugated peptides of the invention were prepared as follows.

Various active bradykinin B1 receptor peptide antagonists selected from the group consisting of SEQ ID NOS:5-60) were synthesized with different peptidyl linkers at the N-terminus, and each containing a penultimate cysteine using the aforementioned methods (e.g., SEQ ID NOS:27-41). These peptide analogs were derivatized with different sizes and configurations of poly(ethylene glycol) (PEG) through site-directed coupling of the maleimide activated polymer to the N-terminal cysteine thiol of the peptide analogs using, for example, Method A or Method B described below. The resultant PEG-peptide conjugates were purified by ion exchange chromatography, concentrated by lyophilization or diafiltration and dialyzed into buffer prior to in vitro and in vivo bioassay.

Method A:

PEG-conjugated peptides were prepared by reacting a cysteine containing peptide with PEG-maleimide in 50 mM NaHPO$_4$, 5 mM EDTA, pH 6.5 at 2.5-5 mg/ml peptide and a reaction stoichiometry of 1.2-fold molar excess of maleimide:thiol. The reaction was stirred at room temperature (20-25 ° C.) for 1-1.5 hr. Once complete, the reaction was quenched with a 10-fold molar excess of β-mercaptoethanol (β-ME):maleimide and allowed to stir an additional 30-60 minutes at room temperature.

Progress of the reaction was monitored using reverse-phase HPLC (RP-HPLC) by injection of 5 µl of the reaction to a 4.6×250 mm, 5 micron C4 column (Grace Vydac, Columbia, Md.; cat. no.: #214TP54). The unreacted peptide and PEG-peptide conjugate are eluted with a linear 5-90% acetonitrile gradient in 0.1% trifluoroacetic acid. Typically, >90% of the peptide analog is consumed in the reaction.

Linear maleimide activated PEG polymers (MW=5 kD or 20 kD, PD=1.01-1.02) were provided by Shearwater Corp. or NOF Corp, (Toyko, Japan).

Purification:

The PEG-conjugated peptides were purified by cation exchange chromatography using SP Sepharose HP columns (Amersham Biosciences) pre-equilibrated with 10 mM NaOAc, 20% EtOH, pH 4. Prior to loading, the reaction mixtures were diluted 10-fold with 20% EtOH and the pH adjusted to 3.5 with glacial acetic acid. The diluted reaction mixtures were loaded to an appropriate sized column such that a peptide:resin ration of 2.5 mg/ml was not exceeded.

The column was then washed with 2 column volumes (CVs) of 10 mM NaOAc, 20% EtOH, pH 4 and eluted with a linear 0-200 mM NaCl gradient in 10 mM NaOAc, 20% EtOH, pH 4 over 10-20 CV. The unmodified peptide and PEG-peptide conjugate were detected by monitoring absorbance at either 254 nm or 220 nm. Under these conditions, the excess PEG and β-ME were washed out in the unbound flow-through fraction, the conjugate eluted in a broad peak starting ~50 mM NaCl and the free peptide was well resolved, eluting at ~200 mM NaCl.

The eluted peak fractions were evaluated by RP-HPLC and pooled based on homogeneity and retention times consistent with PEG-peptide conjugate. The pooled conjugate peak was concentrated by drying, then reconstituted in water and dialyzed against buffer. Alternatively diafiltration may be used to concentrate and buffer exchange the conjugate.

The final pools of PEG-peptide conjugates were analyzed by RP-HPLC and were typically ~98% conjugate. Conjugate composition and concentrations were determined by a combination of amino acid analyses, peptide sequencing, and absorbance spectroscopy.

The solution stability of compounds represented by 1c in Scheme 1 was monitored at ambient temperature in pH=7.2 phosphate buffered saline (PBS) over time using the CEX method described above (FIG. 1(A)). Compound 1c was shown to rapidly convert to 1d as well as to two products resulting from hydrolysis of the succinimide moiety (structures determined by a combination of IR, MS/MS and NMR experiments).

Method B:

mPEG-maleimide (1.0 eq.) was dissolved at 30° C. in anhydrous MeOH in a 3-necked round bottom flask equipped with a mechanical stirrer, temperature probe, and a N$_2$ inlet. Upon total dissolution of mPEG-maleimide, a peptide containing a N-terminal cysteine residue (1.3 eq.) was added into the clear solution and stirred at rt for 3 h. Reverse phase HPLC shows disappearance of mPEG-maleimide and new peak for the initial 3-sulfanyl-succinimide adduct. Next, ten equivalents of diisopropyl-ethylamine (Sigma-Aldrich Corp., St. Louis, Mo.) was added into the solution and stirred at 25° C. for at least 24 hours. The reaction was monitored by ion exchange chromatography using TOSOHAAS SP-5PW (20 µm) as stationary phase. CEX analysis indicated over 98% conversion with less 1.5% of the 3-sulfanyl-succinimide adduct remaining. Tertiary butyl methyl ether (TBME) was added (twice the volume methanol used in the reaction) and the resulting cloudy solution was stirred at room temperature for 1 hour. The white precipitate was filtered off and dried under vacuum at room temperature overnight to afford the crude 6-methyl-carbamoyl-5-oxo-thiomorpholine-3-carboxamide linked product (1d).

Purification:

The above crude product was purified by RP-HPLC using MeOH—H$_2$O—AcOH system (c18 YMC ODS NQ as stationary phase) to afford the 6-methyl-carbamoyl-5-oxo-thiomorpholine-3-carboxamide linked product with a purity >98% by analytical reverse phase chromatography. The pure fractions were combined and concentrated to dryness under vacuum and the resulting white residue was dissolved the minimum amount of warm MeOH (~30° C.) sufficient to give a clear solution then treated with TBME (twice the volume of MeOH used). The resulting cloudy solution was stirred at room temperature for 1 hour and precipitate was filtered off, dried under vacuum at room temperature for at least 16 hours. Pure product (1d) is obtained as an off-white in 74% overall yield with >98% CEX and RPC purity. Conjugate composition and peptide content were determined by a combination of amino acid analyses, peptide sequencing, multinuclear NMR methods and absorbance spectroscopy. The solution stability of compound 1d was monitored at ambient temperature in pH=7 phosphate buffered saline (PBS) was monitored over time using the CEX method described above. This compound proved significantly more stabile, with no significant changes noted over six days.

Analytical reverse phase (RP) and cation exchange (CEX) chromatography was performed on Agilent 1100 HPLC systems with diode array or variable wavelength detector and thermostatted autosampler. Standard chromatographic conditions are outlined below.

1. RP-HPLC Method Conditions

| | |
|---|---|
| Column: | YMC ODS-AQ, 3 µm, 120 Å, 4.6 × 100 mm |
| Column Temp. | 40° C. |
| Mobile Phases: | A) 0.1% TFA in water |
| | B) 0.1% TFA in MeOH |
| Flow rate: | 1.1 mL/min |
| Gradient: | Time % B |
| | 0 5 |
| | 10 40 |
| | 30 95 |
| | 35 95 |
| | 35.1 5 |
| | 40 5 |
| Detection: | UV at 220 nm |
| Injection volume: | 20 µL or 50 µL depending on the sample concentration |
| Sample concentration: | 2.5 to 10 mg/mL |
| Sample diluent: | Dulbecco's PBS and other buffers used in the stability studies |

2. General Analytical Cation Exchange Chromatographic Method

| | |
|---|---|
| Column: | TOSOH, TSK-GEL, SP-5PW, 10 µm, 7.5 × 75 mm |
| Column Temp. | 25° C. |
| Mobile Phases: | A) 20 mM $NaH_2PO_4$ in water/EtOH (8:2), pH 3.5 |
| | B) 20 mM $NaH_2PO_4$ and 0.5 M NaCl in water/EtOH (8:2), pH 3.5 |
| Flow rate: | 1.0 mL/min |
| Gradient: | Time B % |
| | 0 0 |
| | 3 0 |
| | 25 45 |
| | 40 100 |
| | 45 100 |
| | 45.1 0 |
| | 50 0 |
| Detection: | UV at 220 nm |
| Injection volume: | 10 to 50 µL depending on the sample concentration |
| Sample concentration: | 2.5 to 10 mg/mL |
| Sample diluent: | Dulbecco's PBS and other buffers used in the stability studies |

Example 2

Synthesis and Purification of PEG-Conjugated B1 Receptor Peptide Antagonists Using PEG Thioesters PEG-conjugated peptides were prepared by reacting a cysteine containing peptide with PEG-maleimide in 50 mM $NaHPO_4$, 5 mM EDTA, pH 7 at 2.5-5 mg/ml peptide and a reaction stoichiometry of 1.2-fold molar excess of maleimide:thiol. The reaction was stirred at room temperature (20-25° C.) for 18-26 hours. Once complete, the reaction is quenched with a 10-fold molar excess of β-mercaptoethanol (β-ME):maleimide and allowed to stir an additional 30-60 minutes at room temperature. The reactions were purified as described for Method A in Example 1 above.

Example 3

Synthesis and Purification of PEG-Conjugated B1 Receptor Peptide Antagonists Using PEG Thioesters or Iodoacetates PEG-conjugated peptides were prepared by reacting peptide containing a N-terminal cysteine residue with PEG-OPTE (ortho-pyridyl thio ester) in 50 mM $NaHPO_4$, 5 mM EDTA, pH 7 at 2.5-5 mg/ml peptide and a reaction stoichiometry of 1.2-fold molar excess of activated PEG:peptide. The reaction was stirred at room temperature (20-25° C.) for 18-26 hr. Once complete, the reaction is quenched with a 10-fold molar excess of cysteine:excess PEG reagent and allowed to stir an additional 30-60 minutes at room temperature. The reactions were purified as described in Method A of Example 1 above.

Alternatively, PEG-iodoacetamide may be used as described above to form conjugates in which the PEG moiety is attached via a thioether linkage (Scheme 3). In this case 1.5 molar equivalents of the activated PEG reaction is used and the reaction time is increased to 24 hours the reaction is quenched w/10 molar equivalents of β-mercaptoethanol purified as described in the examples above.

Example 4

Synthesis and Purification of PEG-Conjugated B1 Receptor Peptide Antagonists Using PEG propionaldehyde B1 receptor peptide antagonists such as any one of SEQ ID NOS:5-60 and 27-41 can be selectively N-terminally modified with PEG using the method described in U.S. Pat. No. 5,824,784 (which is hereby incorporated by reference in its entirety). For example, the peptide as shown in SEQ ID NO:6 (245 mg, 0.14 mmol) was dissolved in 10 mL of solution containing 100 mM $NaH_2PO_4$ and 60 mM $NaCNBH_3$. The mixture was cooled to 4° C. with over stirring and treated with 2.35 g of 20K mPEG porpionaldehyde (Nektar Therapuetics, Huntsville, Ala.). The mixture was stirred for 3 days, then purified by RP and CEX chromatography as described in Method B of Example 1.

Alternatively PEGs containing amine reactive functionalities may be reacted with partially protected B1 peptide antagonists according to the methods illustrated in Scheme 5. Following the conjugation reaction, the side chain protecting groups are cleaved using methods well known by those skilled in the art of solid and solution phase peptide synthesis, and the resulting PEG-peptide constructs purified as described above. Multifunctional PEG aldehydes (3-6 reactive groups) may also be reacted with excess molar amounts of protected peptides to afford multivalent PEG constructs in which multiple peptides are attached in a regiochemically and stoichiometrically defined manner.

Example 5

Synthesis and Purification of PEG-Conjugated B1 Receptor Peptide Antagonists Using PEG N hydroxy-succinimides B1 receptor peptide antagonists such as any one of SEQ ID NOS:5-60 may be selectively pegylated on a specific N terminal or side chain nitrogen atom using partially protected B1 peptide antagonists according to the methods illustrated in Scheme 5. For example a solution of partially decapeptide (1.43 g, 1.025 mmol) in 2.5 ml of anhydrous DMF was combined with 3.5 g (0.18 mmol) of Sunbright PTE-200GS (20 kD 4-arm succinimidylgluterate, NOF, Tokyo, Japan) and 1.0 mL of diisopropylethyl amine in 25 mL of dichloromethane. The resulting colorless solution was stirred at room temperature for 2 days then evaporated at reduced pressure. The resulting residue was dissolved in 25 mL of deionized water and placed in a 10,000 MW cutoff dialysis membrane (Pierce, Rockford Ill., USA). The compound was dialyzed against water for 24 hours (3 buffer changes), then lyophilized to afford the protected tetravalent PEG product. The resulting white solid was dissolved in 60 mL dichloromethane and treated with 20 mL of anhydrous TFA. After stirring at room temperature for 2 days the reaction mixture was evaporated at reduced pressure then dissolved in dialyzed as above. The dialyzed material was lyophilized then purified by ion exchange chromatography as previously described to afford the tetravalent product as a white solid. In a similar fashion PEGs containing 1-6 succinimidylgluterate moieties may be used to prepare mono or polyfunctional peptide constructs.

TABLE 4a $X^1$ Peptides

| SEQ ID NO: | Sequence of $X^1$ Peptide |
|---|---|
| 27 | {N} CGGGKRPPGFSPL {C} |
| 28 | {N} CGGGGGKRPPGFSPL {C} |
| 29 | {N} CGGGGGKKRPGFSPL {C} |
| 30 | {N} CGGGGGKRKRPPGFSPL {C} |
| 31 | {N} CG–CH2–CH2–CH2–CH2–CH2–CH2–KRPPGFSPL {C} |
| 32 | {N} CGGGGGKKRPPG[AMeF]S[D-β-Nal]I {C} |
| 33 | {N}CGGGGGKKRP[Hyp]G[Cpg]S[DTic][Cpg]{C} |
| 34 | {N}CGGGGGGGKKRP[Hyp]G[Cpg]S[DTic][CPG] {C} |
| 35 | {N} ac-CGGGGGKKRP[Hyp]G[Cpg]S[DTic][Cpg]{C} |
| 36 | {N}KKRP[Hyp]G[Cpg]S[DTic][Cpg] {C} |
| 37 | {N}acyl-KKRP[Hyp]G[Cpg]S[DTic][Cpg] {C} |
| 38 | {N} CKRPPGFSPL {C} |
| 39 | {N}CGGGGG[DOrn]KRP[Hyp]G[Cpg]S[DTic][Cpg]{C} |
| 40 | {N}CGGGGG[DOrn]KRP[Thz]G[Cpg]S[DTic][Cpg]{C} |
| 41 | {N}CGGGGGK[DOrn]RP[Hyp]G[Cpg]S[DTic][Cpg]{C} |

TABLE 4b $Y^1$ Peptides

| SEQ ID NO: | Sequence of $Y^1$ Peptide |
|---|---|
| 42 | {N} GGGGGKKRPPGFSPL {C} |

Example 6

In Vitro B1-Inhibition Activity of Peptide PEG-conjugated Peptide Antagonists of B1 Activity Peptides and/or conjugated peptides capable of selectively inhibiting B1 activity as compared to B2 activity were identified using assays such as those described in Sections A, B, and C below.

A. In Vitro Assay of Human B1 Receptor Function Using Calcium Flux:

Activation of the $G_q$ linked B1 receptor results in an increase in intracellular calcium. The calcium sensitive photoprotein aequorin can, therefore, be used as an indicator of B1 receptor activation. Aequorin is a 21-kDa photoprotein that forms a bioluminescent complex when linked to the chromophore cofactor coelenterazine. Following the binding of calcium to this complex, an oxidation reaction of coelenterazine results in the production of apoaequorin, coelenteramide, $CO_2$, and light that can be detected by conventional luminometry A stable CHO D-/human B1 receptor (GenBank Accession no. AJ238044)/Aequorin cell line was established and the cells were maintained in suspension in spinner bottles containing a 1:1 ratio of DMEM and HAM F12 (Gibco 11765-047), high glucose (Gibco 11965-084), 10% Heat Inactivated Dialyzed serum (Gibco 26300-061), 1× Non-Essential Amino Acids (Gibco 11140-050), 1× Glutamine-Pen-Strep (Gibco 10378-016), and Hygromycin, 300 µg/ml (Roche 843555). Fifteen to twenty four hours prior to the luminometer assay, 25,000 cells/well (2.5E6 cells/10 ml/plate) are plated in 96-well black-sided clear bottom assay plates (Costar #3904).

Media is removed from the wells and replaced with 60 µl of serum free HAM's F12 with 30 mM HEPES (pH 7.5) and 15 µM coelenterazine (Coelenterazine h Luciferin #90608; Assay Designs (Ann Arbor, Mich.). The plates are then incubated for 1.5-2 hours. Ten point $IC_{50}$ compound plates containing 1:3 or 1:5 dilutions of antagonist compounds and an agonist activator plate (20 nM des-Arg10-Kallidin final concentration, $EC_{80}$) are prepared using Ham's F12 with 30 mM HEPES, pH 7.5. Following coelenterazine incubation, an automated flash-luminometer platform is used to dispense the B1 antagonist compounds to the cell plate, a CCD camera situated underneath the cell plate takes 12 images of the cell plate at 5 second intervals to determine if there is any agonist activity with the compounds. The hB1 agonist, des-Arg$_{10}$-Kallidin, is then added to the cell plate and another 12 images are recorded to determine the $IC_{50}$ of the antagonist(s).

B. In Vitro Assay of hB2 Receptor Function Using Calcium Flux:

The intracellular calcium flux induced by hB2 receptor activation is analyzed using a hB2 recombinant cell line (CHO-K1) purchased from PerkinElmer (Wellesley, Mass.; catalog no.: RBHB2C000EA) on a fluorometric imaging plate reader (FLIPR). The cells are cultured in T225 flask containing Ham's F12 Nutrient Mixture (Invitrogen Corp., Carlsbad, Calif.; catalog no.: 11765-047), 10% Fetal Clone II Bovine Serum (HyClone, Logan, Utah; catalog no.: SH3006603), 1 mM Sodium pyruvate (100 mM stock, Invitrogen Corp., catalog no.: 12454-013), and 0.4 mg/ml Geneticin (G418; 50 mg/ml active geneticin, Invitrogen, catalog no.: 10131-207). Culture medium is changed every other day. 24 hrs prior to the FLIPR assay, the hB2/CHO cells are washed once with PBS (Invitrogen) and 10 ml of Versene (1:5000, Invitrogen, catalog no.: 15040-066) is added to each flask. After a 5 minute incubation at 37° C., Versene is removed and cells are detached from the flask and resuspended in culture medium. Cells are counted and 25,000 cells/well are plated in 96-well black-sided clear bottom assay plates (Costar, Acton, Mass.; catalog no.: 3904). Cells are incubated in a 37° C. $CO_2$ incubator overnight.

The media is aspirated from the cells and replaced with 65 µl of dye-loading buffer. The loading buffer is prepared by diluting a stock solution of 0.5 mM Fluo-4 AM (Molecular Probes, Eugene, Oreg.) dissolved in DMSO containing 10% [w/v] pluronic acid to a concentration of 1 µM in Clear Dulbecco's Modified Eagle Medium (DMEM) containing 0.1% BSA, 20 mM HEPES, and 2.5 mM probenecid (probenecid inhibits activity of the anion transport protein, and thus improves dye loading in the cells). The cells are dye-loaded for 1 hour at room temperature. The excess dye is removed by washing the cells two times with assay buffer. The assay buffer consists of Hank's Balanced Salt Solution (HBSS) containing 20 mM HEPES, 0.1% BSA, and 2.5 mM probenecid. After the wash cycles, a volume of 100 µL is left in each well, and the plate is ready to be assayed in the FLIPR System. Single point (10 µM final concentration) POC antagonist compound plates or ten point $IC_{50}$ compound plates containing 1:3 or 1:5 dilutions of antagonist compounds and an agonist activator plate (0.3 nM bradykinin final concentration, $EC_{80}$) are prepared using assay buffer. The cell plate and the compound plates are loaded onto the FLIPR and during the assay, fluorescence readings are taken simultaneously from all 96 wells of the cell plate. Ten 1-second readings are taken to establish a stable baseline for each well, then 25 µL from the B1 antagonist plate is rapidly (50 µL/sec.) added. The fluorescence signal is measured in 1-second (1 minute) followed by 6-second (2 minutes) intervals for a total of 3 minutes to determine if there is any agonist activity with the compounds. The B2 agonist, bradykinin, is then added to the cell plate and another 3 minutes are recorded to determine the percent inhibition at 10 µM (POC plates) or the $IC_{50}$ of the antagonist.

The $IC_{50}$ values for vehicle- or PEG-conjugated peptides tested in the hB1 aequorin assay were on average the slightly reduced in vitro activity conferred to peptides conjugated to larger PEG polymers. For example, the peptide represented by SEQ ID NO:36 and its acetylated form represented by SEQ ID NO:37, resulted in an $IC_{50}$ of 3.0 nM (+/–5 nM, n=8) and 3.2 nM (+/–3.2 nM, n=9), respectively at the hB1 receptor. However, the same peptide conjugated to PEG as described herein demonstrated approximately a 10-fold increase in $IC_{50}$ The native, acetylated, and PEG-conjugate forms of the peptide were inactive up to 10 µM in the hB2 FLIPR assay. None of the compounds showed agonist activity at either the hB1 or hB2 receptor.

C. Tissue Based In Vitro Assays of hB1 Receptor Binding Peptides:

The antagonist activity and selectivity for bradykinin B1 receptor of the peptides and/or vehicle-conjugated peptides of the present invention were determined with the in vitro human umbilical Vein (HUV) contractility assay described below:

Endothelium-denuded vessels were suspended in 20-ml organ baths containing an oxygenated (95% $O_2$ and 5% $CO_2$) and pre-warmed (37° C.) standard physiological salt solution of the following composition (in mM): NaCl 118.0, KCl 4.7, $MgSO_4$ 1.2, $CaCl_2$ 2.5, $KH_2PO_4$ 1.2, $NaHCO_3$ 25.0 and glucose 11.0 (pH 7.4). High K+ solutions (80 mM KCl) were prepared by equimolar replacement of NaCl with KCl. Hoe 140 (1 µM), mergetpa (1 µM) and captopril (10 µM) were also present throughout the experiments to block the B2 receptors and to prevent peptide degradation, respectively. The tissues were connected to force transducers for isometric tension recordings then allowed to equilibrate for a sufficient time under an optimal resting tension. The experiments were carried out using semi-automated isolated organ systems possessing eight organ baths each, with multichannel data acquisition. The tissues were exposed first to a high K+ solution (80 mM KCl) to obtain a control contraction. Following washings and a subsequent 60-min equilibration period, the tissues were exposed to cumulative increasing concentrations of the reference agonist Lys-desArg9-BK to obtain concentration-response curves in the absence (control preparations) or presence of various concentrations of the test compounds or the reference antagonist Lys-desArg9[Leu8]-BK (test preparations), which were added 15 min before the exposure to Lys-desArg9-BK. A concentration-response curve to Lys-desArg9-BK was generated in each preparation.

The parameter measured was the maximal change in tension induced by each agonist concentration and the results expressed as a percent of the control responses to KCl. The $EC_{50}$ values of the agonist (concentration producing a half-maximum response) were calculated by linear regression analysis of its concentration-response curves. The antagonist potencies of the test compounds and Lys-desArg9[Leu8]-BK were evaluated in terms of pA2 values (–log concentration producing a two-fold rightward shift of the agonist concentration-response curve), which were calculated according to Van Rossum (Van Rossum, J. M., Cumulative dose-response curves. II. Technique for the making of dose-response curves in isolated organs and the evaluation of drug parameters. Arch. Int. Pharmacodyn. Ther., 143:299-330 (1963)). The pA2 values were calculated using only antagonist concentrations that caused a significant rightward shift of the agonist concentration-response curve. The pA2 values are given as the mean±s.e.m. of three determinations. Statistical significance of the differences was determined using Student's t test and p values<0.05 were considered statistically significant.

D. In vitro B1-Inhibition Activity of Peptides and/or Conjugated Peptides

The effectiveness of the peptides and/or conjugated peptides as inhibitors of B1 activity (i.e., B1 "neutralization") can also be evaluated by measuring the ability of each peptide and/or conjugated peptide to block B1 stimulated CGRP and substance P release and calcium signaling in Dorsal Root Ganglion (DRG) neuronal cultures.

Dorsal Root Ganglion Neuronal Cultures. Dorsal root ganglia are dissected one by one under aseptic conditions from all spinal segments of embryonic 19-day old (E19) rats that are surgically removed from the uterus of timed-pregnant, terminally anesthetized Sprague-Dawley rats (Charles River, Wilmington, Mass.). DRG are collected in ice-cold L-15 media (GibcoBRL, Grand Island, N.Y.) containing 5% heat inactivated horse serum (GibcoBRL), and any loose connective tissue and blood vessels are removed. The DRG are rinsed twice in $Ca^{2+}$— and $Mg^{2+}$-free Dulbecco's phosphate buffered saline (DPBS), pH 7.4 (GibcoBRL). The DRG are then dissociated into single cell suspension using a papain dissociation system (Worthington Biochemical Corp., Freehold, N.J.). Briefly, DRG are incubated in a digestion solution containing 20 U/ml of papain in Earle's Balanced Salt Solution (EBSS) at 37° C. for fifty minutes. Cells are dissociated by trituration through fire-polished Pasteur pipettes in a dissociation medium consisting of MEM/Ham's F12, 1:1, 1 mg/ml ovomucoid inhibitor and 1 mg/ml ovalbumin, and 0.005% deoxyribonuclease I (DNase). The dissociated cells are pelleted at 200×g for five minutes and re-suspended in EBSS containing 1 mg/ml ovomucoid inhibitor, 1 mg/ml ovalbumin and 0.005% DNase. Cell suspension is centrifuged through a gradient solution containing 10 mg/ml ovomucoid inhibitor, 10 mg/ml ovalbumin at 200×g for six minutes to remove cell debris, and then filtered through a 88-μm nylon mesh (Fisher Scientific, Pittsburgh, Pa.) to remove any clumps. Cell number is determined with a hemocytometer, and cells are seeded into poly-ornithine 100 μg/ml (Sigma, St. Louis, Mo.) and mouse laminin 1 μg/ml (GibcoBRL)-coated 96-well plates at 10×10$^3$ cells/well in complete medium. The complete medium consists of minimal essential medium (MEM) and Ham's F12, 1:1, penicillin (100 U/ml), streptomycin (100 μg/ml), and 10% heat inactivated horse serum (GibcoBRL). The cultures are kept at 37° C., 5% $CO_2$ and 100% humidity. For controlling the growth of non-neuronal cells, 5-fluoro-2'-deoxyuridine (75 μM) and uridine (180 μM) are included in the medium.

Treatment with B1 and anti-B1 peptides and/or anti-B1 conjugated peptides. Two hours after plating, cells are treated with recombinant human β-B1 or recombinant rat β-B1 at a concentration of 10 ng/ml (0.38 nM). Positive controls comprising serial-diluted anti-B1 antibody (R&D Systems, Minneapolis, Minn.) are applied to each culture plate. Test peptides or test conjugated peptides (e.g., from Example 1) are added at ten concentrations using 3.16-fold serial dilutions. All samples are diluted in complete medium before being added to the cultures. Incubation time is generally around 40 hours prior to measurement of VR1 expression.

Measurement of VR1 Expression in DRG Neurons. Cultures are fixed with 4% paraformaldehyde in Hanks' balanced salt solution for fifteen minutes, blocked with Superblock (Pierce, Rockford, Ill.), and permeabilized with 0.25% Nonidet P-40 (Sigma) in Tris.HCl (Sigma)-buffered saline (TBS) for one hour at room temperature. Cultures are rinsed once with TBS containing 0.1% Tween 20 (Sigma) and incubated with rabbit anti-VR1 IgG (prepared at Amgen) for one and one-half hours at room temperature, followed by incubation of Eu-labeled anti-rabbit second antibody (Wallac Oy, Turku, Finland) for one hour at room temperature. Washes with TBS (3× five minutes with slow shaking) are applied after each antibody incubation. Enhance solution (150 μl/well, Wallac Oy) is added to the cultures. The fluorescence signal is then measured in a time-resolved fluorometer (Wallac Oy). VR1 expression in samples treated with the vehicle-conjugated peptides is determined by comparing to a standard curve of B1 titration from 0-1000 ng/ml. Percent inhibition (compared to maximum possible inhibition) of B1 effect on VR1 expression in DRG neurons is determined by comparing to controls that are not B1-treated.

Impaired receptor binding and functional activity for each of the PEG-conjugated peptide B1 antagonists was directly related to the size of the PEG group added and ranged from ~5-200 fold reductions in potency. Polyglycine linkers of ~5-7 residues worked well to preserve functional while longer linkers either showed little improvement ("flexible linker") or proved to be a detriment to activity ("rigid linker"). Finally, Table 8 illustrates the breadth of this application with a variety of different PEG-conjugated peptide B1 antagonists.

TABLE 8

Binding affinity (Ki) and Functional potency ($IC_{50}$) at the human B1 receptor (hB1) for peptide and PEGylated peptide antagonists

| Activated PEG reagent | Peptides per PEG | Peptide ($X^1$) – ($Y^1$)0 or 1 | hB1 Ki (nM) | hB1 $IC_{50}$ (nM) |
|---|---|---|---|---|
| MeO-20K-Maleimide[a] | 1 | SEQ ID NO: 28 | 114 | 110 |
| MeO-20K-Maleimide[a] | 1 | SEQ ID NO: 29 | 252 | 237 |
| MeO-20K-Maleimide[a] | 1 | SEQ ID NO: 30 | 230 | 61 |
| MeO-20K-Maleimide[a] | 1 | SEQ ID NOS: 29 + 42 | 22 | 54 |
| MeO-20K-Maleimide[a] | 1 | SEQ ID NO: 32 | 9 | 69 |
| MeO-20K-Maleimide[a] | 1 | SEQ ID NO: 33 | 75 | 98 |
| MeO-20K-propionaldehyde[b] | 1 | SEQ ID NO: 13 | 1 | 35 |
| Maleimide-20K-Maleimide[a] | 2 | SEQ ID NO: 33 | 11 | 77 |
| MeO-20K SPA[c] | 1 | SEQ ID NO: 13 | 10 | 52 |
| Tetrakis-20K-SPA[c] | 4 | SEQ ID NO: 13 | 0.14 | 10 |
| Tetrakis-20K-SPA[d] | 4 | SEQ ID NO: 13 | 0.14 | 10 |
| none | NA | SEQ ID NO: 13 | 0.10 | 0.5 |
| none | NA | SEQ ID NO: 15 | 0.19 | 1 |
| none | NA | SEQ ID NO: 49 | 0.77 | 0.5 |
| none | NA | SEQ ID NO: 50 | 0.2 | 6 |
| none | NA | SEQ ID NO: 22 | 0.38 | 2 |
| None | NA | SEQ ID NO: 37 | 0.8 | 1 |

[a]Generated by one-pot process described in Scheme 4;
[b]Reductive amination at N-terminal residue, epsilon amine;
[c]acylated on the N-terminal residue, epsilon amine;
[d]acylated on the N-terminal residue, alpha amine Example 7

Determination of Stability of Peptides and/or Conjugated Peptides

A. Rat Kidney Brush Border Microvilli Assay

Kidney membranes are prepared according to the procedure set forth in by Booth et al. (Biochemical Journal, 142: 575 (1974)). Protein concentrations are determined by the method of Bradford (Anal. Biochemistry., 72:248-254 (1976)).

B. Rat or Human Lung S9 Homogenate Assay Rat or Human lung is prepared as described by Skidgel et al. (Biochemical Pharmacology 33: 3471 (1984)).

The test compounds are prepared at 1 mM concentration in a PBS solution (pH=7.1). Test compounds are added to a preparation of tissue from procedure A or B (final protein concentration of 2 mg/ml) and incubated at 37° C. At various time points, the protein is precipitated with acetonitrile, 0.1M HCl in acetonitrile or 10% TFA in water. The precipitate is removed by centrifugation, and the filtrate further filtered through a 0.1 μM membrane. The sample is then analyzed by reverse phase HPLC (4.6×300 mm Novapak HR C18 (Waters Corporation, Milford, Mass.) flow=1 mL/min, linear gradient from 10% ACN (0.1% Formic acid)—90% water (0.1% Formic acid) to 50% ACN (0.1% Formic acid)—50% water (0.1% Formic acid over 20 minutes) with mass spectroscopy detection. The concentration of the test compound at time T relative to the internal standard is fitted to a first order loss function ([compound]$_t$=[compound]$_0$ $(1-e^{(-kt)})$; "[compound]0" and "[compound]t" are the concentration of test compound at time zero and the concentration of test compound at the time the sample is withdrawn, respectively; the variable "t" is the time the sample is withdrawn for analysis; and k is the rate of test compound concentration change). The variable "k" is determined by using a non-linear regression approach supplied by the JMP Statistical software package.

Given that the test compound concentration decreases over time, the values of "k" are negative. The half-life is calculated from the model derived value of "k" using the following formula: T ½=(Ln 2)/k Example 8

In Vivo Antinociceptive Activity of Anti-B1 Peptides and Vehicle-conjugated Anti-B1 Peptides in Rat and Monkey Pain Models A. Rat Neuropathic Pain Model. Male Sprague-Dawley rats (200 g) are anesthetized with isoflurane inhalant anesthesia and the left lumbar spinal nerves at the level of L5 and L6 are tightly ligated (4-0 silk suture) distal to the dorsal root ganglion and prior to entrance into the sciatic nerve, as first described by Kim and Chung (An experimental model for peripheral neuropathy produced by segmental spinal nerve ligation in the rat. Pain 50:355-363, (1992)). The incisions are closed and the rats are allowed to recover. This procedure results in mechanical (tactile) allodynia in the left hind paw as assessed by recording the pressure at which the affected paw (ipsilateral to the site of nerve injury) was withdrawn from graded stimuli (von Frey filaments ranging from 4.0 to 148.1 mN) applied perpendicularly to the plantar surface of the paw (between the footpads) through wire-mesh observation cages. A paw withdrawal threshold (PWT) was determined by sequentially increasing and decreasing the stimulus strength and analyzing withdrawal data using a Dixon non-parametric test, as described by Chaplan, S. R., et al. (Quantitative assessment of tactile allodynia in the rat paw. J. Neurosci. Meth, 53:55-63 (1994)).

Normal rats and sham surgery rats (nerves isolated but not ligated) withstand at least 148.1 mN (equivalent to 15 g) of pressure without responding. Spinal nerve ligated rats respond to as little as 4.0 mN (equivalent to 0.41 g) of pressure on the affected paw. Rats are included in the study only if they did not exhibit motor dysfunction (e.g., paw dragging or dropping) and their PWT was below 39.2 mN (equivalent to 4.0 g). At least seven days after surgery rats are treated with test peptides or test vehicle-conjugated peptides (usually a screening dose of about 1 mg/kg and about 60 mg/kg, respectively) or control diluent (PBS) once by s.c. injection and PWT was determined each day thereafter for 7 days.

B. Rat CFA Inflammatory Pain Model. Male Sprague-Dawley rats (200 g) are lightly anesthetized with isoflurane inhalant anesthesia and the left hindpaw is injected with complete Freund's adjuvant (CFA), 0.15 ml. This procedure results in mechanical (tactile) allodynia in the left hind paw as assessed by recording the pressure at which the affected paw is withdrawn from graded stimuli (von Frey filaments ranging from 4.0 to 148.1 mN) applied perpendicularly to the plantar surface of the paw (between the footpads) through wire-mesh observation cages. PWT is determined by sequentially increasing and decreasing the stimulus strength and analyzing withdrawal data using a Dixon non-parametric test, as described by Chaplan et al. (1994). Rats are included in the study only if they do not exhibit motor dysfunction (e.g., paw dragging or dropping) or broken skin and their PWT is below 39.2 mN (equivalent to 4.0 g). At least seven days after CFA injection rats are treated with test peptides and/or test vehicle-conjugated peptides (usually a screening dose of 60 mg/kg) or control solution (PBS) once by s.c. injection and PWT is determined each day thereafter for 7 days. Average paw withdrawal threshold (PWT) was converted to percent of maximum possible effect (% MPE) using the following formula: % MPE=100*(PWT of treated rats−PWT of control rats)/(15-PWT of control rats). Thus, the cutoff value of 15 g (148.1 mN) is equivalent to 100% of the MPE and the control response is equivalent to 0% MPE.

Preferred peptides and vehicle-conjugated peptides of the present invention are expected to produce an antinociceptive effect with a PD relationship at a screening dose of about 1 mg/kg and about 60 mg/kg, respectively.

B. Green Monkey LPS Inflammation Model. The effectiveness of peptides and/or conjugated peptides as inhibitors of B1 activity may be evaluated in Male green monkeys (*Cercopithaecus aethiops St Kitts*) challenged locally with B1 agonists essentially as described by deBlois and Horlick (British Journal of Pharmacology. 132:327-335 (2002)), which is hereby incorporated by reference in its entirety).

In order to determine whether PEG-conjugated peptide antagonists of the present invention inhibit B1 induced oedema the studies described below were conducted on male green monkeys (*Cercopithaecus aethiops St Kitts*) at the Caribbean Primates Ltd. experimental farm (St Kitts, West Indies). Procedures were reviewed and accepted by the Animal Care Committees of the CR-CHUM (Montreal, Canada) and of Caribbean Primates Ltd. (St Kitts, West Indies). Animals weighing 6.0±0.5 kg (n=67) were anesthetized (50 mg ketamine $kg^{-1}$) and pretreated with a single intravenous injection of LPS (90 µg $kg^{-1}$) or saline (1 ml) via the saphenous vein.

1. Inflammation Studies

Kinin-induced oedema was evaluated by the ventral skin fold assay (Sciberras et al., 1987). Briefly, anesthetized monkeys were injected with captopril (1 mg $kg^{-1}$ 30 min before assay). A single subcutaneous injection of dKD, BK or the vehicle (2 mM amastatin in 100 µl Ringer's lactate) was given in the ventral area and the increase in thickness of skin folds was monitored for 30-45 min using a calibrated caliper. The results were expressed as the difference between the skin fold thickness before and after the subcutaneous injection. Captopril and amastatin were used to reduce degradation of kinins at the carboxyl- and amino-terminus, respectively.

Antagonist Schild Analysis

The dose-response relationship for dKD (1-100 nmol)-induced oedema was determined at 24 h post-LPS in the absence or presence of different concentrations of PEG-peptide antagonist. BK (30 nmol) was used as a positive control.

Antagonist Time Course

The time course of inhibition by antagonist was determined at 4, 24, 48, 72 and/or 96 h after single bolus administration. BK (30 nmol) was used as a positive control.

Drugs

Ketamine hydrochloride, LPS, amastatin and captopril were from Sigma (MO, U.S.A.). All peptides were from Phoenix Pharmaceuticals (CA, U.S.A.).

Statistics

Values are presented as mean±standard error of the mean (s.e. mean). In edema studies, the pre-injection thickness of the skin folds was subtracted from the values after subcutaneous challenge. Curve fitting and $EC_{50}$ calculations were obtained using the Delta Graph 4.0 software for Apple Computers. Data were compared by two-way analysis of variance followed by unpaired, one tail Student's t-test with Bonferroni correction. $p<0.05$ was considered statistically significant.

LPS administration to green monkeys increased from a null level their sensitivity to a $B_1$ receptor agonist in an edema formation assay. Comparatively, responses to the $B_2$ receptor agonist BK were not affected.

Surprisingly, a single subcutaneous dose at 10 mg/kg of a representative 5kD PEG-conjugated peptide and a 20 kD PEG-conjugated peptide of the same peptide analog was sufficient to relieve a pre-established B1 agonist induced inflammatory response and suppress successive daily agonist challenges for 3 and 4 days, respectively. No tachyphalaxis was observed with B1 challenge up to 96 h. The effect was also determined to be selective at B1 rather than B2. Furthermore, the 5K PEG-conjugate inhibited edema in response to dKD challenge longer than the unconjugated (i.e., native peptide) peptide although rapid onset and efficacy was comparable for both molecules up to 1.25 hours.

Example 9

Rat Pharmacokinetic Studies

Various peptides or conjugated peptides (in an aqueous medium) were dosed as a bolus to male Sprague-Dawley rats via an intravenous (iv) or subcutaneous (sc) route. Blood samples were collected at various time points (e.g., 0, 15, 30 minutes and/or 1, 2, 4, 6, 8, 10, 12, 18, 24, 30, 36, 42, 48, 60, 72, 84, 96, 120, 240, and/or 320 hours after the injection) into heparized tubes. Plasma was removed from pelleted cells upon centrifugation and either frozen or immediately processed. The compound of interest in the plasma was quantitated by an analyte-specific LC-MS/MS or an ELISA method. Various standard pharmacokinetic parameters such as clearance (CL), apparent clearance (CL/F), volume of distribution (Vss), mean residence time (MRT), area under the curve (AUC), and terminal half-life ($t_{1/2}$) were calculated by non-compartmental method (for example, see Table 9).

TABLE 9

Peptide and PEGylated peptide B1 antagonists Pharmacokinetic Studies in Rat

| Activated PEG reagent | Peptides per PEG | Peptide | $t_{1/2}$ (h) | AUC 0–inf |
|---|---|---|---|---|
| MeO-20K-Maleimide[a] | 1 | SEQ ID NO: 33 | — | 28387 |
| MeO-20K-propionaldehyde[b] | 1 | SEQ ID NO: 13 | 33.7[c] | 16877[c] |
| Maleimide-20K-Maleimide[a] | 2 | SEQ ID NO: 33 | 25.6[c] | 28580[c] |
| MeO-20K SPA[d] | 1 | SEQ ID NO: 13 | 27.3[c] | 10701[c] |
| Tetrakis-20K-SPA[d] | 4 | SEQ ID NO: 13 | 28.7[e] | 8475[e] |
| Tetrakis-20K-SPA[f] | 4 | SEQ ID NO: 13 | 30.8[e] | 63239[e] |
| none | NA | SEQ ID NO: 13 | 1.2[g] | 255[g] |
| none | NA | SEQ ID NO: 15 | 2.76[c] | 7720[c] |
| none | NA | SEQ ID NO: 13 | 0.6[h] | 9[h] |
| none | NA | SEQ ID NO: 49 | 1.0[i] | 13862[i] |
| none | NA | SEQ ID NO: 50 | 2.0[i] | 5529[i] |
| none | NA | SEQ ID NO: 22 | 1.0[i] | 7891[i] |
| None | NA | SEQ ID NO: 37 | 0.4[i] | 1122[i] |
| None | NA | SEQ ID NO: 37 | 0.6[g] | 18288[g] |

[a]Generated by one-pot process described in Scheme 4;
[b]Reductive amination at N-terminal residue, epsilon amine;
[c]1 mpk sc;
[d]acylated on the N-terminal residue, epsilon amine;
[e]0.5 mpk sc;
[f]acylated on the N-terminal residue, alpha amine
[g]30 mpk sc;
[h]1 mpk iv; and
[i]3 mpk iv It will be appreciated that various modifications may be made in the invention as described above. Accordingly, the scope of the invention is defined in the following claims.

SEQUENCE LISTING

```
<160> NUMBER OF SEQ ID NOS: 60

<210> SEQ ID NO 1
<211> LENGTH: 9
<212> TYPE: PRT
<213> ORGANISM: HUMAN

<400> SEQUENCE: 1

Arg Pro Pro Gly Phe Ser Pro Phe Arg
1               5

<210> SEQ ID NO 2
<211> LENGTH: 10
<212> TYPE: PRT
<213> ORGANISM: HUMAN

<400> SEQUENCE: 2

Lys Arg Pro Pro Gly Phe Ser Pro Phe Arg
1               5                   10

<210> SEQ ID NO 3
<211> LENGTH: 11
<212> TYPE: PRT
<213> ORGANISM: ARTIFICIAL
<220> FEATURE:
<223> OTHER INFORMATION: SYNTHETICALLY PRODUCED

<400> SEQUENCE: 3
```

```
Met Lys Arg Pro Pro Gly Phe Ser Pro Phe Arg
1               5                   10

<210> SEQ ID NO 4
<211> LENGTH: 8
<212> TYPE: PRT
<213> ORGANISM: HUMAN

<400> SEQUENCE: 4

Arg Pro Pro Gly Phe Ser Pro Phe
1               5

<210> SEQ ID NO 5
<211> LENGTH: 8
<212> TYPE: PRT
<213> ORGANISM: ARTIFICIAL
<220> FEATURE:
<223> OTHER INFORMATION: SYNTHETICALLY PRODUCED

<400> SEQUENCE: 5

Arg Pro Pro Gly Phe Ser Pro Leu
1               5

<210> SEQ ID NO 6
<211> LENGTH: 9
<212> TYPE: PRT
<213> ORGANISM: ARTIFICIAL
<220> FEATURE:
<223> OTHER INFORMATION: SYNTHETICALLY PRODUCED

<400> SEQUENCE: 6

Lys Arg Pro Pro Gly Phe Ser Pro Leu
1               5

<210> SEQ ID NO 7
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as D isomer of
      Arginine (DArg)
<220> FEATURE:
<221> NAME/KEY: misc_feature
<222> LOCATION: (4)..(4)
<223> OTHER INFORMATION: Xaa at position 4 is defined as
      Trans-4-hydroxy-proline (Hyp)
<220> FEATURE:
<221> NAME/KEY: misc_feature
<222> LOCATION: (6)..(6)
<223> OTHER INFORMATION: Xaa at position 6 is defined as Beta-
      (2-Thienyl)-alanine (Thi)
<220> FEATURE:
<221> NAME/KEY: misc_feature
<222> LOCATION: (8)..(8)
<223> OTHER INFORMATION: Xaa at position 8 is defined as D isomer of
      1,2,3,4-tetrahydroisoquinoline-3-carboxylic acid (Dtic)
<220> FEATURE:
<221> NAME/KEY: misc_feature
<222> LOCATION: (9)..(9)
<223> OTHER INFORMATION: Xaa at position 9 is defined as
      Octahydroindole-2-carboxylic acid (Oic)

<400> SEQUENCE: 7

Xaa Arg Pro Xaa Gly Xaa Ser Xaa Xaa Arg
1               5                   10
```

```
<210> SEQ ID NO 8
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as DArg
<220> FEATURE:
<221> NAME/KEY: misc_feature
<222> LOCATION: (4)..(4)
<223> OTHER INFORMATION: Xaa at position 4 is defined as Hyp
<220> FEATURE:
<221> NAME/KEY: misc_feature
<222> LOCATION: (6)..(6)
<223> OTHER INFORMATION: Xaa at position 6 is defined as Thi
<220> FEATURE:
<221> NAME/KEY: misc_feature
<222> LOCATION: (8)..(8)
<223> OTHER INFORMATION: Xaa at position 8 is defined as Dtic
<220> FEATURE:
<221> NAME/KEY: misc_feature
<222> LOCATION: (9)..(9)
<223> OTHER INFORMATION: Xaa at position 9 is defined as Oic

<400> SEQUENCE: 8

Xaa Arg Pro Xaa Gly Xaa Ser Xaa Xaa
1               5

<210> SEQ ID NO 9
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as DArg
<220> FEATURE:
<221> NAME/KEY: misc_feature
<222> LOCATION: (4)..(4)
<223> OTHER INFORMATION: Xaa at position 4 is defined as Hyp
<220> FEATURE:
<221> NAME/KEY: misc_feature
<222> LOCATION: (6)..(6)
<223> OTHER INFORMATION: Xaa at position 6 is defined as Thi
<220> FEATURE:
<221> NAME/KEY: misc_feature
<222> LOCATION: (8)..(8)
<223> OTHER INFORMATION: Xaa at position 8 is defined as D isomer of
      4S-D-prolyl-propylether (DHype)
<220> FEATURE:
<221> NAME/KEY: misc_feature
<222> LOCATION: (9)..(9)
<223> OTHER INFORMATION: Xaa at position 9 is defined as Oic

<400> SEQUENCE: 9

Xaa Arg Pro Xaa Gly Xaa Ser Xaa Xaa Arg
1               5                   10

<210> SEQ ID NO 10
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: misc_feature
<222> LOCATION: (7)..(7)
<223> OTHER INFORMATION: Xaa at position 7 is defined as N-methyl
      L-phenylalanine (MePhe)
<220> FEATURE:
<221> NAME/KEY: misc_feature
<222> LOCATION: (9)..(9)
<223> OTHER INFORMATION: Xaa at position 9 is defined as D isomer of
      Beta-2-napthyl-alanine (D-Beta-NaI)

<400> SEQUENCE: 10

Leu Leu Arg Pro Pro Gly Xaa Ser Xaa Ile
1               5                   10

<210> SEQ ID NO 11
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as DArg
<220> FEATURE:
<221> NAME/KEY: misc_feature
<222> LOCATION: (4)..(4)
<223> OTHER INFORMATION: Xaa at position 4 is defined as Hyp
<220> FEATURE:
<221> NAME/KEY: misc_feature
<222> LOCATION: (6)..(6)
<223> OTHER INFORMATION: Xaa at position 6 is defined as
      2-indanylglycine (Igl)
<220> FEATURE:
<221> NAME/KEY: misc_feature
<222> LOCATION: (8)..(8)
<223> OTHER INFORMATION: Xaa at position 8 is defined as D isomer of
      2-indanylglycine(DIgl)
<220> FEATURE:
<221> NAME/KEY: misc_feature
<222> LOCATION: (9)..(9)
<223> OTHER INFORMATION: Xaa at position 9 is defined as Oic

<400> SEQUENCE: 11

Xaa Arg Pro Xaa Gly Xaa Ser Xaa Xaa Arg
1               5                   10

<210> SEQ ID NO 12
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Igl
<220> FEATURE:
<221> NAME/KEY: misc_feature
<222> LOCATION: (9)..(9)
<223> OTHER INFORMATION: Xaa at position 9 is defined as DIgl
<220> FEATURE:
<221> NAME/KEY: misc_feature
<222> LOCATION: (10)..(10)
<223> OTHER INFORMATION: Xaa at position 10 is defined as Oic

<400> SEQUENCE: 12

Lys Lys Arg Pro Xaa Gly Xaa Ser Xaa Xaa
1               5                   10
```

<210> SEQ ID NO 13
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as
      Cyclopentylglycine (Cpg)
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 13

Lys Lys Arg Pro Xaa Gly Xaa Ser Xaa Xaa
1               5                   10

<210> SEQ ID NO 14
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as DArg
<220> FEATURE:
<221> NAME/KEY: misc_feature
<222> LOCATION: (4)..(4)
<223> OTHER INFORMATION: Xaa at position 4 is defined as Hyp
<220> FEATURE:
<221> NAME/KEY: misc_feature
<222> LOCATION: (6)..(6)
<223> OTHER INFORMATION: Xaa at position 6 is defined as Igl
<220> FEATURE:
<221> NAME/KEY: misc_feature
<222> LOCATION: (8)..(8)
<223> OTHER INFORMATION: Xaa at position 8 is defined as D isomer of
      pentafluorophenylalanine (Df5f)
<220> FEATURE:
<221> NAME/KEY: misc_feature
<222> LOCATION: (9)..(9)
<223> OTHER INFORMATION: Xaa at position 9 is defined as Igl

<400> SEQUENCE: 14

Xaa Arg Pro Xaa Gly Xaa Ser Xaa Xaa Arg
1               5                   10

<210> SEQ ID NO 15
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as DOrn
<220> FEATURE:
<221> NAME/KEY: misc_feature
<222> LOCATION: (5)..(5)
<223> OTHER INFORMATION: Xaa at position 5 is defined as Hyp

```
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 15

Xaa Leu Arg Pro Xaa Gly Xaa Ser Xaa Xaa
 1               5                  10

<210> SEQ ID NO 16
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as DOrn
<220> FEATURE:
<221> NAME/KEY: misc_feature
<222> LOCATION: (5)..(5)
<223> OTHER INFORMATION: Xaa at position 5 is defined as Thiazolidine-
      4-carboxylic acid(Thz)
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 16

Xaa Leu Arg Pro Xaa Gly Xaa Ser Xaa Xaa
 1               5                  10

<210> SEQ ID NO 17
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as Beta-3-
      Pyridyl-alanine (3Pal)
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
```

<223> OTHER INFORMATION: Xaa at position 10 is defined as Cpg

<400> SEQUENCE: 17

Xaa Leu Arg Pro Xaa Gly Xaa Ser Xaa Xaa
1               5                   10

<210> SEQ ID NO 18
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as D-4'-
      pyridylalanine (4Pal)
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 18

Xaa Leu Arg Pro Xaa Gly Xaa Ser Xaa Xaa
1               5                   10

<210> SEQ ID NO 19
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as
      cyclohexylalanine (Cha)
<220> FEATURE:
<221> NAME/KEY: misc_feature
<222> LOCATION: (4)..(4)
<223> OTHER INFORMATION: Xaa at position 4 is defined as Hyp
<220> FEATURE:
<221> NAME/KEY: misc_feature
<222> LOCATION: (6)..(6)
<223> OTHER INFORMATION: Xaa at position 6 is defined as Cpg
<220> FEATURE:
<221> NAME/KEY: misc_feature
<222> LOCATION: (8)..(8)
<223> OTHER INFORMATION: Xaa at position 8 is defined as Dtic
<220> FEATURE:
<221> NAME/KEY: misc_feature
<222> LOCATION: (9)..(9)
<223> OTHER INFORMATION: Xaa at position 9 is defined as Cpg

<400> SEQUENCE: 19

Xaa Arg Pro Xaa Gly Xaa Ser Xaa Xaa
1               5

<210> SEQ ID NO 20
<211> LENGTH: 9
<212> TYPE: PRT

```
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as Beta-2-napthyl-
      alanine (2Nal)
<220> FEATURE:
<221> NAME/KEY: misc_feature
<222> LOCATION: (4)..(4)
<223> OTHER INFORMATION: Xaa at position 4 is defined as Hyp
<220> FEATURE:
<221> NAME/KEY: misc_feature
<222> LOCATION: (6)..(6)
<223> OTHER INFORMATION: Xaa at position 6 is defined as Cpg
<220> FEATURE:
<221> NAME/KEY: misc_feature
<222> LOCATION: (8)..(8)
<223> OTHER INFORMATION: Xaa at position 8 is defined as Dtic
<220> FEATURE:
<221> NAME/KEY: misc_feature
<222> LOCATION: (9)..(9)
<223> OTHER INFORMATION: Xaa at position 9 is defined as Cpg

<400> SEQUENCE: 20

Xaa Arg Pro Xaa Gly Xaa Ser Xaa Xaa
1               5

<210> SEQ ID NO 21
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (4)..(4)
<223> OTHER INFORMATION: Xaa at position 4 is defined as Hyp
<220> FEATURE:
<221> NAME/KEY: misc_feature
<222> LOCATION: (6)..(6)
<223> OTHER INFORMATION: Xaa at position 6 is defined as Cpg
<220> FEATURE:
<221> NAME/KEY: misc_feature
<222> LOCATION: (8)..(8)
<223> OTHER INFORMATION: Xaa at position 8 is defined as Dtic
<220> FEATURE:
<221> NAME/KEY: misc_feature
<222> LOCATION: (9)..(9)
<223> OTHER INFORMATION: Xaa at position 9 is defined as Cpg

<400> SEQUENCE: 21

Leu Arg Pro Xaa Gly Xaa Ser Xaa Xaa
1               5

<210> SEQ ID NO 22
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as D isomer of
      lysine (DLys)
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
```

```
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 22

Xaa Leu Arg Pro Xaa Gly Xaa Ser Xaa Xaa
1               5                   10

<210> SEQ ID NO 23
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (2)..(2)
<223> OTHER INFORMATION: Xaa at position 2 is defined as DOrn
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 23

Leu Xaa Arg Pro Xaa Gly Xaa Ser Xaa Xaa
1               5                   10

<210> SEQ ID NO 24
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (2)..(2)
<223> OTHER INFORMATION: Xaa at position 2 is defined as Cha
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 24

Leu Xaa Arg Pro Xaa Gly Xaa Ser Xaa Xaa
1               5                   10
```

<210> SEQ ID NO 25
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (2)..(2)
<223> OTHER INFORMATION: Xaa at position 2 is defined as S-aminobutyric acid (Abu)
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 25

Leu Xaa Arg Pro Xaa Gly Xaa Ser Xaa Xaa
1               5                   10

<210> SEQ ID NO 26
<211> LENGTH: 11
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (2)..(2)
<223> OTHER INFORMATION: Xaa at position 1 is defined as 2Nal
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg
<220> FEATURE:
<221> NAME/KEY: misc_feature
<222> LOCATION: (11)..(11)
<223> OTHER INFORMATION: Xaa can be any naturally occurring amino acid

```
<400> SEQUENCE: 26

Leu Xaa Xaa Arg Pro Xaa Gly Xaa Ser Xaa Xaa
1               5                   10

<210> SEQ ID NO 27
<211> LENGTH: 13
<212> TYPE: PRT
<213> ORGANISM: ARTIFICIAL
<220> FEATURE:
<223> OTHER INFORMATION: SYNTHETICALLY PRODUCED

<400> SEQUENCE: 27

Cys Gly Gly Gly Lys Arg Pro Pro Gly Phe Ser Pro Leu
1               5                   10

<210> SEQ ID NO 28
<211> LENGTH: 15
<212> TYPE: PRT
<213> ORGANISM: ARTIFICIAL
<220> FEATURE:
<223> OTHER INFORMATION: SYNTHETICALLY PRODUCED

<400> SEQUENCE: 28

Cys Gly Gly Gly Gly Gly Lys Arg Pro Pro Gly Phe Ser Pro Leu
1               5                   10                  15

<210> SEQ ID NO 29
<211> LENGTH: 15
<212> TYPE: PRT
<213> ORGANISM: ARTIFICIAL
<220> FEATURE:
<223> OTHER INFORMATION: SYNTHETICALLY PRODUCED

<400> SEQUENCE: 29

Cys Gly Gly Gly Gly Gly Lys Lys Arg Pro Gly Phe Ser Pro Leu
1               5                   10                  15

<210> SEQ ID NO 30
<211> LENGTH: 17
<212> TYPE: PRT
<213> ORGANISM: ARTIFICIAL
<220> FEATURE:
<223> OTHER INFORMATION: SYNTHETICALLY PRODUCED

<400> SEQUENCE: 30

Cys Gly Gly Gly Gly Gly Lys Arg Lys Arg Pro Pro Gly Phe Ser Pro
1               5                   10                  15

Leu

<210> SEQ ID NO 31
<211> LENGTH: 12
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (3)..(3)
<223> OTHER INFORMATION: Xaa at position 3 is defined as CH2-CH2-CH2-
      CH2-CH2-CH2

<400> SEQUENCE: 31

Cys Gly Xaa Lys Arg Pro Pro Gly Phe Ser Pro Leu
1               5                   10

<210> SEQ ID NO 32
```

```
<211> LENGTH: 16
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (13)..(13)
<223> OTHER INFORMATION: Xaa at position 13 is defined as MePhe
<220> FEATURE:
<221> NAME/KEY: misc_feature
<222> LOCATION: (15)..(15)
<223> OTHER INFORMATION: Xaa at position 15 is defined as D-Beta-NaI

<400> SEQUENCE: 32

Cys Gly Gly Gly Gly Gly Leu Leu Arg Pro Pro Gly Xaa Ser Xaa Ile
 1               5                  10                  15

<210> SEQ ID NO 33
<211> LENGTH: 16
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (11)..(11)
<223> OTHER INFORMATION: Xaa at position 11 is defined as Hyp
<220> FEATURE:
<221> NAME/KEY: misc_feature
<222> LOCATION: (13)..(13)
<223> OTHER INFORMATION: Xaa at position 13 is defined as Cpg
<220> FEATURE:
<221> NAME/KEY: misc_feature
<222> LOCATION: (15)..(15)
<223> OTHER INFORMATION: Xaa at position 15 is defined as Dtic
<220> FEATURE:
<221> NAME/KEY: misc_feature
<222> LOCATION: (16)..(16)
<223> OTHER INFORMATION: Xaa at position 16 is defined as Cpg

<400> SEQUENCE: 33

Cys Gly Gly Gly Gly Gly Lys Lys Arg Pro Xaa Gly Xaa Ser Xaa Xaa
 1               5                  10                  15

<210> SEQ ID NO 34
<211> LENGTH: 18
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (12)..(12)
<223> OTHER INFORMATION: Xaa at position 12 is defined as Hyp
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa at position 14 is defined as Cpg
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa at position 16 is defined as Dtic
<220> FEATURE:
<221> NAME/KEY: misc_feature
<222> LOCATION: (17)..(17)
<223> OTHER INFORMATION: Xaa at position 17 is defined as Cpg
```

```
<220> FEATURE:
<221> NAME/KEY: misc_feature
<222> LOCATION: (18)..(18)
<223> OTHER INFORMATION: Xaa can be any naturally occurring amino acid

<400> SEQUENCE: 34

Cys Gly Gly Gly Gly Gly Gly Lys Lys Arg Pro Xaa Gly Xaa Ser
1               5                   10                  15

Xaa Xaa

<210> SEQ ID NO 35
<211> LENGTH: 16
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa at position 12 is defined as Hyp
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa at position 14 is defined as Cpg
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa at position 16 is defined as Dtic
<220> FEATURE:
<221> NAME/KEY: misc_feature
<222> LOCATION: (17)..(17)
<223> OTHER INFORMATION: Xaa at position 17 is defined as Cpg

<400> SEQUENCE: 35

Cys Gly Gly Gly Gly Gly Lys Lys Arg Pro Xaa Gly Xaa Ser Xaa Xaa
1               5                   10                  15

<210> SEQ ID NO 36
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
```

```
<223> OTHER INFORMATION: Xaa at position 10 is defined as Cpg

<400> SEQUENCE: 36

Lys Lys Arg Pro Xaa Gly Xaa Ser Xaa Xaa
1               5                   10

<210> SEQ ID NO 37
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa at position 6 is defined as Hyp
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa at position 8 is defined as Cpg
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa at position 10 is defined as Dtic
<220> FEATURE:
<221> NAME/KEY: misc_feature
<222> LOCATION: (11)..(11)
<223> OTHER INFORMATION: Xaa at position 11 is defined as Cpg

<400> SEQUENCE: 37

Lys Lys Arg Pro Xaa Gly Xaa Ser Xaa Xaa
1               5                   10

<210> SEQ ID NO 38
<211> LENGTH: 10
<212> TYPE: PRT
<213> ORGANISM: ARTIFICIAL
<220> FEATURE:
<223> OTHER INFORMATION: SYNTHETICALLY PRODUCED

<400> SEQUENCE: 38

Cys Lys Arg Pro Pro Gly Phe Ser Pro Leu
1               5                   10

<210> SEQ ID NO 39
<211> LENGTH: 16
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (7)..(7)
<223> OTHER INFORMATION: Xaa at position 7 is defined as DOrn
<220> FEATURE:
<221> NAME/KEY: misc_feature
<222> LOCATION: (11)..(11)
```

```
<223> OTHER INFORMATION: Xaa at position 11 is defined as Hyp
<220> FEATURE:
<221> NAME/KEY: misc_feature
<222> LOCATION: (13)..(13)
<223> OTHER INFORMATION: Xaa at position 13 is defined as Cpg
<220> FEATURE:
<221> NAME/KEY: misc_feature
<222> LOCATION: (15)..(15)
<223> OTHER INFORMATION: Xaa at position 15 is defined as Dtic
<220> FEATURE:
<221> NAME/KEY: misc_feature
<222> LOCATION: (16)..(16)
<223> OTHER INFORMATION: Xaa at position 16 is defined as Cpg

<400> SEQUENCE: 39

Cys Gly Gly Gly Gly Gly Xaa Leu Arg Pro Xaa Gly Xaa Ser Xaa Xaa
1               5                  10                  15

<210> SEQ ID NO 40
<211> LENGTH: 16
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (7)..(7)
<223> OTHER INFORMATION: Xaa at position 7 is defined as DOrn
<220> FEATURE:
<221> NAME/KEY: misc_feature
<222> LOCATION: (11)..(11)
<223> OTHER INFORMATION: Xaa at position 11 is defined as Thz
<220> FEATURE:
<221> NAME/KEY: misc_feature
<222> LOCATION: (13)..(13)
<223> OTHER INFORMATION: Xaa at position 13 is defined as Cpg
<220> FEATURE:
<221> NAME/KEY: misc_feature
<222> LOCATION: (15)..(15)
<223> OTHER INFORMATION: Xaa at position 15 is defined as Dtic
<220> FEATURE:
<221> NAME/KEY: misc_feature
<222> LOCATION: (16)..(16)
<223> OTHER INFORMATION: Xaa at position 16 is defined as Cpg

<400> SEQUENCE: 40

Cys Gly Gly Gly Gly Gly Xaa Leu Arg Pro Xaa Gly Xaa Ser Xaa Xaa
1               5                  10                  15

<210> SEQ ID NO 41
<211> LENGTH: 16
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (8)..(8)
<223> OTHER INFORMATION: Xaa at position 8 is defined as DOrn
<220> FEATURE:
<221> NAME/KEY: misc_feature
<222> LOCATION: (11)..(11)
<223> OTHER INFORMATION: Xaa at position 11 is defined as Hyp
<220> FEATURE:
<221> NAME/KEY: misc_feature
<222> LOCATION: (13)..(13)
<223> OTHER INFORMATION: Xaa at position 14 is defined as Cpg
<220> FEATURE:
<221> NAME/KEY: misc_feature
<222> LOCATION: (15)..(15)
<223> OTHER INFORMATION: Xaa at position 15 is defined as Dtic
<220> FEATURE:
<221> NAME/KEY: misc_feature
<222> LOCATION: (16)..(16)
<223> OTHER INFORMATION: Xaa at position 16 is defined as Cpg
```

<400> SEQUENCE: 41

Cys Gly Gly Gly Gly Gly Leu Xaa Arg Pro Xaa Gly Xaa Ser Xaa Xaa
1               5                   10                  15

<210> SEQ ID NO 42
<211> LENGTH: 15
<212> TYPE: PRT
<213> ORGANISM: ARTIFICIAL
<220> FEATURE:
<223> OTHER INFORMATION: SYNTHETICALLY PRODUCED

<400> SEQUENCE: 42

Gly Gly Gly Gly Gly Lys Lys Arg Pro Pro Gly Phe Ser Pro Leu
1               5                   10                  15

<210> SEQ ID NO 43
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as D isomer of
      D-2-aminobutyric acid(D-Dab)
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 43

Xaa Lys Arg Pro Xaa Gly Xaa Ser Xaa Xaa
1               5                   10

<210> SEQ ID NO 44
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (1)..(1)
<223> OTHER INFORMATION: Xaa at position 1 is defined as D-Dab
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)

<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 44

Xaa Leu Arg Pro Xaa Gly Xaa Ser Xaa Xaa
1               5                   10

<210> SEQ ID NO 45
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as DOrn
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 45

Xaa Leu Arg Pro Xaa Gly Xaa Ser Xaa Xaa
1               5                   10

<210> SEQ ID NO 46
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (1)..(1)
<223> OTHER INFORMATION: Xaa at position 1 is defined as DOrn
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 46

Xaa Leu Arg Pro Xaa Gly Xaa Ser Xaa Xaa

-continued

```
1               5                   10

<210> SEQ ID NO 47
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as D isomer of
      3'-pyridylalanine(D-3'Pal)
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 47

Xaa Leu Arg Pro Xaa Gly Xaa Ser Xaa Xaa
1               5                   10

<210> SEQ ID NO 48
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (1)..(1)
<223> OTHER INFORMATION: Xaa at position 1 is defined as D-3'Pal
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 48

Xaa Leu Arg Pro Xaa Gly Xaa Ser Xaa Xaa
1               5                   10

<210> SEQ ID NO 49
<211> LENGTH: 10
<212> TYPE: PRT
<213> ORGANISM: ARTIFICIAL
<220> FEATURE:
```

```
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as D-Lys
<220> FEATURE:
<221> NAME/KEY: misc_feature
<222> LOCATION: (2)..(2)
<223> OTHER INFORMATION: Xaa at position 2 is defined as D-2-Nal
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 49

Xaa Xaa Arg Pro Xaa Gly Xaa Ser Xaa Xaa
1               5                   10

<210> SEQ ID NO 50
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (2)..(2)
<223> OTHER INFORMATION: Xaa at position 2 is defined as D isomer of
      b-2-napthyl-alanine(D-2-Nal)
<220> FEATURE:
<221> NAME/KEY: misc_feature
<222> LOCATION: (5)..(5)
<223> OTHER INFORMATION: Xaa at position 5 is defined as Hyp
<220> FEATURE:
<221> NAME/KEY: misc_feature
<222> LOCATION: (7)..(7)
<223> OTHER INFORMATION: Xaa at position 7 is defined as Cpg
<220> FEATURE:
<221> NAME/KEY: misc_feature
<222> LOCATION: (9)..(9)
<223> OTHER INFORMATION: Xaa at position 9 is defined as Dtic
<220> FEATURE:
<221> NAME/KEY: misc_feature
<222> LOCATION: (10)..(10)
<223> OTHER INFORMATION: Xaa at position 10 is defined as Cpg

<400> SEQUENCE: 50

Leu Xaa Arg Pro Xaa Gly Xaa Ser Xaa Xaa
1               5                   10

<210> SEQ ID NO 51
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as DOrn
<220> FEATURE:
<221> NAME/KEY: misc_feature
<222> LOCATION: (3)..(3)
```

```
<223> OTHER INFORMATION: Xaa at position 3 is defined as Oic
<220> FEATURE:
<221> NAME/KEY: misc_feature
<222> LOCATION: (6)..(6)
<223> OTHER INFORMATION: Xaa at position 6 is defined as Me-Phe
<220> FEATURE:
<221> NAME/KEY: misc_feature
<222> LOCATION: (8)..(8)
<223> OTHER INFORMATION: Xaa at position 8 is defined as D-Beta-NaI

<400> SEQUENCE: 51

Xaa Arg Xaa Pro Gly Xaa Ser Xaa Ile
1               5

<210> SEQ ID NO 52
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (1)..(1)
<223> OTHER INFORMATION: Xaa at position 1 is defined as DOrn
<220> FEATURE:
<221> NAME/KEY: misc_feature
<222> LOCATION: (3)..(3)
<223> OTHER INFORMATION: Xaa at position 3 is defined as Oic
<220> FEATURE:
<221> NAME/KEY: misc_feature
<222> LOCATION: (6)..(6)
<223> OTHER INFORMATION: Xaa at position 6 is defined as Me-Phe
<220> FEATURE:
<221> NAME/KEY: misc_feature
<222> LOCATION: (8)..(8)
<223> OTHER INFORMATION: Xaa at position 8 is defined as D-Beta-NaI

<400> SEQUENCE: 52

Xaa Arg Xaa Pro Gly Xaa Ser Xaa Ile
1               5

<210> SEQ ID NO 53
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
<223> OTHER INFORMATION: Xaa at position 1 is defined as DOrn
<220> FEATURE:
<221> NAME/KEY: misc_feature
<222> LOCATION: (4)..(4)
<223> OTHER INFORMATION: Xaa at position 4 is defined as Oic
<220> FEATURE:
<221> NAME/KEY: misc_feature
<222> LOCATION: (7)..(7)
<223> OTHER INFORMATION: Xaa at position 7 is defined as Me-Phe
<220> FEATURE:
<221> NAME/KEY: misc_feature
<222> LOCATION: (9)..(9)
<223> OTHER INFORMATION: Xaa at position 9 is defined as D-Beta-NaI

<400> SEQUENCE: 53

Xaa Leu Arg Xaa Pro Gly Xaa Ser Xaa Ile
1               5                   10

<210> SEQ ID NO 54
```

```
<211> LENGTH: 10
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (1)..(1)
<223> OTHER INFORMATION: Xaa at position 1 is defined as DOrn
<220> FEATURE:
<221> NAME/KEY: misc_feature
<222> LOCATION: (4)..(4)
<223> OTHER INFORMATION: Xaa at position 4 is defined as Oic
<220> FEATURE:
<221> NAME/KEY: misc_feature
<222> LOCATION: (7)..(7)
<223> OTHER INFORMATION: Xaa at position 7 is defined as Me-Phe
<220> FEATURE:
<221> NAME/KEY: misc_feature
<222> LOCATION: (9)..(9)
<223> OTHER INFORMATION: Xaa at position 9 is defined as D-Beta-NaI

<400> SEQUENCE: 54

Xaa Leu Arg Xaa Pro Gly Xaa Ser Xaa Ile
1               5                   10

<210> SEQ ID NO 55
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (8)..(8)
<223> OTHER INFORMATION: Xaa at position 8 is defined as Me-Phe

<400> SEQUENCE: 55

Leu Arg Pro Pro Gly Phe Ser Xaa Ile
1               5

<210> SEQ ID NO 56
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (8)..(8)
<223> OTHER INFORMATION: Xaa at position 8 is defined as D-Beta-NaI

<400> SEQUENCE: 56

Leu Arg Pro Pro Gly Phe Ser Xaa Ile
1               5

<210> SEQ ID NO 57
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (1)..(1)
```

```
<223> OTHER INFORMATION: Xaa at position 1 is defined as ornithine (Orn)
<220> FEATURE:
<221> NAME/KEY: misc_feature
<222> LOCATION: (3)..(3)
<223> OTHER INFORMATION: Xaa at position 3 is defined as Oic
<220> FEATURE:
<221> NAME/KEY: misc_feature
<222> LOCATION: (6)..(6)
<223> OTHER INFORMATION: Xaa at position 6 is defined as Me-Phe
<220> FEATURE:
<221> NAME/KEY: misc_feature
<222> LOCATION: (8)..(8)
<223> OTHER INFORMATION: Xaa at position 8 is defined as D-Beta-NaI

<400> SEQUENCE: 57

Xaa Arg Xaa Pro Gly Xaa Ser Xaa Ile
1               5

<210> SEQ ID NO 58
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (1)..(1)
<223> OTHER INFORMATION: Xaa at position 1 is defined as Orn
<220> FEATURE:
<221> NAME/KEY: misc_feature
<222> LOCATION: (3)..(3)
<223> OTHER INFORMATION: Xaa at position 3 is defined as Oic
<220> FEATURE:
<221> NAME/KEY: misc_feature
<222> LOCATION: (6)..(6)
<223> OTHER INFORMATION: Xaa at position 6 is defined as Me-Phe
<220> FEATURE:
<221> NAME/KEY: misc_feature
<222> LOCATION: (8)..(8)
<223> OTHER INFORMATION: Xaa at position 8 is defined as D-Beta-NaI

<400> SEQUENCE: 58

Xaa Arg Xaa Pro Gly Xaa Ser Xaa Ile
1               5

<210> SEQ ID NO 59
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: misc_feature
<222> LOCATION: (3)..(3)
<223> OTHER INFORMATION: Xaa at position 3 is defined as Oic
<220> FEATURE:
<221> NAME/KEY: misc_feature
<222> LOCATION: (6)..(6)
<223> OTHER INFORMATION: Xaa at position 6 is defined as Me-Phe
<220> FEATURE:
<221> NAME/KEY: misc_feature
<222> LOCATION: (8)..(8)
<223> OTHER INFORMATION: Xaa at position 8 is defined as D-Beta-NaI

<400> SEQUENCE: 59

Leu Arg Xaa Pro Gly Xaa Ser Xaa Ile
1               5

<210> SEQ ID NO 60
```

```
<211> LENGTH: 9
<212> TYPE: PRT
<213> ORGANISM: ARTIFICIAL
<220> FEATURE:
<223> OTHER INFORMATION: SYNTHETICALLY PRODUCED
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (3)..(3)
<223> OTHER INFORMATION: Xaa at position 3 is defined as Oic
<220> FEATURE:
<221> NAME/KEY: misc_feature
<222> LOCATION: (6)..(6)
<223> OTHER INFORMATION: Xaa at position 6 is defined as Me-Phe
<220> FEATURE:
<221> NAME/KEY: misc_feature
<222> LOCATION: (8)..(8)
<223> OTHER INFORMATION: Xaa at position 8 is defined as D-Beta-NaI

<400> SEQUENCE: 60

Leu Arg Xaa Pro Gly Xaa Ser Xaa Ile
1               5
```

What is claimed is:

1. A peptide antagonist of the bradykinin B1 receptor comprising a sequence of amino acids selected from the group consisting of SEQ ID NOS: 15-18, 23, 25, 26, 39, 41, 45, 44, and 46-51, or a physiologically acceptable salt thereof.

2. A peptide antagonist of the bradykinin B1 receptor comprising a sequence of amino acids selected from the group consisting of SEQ ID NOS: 15-18, 23, 25, and 26, or a physiologically acceptable salt thereof.

3. The peptide of claim 2 comprising a sequence of amino acids selected from the group consisting of SEQ ID NOS: 15-18, 23, 25, and 26.

4. A pharmaceutical composition comprising a peptide antagonist of the bradykinin B1 receptor comprising a sequence of amino acids selected from the group consisting of SEQ ID NOS: 15-18, 23, 25, and 26; and at least one pharmaceutically-acceptable diluent, excipient, or carrier.

5. The peptide of claim 2, wherein the sequence of amino acids is SEQ ID NO: 15.

6. The peptide of claim 2, wherein the sequence of amino acids is SEQ ID NO: 16.

7. The peptide of claim 2, wherein the sequence of amino acids is SEQ ID NO: 17.

8. The peptide of claim 2, wherein the sequence of amino acids is SEQ ID NO: 18.

9. The peptide of claim 2, wherein the sequence of amino acids is SEQ ID NO: 23.

10. The peptide of claim 2, wherein the sequence of amino acids is SEQ ID NO: 25.

11. The peptide of claim 2, wherein the sequence of amino acids is SEQ ID NO: 26.

* * * * *

UNITED STATES PATENT AND TRADEMARK OFFICE
CERTIFICATE OF CORRECTION

| | | |
|---|---|---|
| PATENT NO. | : 7,605,120 B2 | Page 1 of 1 |
| APPLICATION NO. | : 10/972236 | |
| DATED | : October 20, 2009 | |
| INVENTOR(S) | : Ng et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1086 days.

Signed and Sealed this

Fourteenth Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,605,120 B2
APPLICATION NO. : 10/972236
DATED : October 20, 2009
INVENTOR(S) : Ng et al.

It is certified that error appears in the above-identified patent and that said Letters Patent is hereby corrected as shown below:

In the Specification

- Columns 21-22, Table 3, to the right of "(SEQ ID NO:10)", change "Ac Lys Lys Arg Pro Pro Gly Me-Phe Ser D-β-NaI Ile" to --Ac Lys Lys Arg Pro Pro Gly Me-Phe Ser D-β-NaI Ile--.

- Columns 23-24, Table 3, to the right of "(SEQ ID NO:51)", change "DOrn Arg Oic Pro Gly Me-Phe Ser D-β-NaI Ile" to --DOrn Arg Oic Pro Gly Me-Phe Ser D-β-NaI Ile--.

- Columns 23-24, Table 3, to the right of "(SEQ ID NO:52)", change "Ac DOrn Arg Oic Pro Gly Me-Phe Ser D-β-NaI Ile" to --Ac DOrn Arg Oic Pro Gly Me-Phe Ser D-β-NaI Ile--.

- Columns 23-24, Table 3, to the right of "(SEQ ID NO:53)", change "DOrn LysArg Oic Pro Gly Me-Phe Ser D-β-NaI Ile" to --DOrn LysArg Oic Pro Gly Me-Phe Ser D-β-NaI Ile--.

- Columns 23-24, Table 3, to the right of "(SEQ ID NO:54)", change "Ac DOrnLys Arg Oic Pro Gly Me-Phe Ser D-β-NaI Ile" to --Ac DOrnLys Arg Oic Pro Gly Me-Phe Ser D-β-NaI Ile--.

- Columns 23-24, Table 3, to the right of "(SEQ ID NO:55)", change "Lys Arg Pro Pro Gly Phe Ser D-β-NaI Ile" to --Lys Arg Pro Pro Gly Phe Ser D-β-NaI Ile--.

- Columns 23-24, Table 3, to the right of "(SEQ ID NO:56)", change "Ac Lys Arg Pro Pro Gly Phe Ser D-β-NaI Ile" to --Ac Lys Arg Pro Pro Gly Phe Ser D-β-NaI Ile--.

- Columns 25-26, Table 3, to the right of "(SEQ ID NO:57)", change "Orn Arg Oic Pro Gly Me-Phe Ser D-β-NaI Ile" to --Orn Arg Oic Pro Gly Me-Phe Ser D-β-NaI Ile--.

- Columns 25-26, Table 3, to the right of "(SEQ ID NO:58)", change "Ac Orn Arg Oic Pro Gly Me-Phe Ser D-β-NaI Ile" to --Ac Orn Arg Oic Pro Gly Me-Phe Ser D-β-NaI Ile--.

Signed and Sealed this
Twenty-fifth Day of February, 2014

Michelle K. Lee
*Deputy Director of the United States Patent and Trademark Office*

CERTIFICATE OF CORRECTION (continued)
U.S. Pat. No. 7,605,120 B2

- Columns 25-26, Table 3, to the right of "(SEQ ID NO:59)", change "Lys Arg Oic Pro Gly Me-Phe Ser D-β-NaI Ile" to --Lys Arg Oic Pro Gly Me-Phe Ser D-β-NaI Ile--.

- Columns 25-26, Table 3, to the right of "(SEQ ID NO:60)", change "Ac Lys Arg Oic Pro Gly Me-Phe Ser D-β-NaI Ile" to --Ac Lys Arg Oic Pro Gly Me-Phe Ser D-β-NaI Ile--.

- Column 59, line <213>, above "<400> SEQUENCE: 1", change "ORGANISM: HUMAN" to --ORGANISM: Homo sapiens--.

- Column 59, line <213>, above "<400> SEQUENCE: 2", change "ORGANISM: HUMAN" to --ORGANISM: Homo sapiens--.

- Column 61, line <213>, above "<400> SEQUENCE: 4", change "ORGANISM: HUMAN" to --ORGANISM: Homo sapiens--.

- Column 65, line <223>, above "<400> SEQUENCE: 10", change "(D-Beta-NaI)" to --(D-Beta-Nal)--.

- Column 65, below "<400> SEQUENCE: 10", change "Leu Leu Arg Pro Pro Gly Xaa Ser Xaa Ile" to --Lys Lys Arg Pro Pro Gly Xaa Ser Xaa Ile--.

- Column 69, below "<400> SEQUENCE: 15", change " Xaa Leu Arg Pro Xaa Gly Xaa Ser Xaa Xaa" to -- Xaa Lys Arg Pro Xaa Gly Xaa Ser Xaa Xaa--.

- Column 69, below "<400> SEQUENCE: 16", change " Xaa Leu Arg Pro Xaa Gly Xaa Ser Xaa Xaa" to -- Xaa Lys Arg Pro Xaa Gly Xaa Ser Xaa Xaa--.

- Column 71, below "<400> SEQUENCE: 17", change " Xaa Leu Arg Pro Xaa Gly Xaa Ser Xaa Xaa" to -- Xaa Lys Arg Pro Xaa Gly Xaa Ser Xaa Xaa --.

- Column 71, below "<400> SEQUENCE: 18", change " Xaa Leu Arg Pro Xaa Gly Xaa Ser Xaa Xaa" to --Xaa Lys Arg Pro Xaa Gly Xaa Ser Xaa Xaa--.

- Column 73, below "<400> SEQUENCE: 21", change "Leu Arg Pro Xaa Gly Xaa Ser Xaa Xaa" to --Lys Arg Pro Xaa Gly Xaa Ser Xaa Xaa--.

- Column 75, below "<400> SEQUENCE: 22", change " Xaa Leu Arg Pro Xaa Gly Xaa Ser Xaa Xaa" to -- Xaa Lys Arg Pro Xaa Gly Xaa Ser Xaa Xaa--.

- Column 75, below "<400> SEQUENCE: 23", change "Leu Xaa Arg Pro Xaa Gly Xaa Ser Xaa Xaa" to -- Lys Xaa Arg Pro Xaa Gly Xaa Ser Xaa Xaa--.

- Column 75, below "<400> SEQUENCE: 24", change " Leu Xaa Arg Pro Xaa Gly Xaa Ser Xaa Xaa" to -- Lys Xaa Arg Pro Xaa Gly Xaa Ser Xaa Xaa--.

CERTIFICATE OF CORRECTION (continued)
U.S. Pat. No. 7,605,120 B2

- Column 77, below "<400> SEQUENCE: 25", change " Leu Xaa Arg Pro Xaa Gly Xaa Ser Xaa Xaa" to -- Lys Xaa Arg Pro Xaa Gly Xaa Ser Xaa Xaa --.

- Column 77, below "<210> SEQ ID NO 26", change "<211> LENGTH: 11" to --<211> LENGTH: 10--, and change "<223> OTHER INFORMATION: Xaa at position 1 is defined as 2Nal" to --<223> Xaa at position 2 is defined as 2Nal--.

- Column 77, lines 11-14, of "<210> SEQ ID NO 26", below "<223> OTHER INFORMATION: Xaa at position 1 [now "2"] is defined as 2Nal", delete the immediately following lines <220> through <223>.

- Column 77, lines 19-22, of "<210> SEQ ID NO 26", below "<223> OTHER INFORMATION: Xaa at position 5 is defined as Hyp", delete the immediately following lines <220> through <223>.

- Column 77, lines 27-30, of "<210> SEQ ID NO 26", below "<223> OTHER INFORMATION: Xaa at position 7 is defined as Cpg", delete the immediately following lines <220> through <223>.

- Column 77, lines 39-42, of "<210> SEQ ID NO 26", below "<223> OTHER INFORMATION: Xaa at position 10 is defined as Cpg", delete the immediately following lines <220> through <223>.

- Column 79, below "<400> SEQUENCE: 26", change "Leu Xaa Xaa Arg Pro Xaa Gly Xaa Ser Xaa Xaa" to -- Lys Xaa Arg Pro Xaa Gly Xaa Ser Xaa Xaa --.

- Column 79, below "<210> SEQ ID NO 31", change "<211> LENGTH: 12" to --<211> LENGTH: 11--; change "<222> LOCATION: (3) . . (3)" to --<222> (2) . . (3)--; and change "<223> OTHER INFORMATION: Xaa at position 3 is defined as CH2-CH2-CH2-CH2-CH2-CH2" to -- <223> Linker (CH2-CH2-CH2-CH2-CH2-CH2) between position 2 and 3--.

- Column 79, below "<400> SEQUENCE: 31", change "Cys Gly Xaa Lys Arg Pro Pro Gly Phe Ser Pro Leu" to --Cys Gly Lys Arg Pro Pro Gly Phe Ser Pro Leu--.

- Column 81, thirteenth line from the top, at "<223> OTHER INFORMATION", above "<400> SEQUENCE: 32", change "D-Beta-NaI" to --D-Beta-Nal--.

- Column 81, below "<400> SEQUENCE: 32", change "Cys Gly Gly Gly Gly Gly Leu Leu Arg Pro Pro Gly Xaa Ser Xaa Ile" to --Cys Gly Gly Gly Gly Gly Lys Lys Arg Pro Pro Gly Xaa Ser Xaa Ile--.

- Column 85, below "<210> SEQ ID NO 37", below "<223> OTHER INFORMATION: SYNTHETICALLY PRODUCED", delete all misc_feature comments through line "<223> OTHER INFORMATION: Xaa at position 11 is defined as Cpg", and insert therefor:

```
--<220>
<221> MISC_FEATURE
<222> (1)..(1)
<223> Acylation

<220>
<221> misc _feature
<222> (5)..(5)
<223> Xaa at position 5 is defined as Hyp <220>
<221> misc_feature
<222> (7)..(7)
<223> Xaa at position 7 is defined as Cpg <220>
<221> misc_feature
<222> (9)..(9)
<223> Xaa at position 9 is defined as Dtic <220>
<221> misc_feature
<222> (10)..(10)
<223> Xaa at position 10 is defined as Cpg--.
```

- Column 87, below "<400> SEQUENCE: 39", change "Cys Gly Gly Gly Gly Gly Xaa Leu Arg Pro Xaa Gly Xaa Ser Xaa Xaa" to --Cys Gly Gly Gly Gly Gly Xaa Lys Arg Pro Xaa Gly Xaa Ser Xaa Xaa--.

- Column 87, below "<400> SEQUENCE: 40", change "Cys Gly Gly Gly Gly Gly Xaa Leu Arg Pro Xaa Gly Xaa Ser Xaa Xaa" to --Cys Gly Gly Gly Gly Gly Xaa Lys Arg Pro Xaa Gly Xaa Ser Xaa Xaa--.

- Column 89, below "<400> SEQUENCE: 41", change "Cys Gly Gly Gly Gly Gly Leu Xaa Arg Pro Xaa Gly Xaa Ser Xaa Xaa" to --Cys Gly Gly Gly Gly Gly Lys Xaa Arg Pro Xaa Gly Xaa Ser Xaa Xaa--.

- Column 91, below "<400> SEQUENCE: 44", change "Xaa Leu Arg Pro Xaa Gly Xaa Ser Xaa Xaa" to --Xaa Lys Arg Pro Xaa Gly Xaa Ser Xaa Xaa--.

- Column 91, below "<400> SEQUENCE: 45", change "Xaa Leu Arg Pro Xaa Gly Xaa Ser Xaa Xaa" to --Xaa Lys Arg Pro Xaa Gly Xaa Ser Xaa Xaa--.

- Column 91, below "<400> SEQUENCE: 46", change "Xaa Leu Arg Pro Xaa Gly Xaa Ser Xaa Xaa" to --Xaa Lys Arg Pro Xaa Gly Xaa Ser Xaa Xaa--.

CERTIFICATE OF CORRECTION (continued)  Page 5 of 6
U.S. Pat. No. 7,605,120 B2

- Column 93, below "<210> SEQ ID NO 47", at line <223>, change "(D-3'Pa1)" to --(D-3'Pal)-- (i.e., final numeral "1" should be lower case letter "L").

- Column 93, below "<400> SEQUENCE: 47", change " Xaa Leu Arg Pro Xaa Gly Xaa Ser Xaa Xaa" to -- Xaa Lys Arg Pro Xaa Gly Xaa Ser Xaa Xaa --.

- Column 93, below "<210> SEQ ID NO 48", at line <223>, change "D-3'Pa1" to --D-3'Pal-- (i.e., final numeral "1" should be lower case letter "L").

- Column 93, below "<400> SEQUENCE: 48", change " Xaa Leu Arg Pro Xaa Gly Xaa Ser Xaa Xaa" to -- Xaa Lys Arg Pro Xaa Gly Xaa Ser Xaa Xaa --.

- Column 95, below "<400> SEQUENCE: 50", change " Leu Xaa Arg Pro Xaa Gly Xaa Ser Xaa Xaa" to -- Lys Xaa Arg Pro Xaa Gly Xaa Ser Xaa Xaa --.

- Column 97, line "<223>", above "<400> SEQUENCE: 51", change "D-Beta-NaI" to --D-Beta-Nal--.

- Column 97, line "<223>", above "<400> SEQUENCE: 52", change "D-Beta-NaI" to --D-Beta-Nal--.

- Column 97, line "<223>", above "<400> SEQUENCE: 53", change "D-Beta-NaI" to --D-Beta-Nal--.

- Column 97, below "<400> SEQUENCE: 53", change " Xaa Leu Arg Xaa Pro Gly Xaa Ser Xaa Ile" to -- Xaa Lys Arg Xaa Pro Gly Xaa Ser Xaa Ile --.

- Column 99, line "<223>", above "<400> SEQUENCE: 54", change "D-Beta-NaI" to --D-Beta-Nal--.

- Column 99, below "<400> SEQUENCE: 54", change " Xaa Leu Arg Xaa Pro Gly Xaa Ser Xaa Ile " to -- Xaa Lys Arg Xaa Pro Gly Xaa Ser Xaa Ile --.

- Column 99, line "<223>", above "<400> SEQUENCE: 55", change "OTHER INFORMATION: Xaa at position 8 is defined as Me-Phe" to --Xaa at position 8 is defined as D-Beta-Nal--.

- Column 99, below "<400> SEQUENCE: 55", change "Leu Arg Pro Pro Gly Phe Ser Xaa Ile" to --Lys Arg Pro Pro Gly Phe Ser Xaa Ile--.

- Column 99, line "<223>", above "<400> SEQUENCE: 56", change "D-Beta-NaI" to --D-Beta-Nal--.

CERTIFICATE OF CORRECTION (continued)
U.S. Pat. No. 7,605,120 B2

- Column 99, below "<400> SEQUENCE: 56", change "Leu Arg Pro Pro Gly Phe Ser Xaa Ile" to --Lys Arg Pro Pro Gly Phe Ser Xaa Ile--.

- Column 101, line "<223>", above "<400> SEQUENCE: 57", change "D-Beta-NaI" to --D-Beta-Nal--.

- Column 101, line "<223>", above "<400> SEQUENCE: 58", change "D-Beta-NaI" to --D-Beta-Nal--.

- Column 101, line "<223>", above "<400> SEQUENCE: 59", change "D-Beta-NaI" to --D-Beta-Nal--.

- Column 101, below "<400> SEQUENCE: 59", change "Leu Arg Pro Pro Gly Phe Ser Xaa Ile" to --Lys Arg Pro Pro Gly Phe Ser Xaa Ile--.

- Column 103, line "<223>", above "<400> SEQUENCE: 60", change "D-Beta-NaI" to --D-Beta-Nal--.

- Column 103, below "<400> SEQUENCE: 60", change "Leu Arg Xaa Pro Gly Xaa Ser Xaa Ile" to --Lys Arg Xaa Pro Gly Xaa Ser Xaa Ile--.

- Column 103, Lines 30-31: change "consisting of SEQ ID NOS: 15-18, 23, 25, 26, 39, 41, 45, 44, and 46-51," to --consisting of SEQ ID NOS: 15-18, 23, 25, 26, 39-41, 43, 44, and 46-54,--.